(12) United States Patent
Tommasi et al.

(10) Patent No.: US 8,362,063 B2
(45) Date of Patent: Jan. 29, 2013

(54) ARYLSULFONAMIDE BASED MATRIX METALLOPROTEASE INHIBITORS

(75) Inventors: Ruben Alberto Tommasi, Stow, MA (US); Michael Shultz, Lexington, MA (US); Leslie Wighton McQuire, Warren, NJ (US); Pascal Rigollier, Hagenthal-le-Bas (FR); Olivier Rogel, Hésingue (FR); Claus Ehrhardt, Lörrach (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/481,983

(22) Filed: May 29, 2012

(65) Prior Publication Data

US 2012/0258954 A1    Oct. 11, 2012

Related U.S. Application Data

(62) Division of application No. 12/933,988, filed as application No. PCT/EP2009/053390 on Mar. 23, 2009, now Pat. No. 8,222,424.

(60) Provisional application No. 61/038,882, filed on Mar. 24, 2008.

(51) Int. Cl.
*A61K 31/416* (2006.01)
*C07D 231/54* (2006.01)

(52) U.S. Cl. ..................................... 514/406; 548/362.5

(58) Field of Classification Search .................. 514/406; 548/362.5
See application file for complete search history.

(56) References Cited

U.S. PATENT DOCUMENTS

| | | | |
|---|---|---|---|
| 4,156,732 A | 5/1979 | Lang et al. | |
| 4,940,793 A | 7/1990 | Botre et al. | |
| 6,277,987 B1 | 8/2001 | Kukkola et al. | |
| 2004/0077642 A1* | 4/2004 | Berg et al. | 514/228.2 |

FOREIGN PATENT DOCUMENTS

| | | |
|---|---|---|
| EP | 1288199 A1 | 3/2003 |
| GB | 893072 | 4/1962 |

OTHER PUBLICATIONS

Hu et al. (Bioorg. Med. Chem. Lett., 17 (2007) 3613-3617).*
Die Saureehloride der m-Sulfo-benzoesaure und ihre Umsetzungen mit Aminen und Phenolen; von Paul Ruggli; Organisch-chemisches La boratorium ~der Eidg. Technischen Hochschule, Zurich.; pp. 197-211.
Synthesis and Inhibitory Activity on Carbonic Anhydrase of Some New Sulphide Analogues Studied by Means of a New Method; Claudio Bothe; J. Med. Chem. 1986,29, 1814-1820.
Aminoalkenylbenzenesulfonamides with Hypotensive and Histamine-Releasing Properties; William J. Hudak, Journal of Medicinal Chemistry, 1970, vol. 3 13, No. 5, pp. 895-900.

* cited by examiner

*Primary Examiner* — Robert Havlin
(74) *Attorney, Agent, or Firm* — Sophie Binet Cross

(57) ABSTRACT

The present invention provides a compound of formula (I):

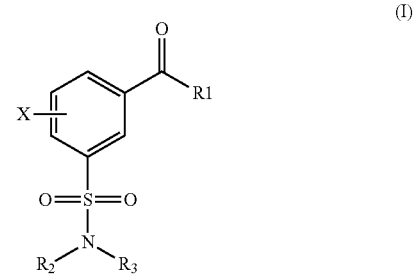

said compound is inhibitor of MMP-2, and/or MMP-8, and/or MMP-9, and/or MMP-12 and/or MMP-13, and thus can be employed for the treatment of a disorder or disease characterized by abnormal activity of MMP-2, and/or MMP-8, and/or MMP-9, and/or MMP-12 and/or MMP-13. Accordingly, the compound of formula (I) can be used in treatment of disorders or diseases mediated by MMP-2, and/or MMP-8, and/or MMP-9, and/or MMP-12, and/or MMP-13. Finally, the present invention also provides a pharmaceutical composition.

6 Claims, No Drawings

ARYLSULFONAMIDE BASED MATRIX METALLOPROTEASE INHIBITORS

This application is a divisional application of U.S. application Ser. No. 12/933,988, filed Sep. 22, 2010 now U.S. Pat. No. 8,222,424, which is a U.S. National Phase filing of International Serial No. PCT/EP2009/053390 filed Mar. 23, 2009, and claims priority to U.S. Provisional Application No. 61/038,882 filed Mar. 24, 2008, the contents of which are incorporated herein by reference in their entirety.

The present invention relates to novel compounds that are useful as inhibitors of matrix metalloproteinases such as matrix metalloproteinase 2 (MMP-2), matrix metalloproteinase 8 (MMP-8), matrix metalloproteinase 9 (MMP-9), matrix metalloproteinase 12 (MMP-12) and matrix metalloproteinase 13 (MMP-13).

Matrix metalloproteinases (MMPs) are proteinases that are involved in the breakdown and remodeling of the extracellular matrices (ECM) under a variety of physiological and pathological conditions. MMPs, which comprise a family of more than 20 members, use $Zn^{2+}$ in the active sites to catalyze hydrolyses of ECM. Based on their substrate specificities, they can be broadly classified into three subfamilies: collagenase, stromelysins and gelatinases.

Under normal physiological conditions, these enzymes serve many important functions, including wound healing and tissue remodeling. However, when these enzymes are over activated, they can over-degrade ECM, resulting in disease conditions. For example, MMP-2 and MMP-9 (both are gelatinases) are thought to be involved in the pathogenesis of inflammatory, infectious, and neoplastic diseases in many organs. Excess activity of MMP-8, also known as collagenase-2 or neutrophil collagenase, is associated with diseases such as pulmonary emphysema and osteoarthritis. See Balbin et al., "Collagenase 2 (MMP-8) expression in murine tissue-remodeling processes, analysis of its potential role in post-partum involution of the uterus," *J. Biol. Chem.*, 273(37): 23959-23968 (1998). Excess activity of MMP-12, also known as macrophage elastase or metalloelastase, plays a key role in tumor invasion, arthritis, atherosclerosis, Alport syndrome, and chronic obstructive pulmonary disease (COPD). MMP-1 and MMP-13 are involved in the proteolysis of collagen. Excessive degradation of collagen is associated with the development of various diseases, including osteoarthritis. See e.g., P. G. Mitchell et al., "Cloning, expression, and type II collagenolytic activity of matrix metalloproteinase-13 from human osteoarthritic cartilage," *J Clin Invest.* 1996 Feb. 1; 97(3): 761-768.

Many MMP inhibitors are known in the art. However, existing MMP inhibitors are typically based on hydroxamic acid derivatives. For example, U.S. Pat. No. 6,500,983 issued to Koffirsch et al. discloses the use of hydroxamic acid derivatives as MMP inhibitors. U.S. Pat. Nos. 6,277,987 and 6,410,580 issued to Kukkola et al. disclose suflonyl amino acid and sulfonylamino hydroxamic acid derivatives as MMP inhibitors. The hydroxamic acid moiety in these inhibitors binds to the active site $Zn^{2+}$ to inhibit enzymatic activities.

While prior art hyroxamic acid-based MMP inhibitors are effective in inhibiting MMPs, there remains a need for different types of MMP inhibitors.

The present invention provides new MMP inhibitors that are based on arylsulfonamides. Various embodiments of the invention are described herein. It will be recognised that features specified in each embodiment may be combined with other specified features to provide further embodiments.

In one aspect, the present invention provides a compound of formula (I)

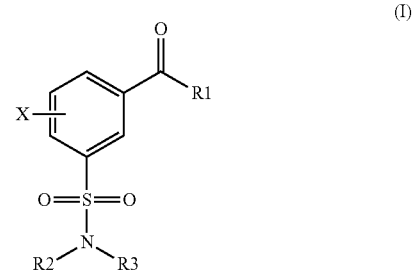

wherein $R_1$ is selected from aryl, heteroaryl, heterocycloalkyl, each optionally substituted by one to five substituents selected from the group consisting of 1) alkyl, cycloalkyl, aryl, heteroaryl, heterocycloalkyl, alkoxy, alkoxy-alkyl-, alkoxycarbonyl, $R_4$—O—, $R_5C(O)$—, $R_6SO_2$—, $(R_7)NH$—$C(O)$—, or $(R_8)(R_9)N$—, each of which is further optionally substituted by one to two substituents selected from halo, alkoxy, alkyl, hydroxy, dialkylamino, alkylsulfonyl, heterocycloalkyl, or aryloxy; or 2) hydroxy, halo, nitro, amino, carboxy, or $HC(O)$—;

$R_2$ and $R_3$ are independently hydrogen, or $(C_1$-$C_7)$ alkyl.

$R_4$, $R_5$, $R_6$, $R_7$, $R_8$ and $R_9$ are independently alkyl, aryl, aryl-alkyl-, heterocycloalkyl, or heteroaryl each of which is further optionally substituted by one to five substituents selected from the group consisting of $(C_1$-$C_7)$ alkyl, halo, hydroxy, $(C_1$-$C_7)$ alkoxy, and aryl; and X is selected from hydrogen, amine, cyano, halogen, nitro, alkyl-S—, alkyl-SO—, alkyl-$SO_2$—, $H_2N$—$SO_2$—, $R_5$—C(O)—, alkyl, or $R_4$—O, wherein $R_4$ and $R_5$ are defined above; or a pharmaceutically acceptable salt thereof, or an optical isomer thereof; or a mixture of optical isomers.

Preferably, the present invention provides compound formula (I), wherein $R_1$ is selected from $(C_6$-$C_{12})$ aryl, (5-14) membered heteroaryl, or (4-14) membered heterocycloalkyl, each of which is optionally substituted by one to three substituents selected from the group consisting of $HC(O)$—, (5-9) membered heteroaryl, or (4-9) membered heterocycloalkyl, $(C_1$-$C_7)$ alkyl, $(C_3$-$C_7)$ cycloakyl, $R_4$—O—, $R_5$—C(O)—, $R_6$—$SO_2$—, $(R_7)NH$—$C(O)$—, or $(R_8)(R_9)N$—, wherein $R_4$, $R_5$, $R_6$, $R_7$, $R_8$ and $R_9$ are independently $(C_1$-$C_7)$ alkyl or $(C_6$-$C_{12})$ aryl, each of which is further optionally substituted by one to two substituents selected from the group consisting of $(C_1$-$C_7)$ alkyl, halo, hydroxy, $(C_1$-$C_7)$ alkoxy, $(C_8$-$C_{12})$ aryl, $(C_1$-$C_7)$ dialkylamino, or (4-9) membered heterocycloalkyl; $R_2$ and $R_3$ are independently hydrogen, or $(C_1$-$C_7)$ alkyl; X is selected from hydrogen, amine, cyano, halogen, nitro, alkyl-S—, alkyl-SO—, alkyl-$SO_2$—, $H_2N$—$SO_2$—, $R_4$—$C(O)$—, alkyl, or $R_5$—O—, wherein $R_4$ and $R_5$ are defined above; or a pharmaceutically acceptable salt thereof, or an optical isomer thereof; or a mixture of optical isomers.

In one aspect, the present invention provides a compound of formula (II)

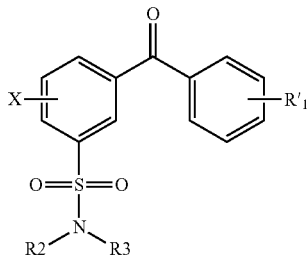

(II)

wherein R'₁ is selected from hydrogen, alkyl, alkoxy, cycloakyl, $R_4$—O—, $R_5C(O)$—, $R_6SO_2$—, $(R_7)NH$—C(O)—, or $(R_8)(R_9)N$—, aryl, heteroaryl, heterocycloalkyl, said aryl, heteroaryl, and heterocycloalkyl are optionally substituted by one or two substituents selected from hydroxyl, halo, alkyl, carboxyl, alkoxycarbonyl, and HC(O)—;

wherein $R_4$, $R_5$, $R_6$, $R_7$, $R_8$ and $R_9$ are independently alkyl or aryl each of which is optionally substituted by one to five substituents selected from the group consisting of $(C_1-C_7)$ alkyl, halo, hydroxyl, $(C_1-C_7)$ alkoxy, and aryl;

$R_2$ and $R_3$ are independently hydrogen, or $(C_1-C_7)$ alkyl;

X is selected from hydrogen, cyano, halogen, nitro, alkyl-S—, alkyl-SO—, alkyl-SO₂—, H₂N—SO₂—, $R_5$—C(O)—, alkyl, or $R_4$—O, wherein $R_4$ and $R_5$ are independently alkyl or aryl each of which is optionally substituted by substituents selected from the group consisting of $(C_1-C_7)$ alkyl, halo, hydroxyl, $(C_1-C_7)$ alkoxy, and aryl; or a pharmaceutically acceptable salt thereof, or an optical isomer thereof; or a mixture of optical isomers.

Preferably, the present invention provides the compound of formula (II), wherein R'₁ is selected from $(C_1-C_7)$ alkyl, $(C_3-C_7)$ cycloalkyl, $(C_1-C_7)$ alkoxy, HC(O)—, (5-9) membered heteroaryl, or (4-9) membered heterocycloalkyl, or $(C_6-C_{12})$ aryl, said $(C_6-C_{12})$ aryl, (5-9) membered heteroaryl, and (4-9) membered heterocycloalkyl are optionally substituted by one or two substituents selected from hydroxy, halo, $(C_1-C_7)$ alkyl, carboxyl, $(C_1-C_7)$ alkoxycarbonyl, and HC(O)—;

$R_2$ and $R_3$ are hydrogen;

X is halogen, or $(C_1-C_7)$ alkoxy; or a pharmaceutically acceptable salt thereof, or an optical isomer thereof; or a mixture of optical isomers.

In one aspect, the present invention provides a compound of formula (III)

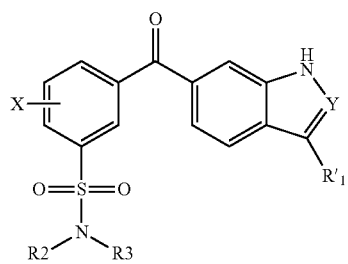

(III)

wherein R'₁ is selected from hydrogen, alkyl, cycloakyl, $R_5C(O)$—, $R_6SO_2$—, $(R_7)NH$—C(O)—, or $(R_8)(R_9)N$—, aryl, heteroaryl, heterocycloalkyl, said aryl, heteroaryl, and heterocycloalkyl are optionally substituted by one or two substituents selected from alkyl-SO₂—, alkyl-C(O)—, heterocycloalkyl-alkyl-, alkyl-alkoxy-, alkoxy-, alkyl, aryl, cycloalkyl, halo, alkoxy-alkyl-, alkyl-O—C(O)—, cycloalkyl-alkyl-, dialkylamino-alkoxy-, and dialkylamino-alkyl-;

wherein $R_5$, $R_6$, $R_7$, $R_8$ and $R_9$ are independently alkyl or aryl, each of which is optionally substituted by one to five substituents selected from the group consisting of $(C_1-C_7)$ alkyl, halo, hydroxy, $(C_1-C_7)$ alkoxy, and aryl;

$R_2$ and $R_3$ are hydrogen;

X is selected from hydrogen, cyano, halogen, nitro, alkyl-S—, alkyl-SO—, alkyl-SO₂—, H₂N—SO₂—, $R_5$—C(O)—, alkyl, or $R_4$—O, wherein $R_4$ and $R_5$ are independently alkyl or aryl each of which is optionally substituted by substituents selected from the group consisting of $(C_1-C_7)$ alkyl, halo, hydroxy, $(C_1-C_7)$ alkoxy, and aryl;

Y is C or N; or a pharmaceutically acceptable salt thereof, or an optical isomer thereof; or a mixture of optical isomers.

Preferably, the present invention provides the compound of formula (III), wherein R'₁ is selected from hydrogen, $(C_1-C_4)$ alkyl, $(C_6-C_{12})$ aryl, (5-9) membered heteroaryl, $(C_3-C_7)$ cycloalkyl-$(C_1-C_4)$ alkyl-, each of which is optionally substituted by one or two substituents selected from the group consisting of $(C_1-C_4)$ alkyl-SO₂—, $(C_1-C_4)$ alkyl-C(O)—, (5-9) membered-heterocycloalkyl-$(C_1-C_4)$ alkyl-, $(C_1-C_4)$ alkyl-$(C_1-C_4)$ alkoxy-, $(C_1-C_4)$ alkoxy-, $(C_1-C_4)$ alkyl, $(C_3-C_7)$ cycloalkyl, halogen, $(C_1-C_4)$ alkoxy-$(C_1-C_4)$ alkyl-, $(C_1-C_4)$ alkyl-O—C(O)—, $(C_1-C_4)$ dialkylamino-$(C_1-C_4)$ alkoxy-, and $(C_1-C_4)$ dialkylamino-$(C_1-C_4)$ alkyl-;

$R_2$ and $R_3$ are hydrogen;

X is hydrogen, halogen, or $(C_1-C_7)$ alkyl; or a pharmaceutically acceptable salt thereof, or an optical isomer thereof; or a mixture of optical isomers.

Also preferably, the present invention provides the compound of formula (III), wherein R'₁ is hydrogen, $(C_1-C_4)$ alkyl, phenyl, pyridine, said pyridine is optionally substituted by one or two substituents selected from $(C_3-C_7)$ cycloalkyl, $(C_1-C_4)$ alkyl, halo, $(C_1-C_4)$ alkoxy-$(C_1-C_4)$ alkyl-, (5-9) membered-heterocycloalkyl-$(C_1-C_4)$ alkyl-, (5-9) membered-heterocycloalkyl-$(C_1-C_4)$ alkoxy-, and $(C_1-C_4)$ dialkylamino-$(C_1-C_4)$ alkyl-; $R_2$ and $R_3$ are hydrogen; X is halogen; Y is C or N; or a pharmaceutically acceptable salt thereof, or an optical isomer thereof; or a mixture of optical isomers.

The present invention provides for compounds of formula I, II and III, and pharmaceutical compositions employing such compounds and for methods of using such compounds.

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

The term "aryl" refers to monocyclic or bicyclic aromatic hydrocarbon groups having 6-20 carbon atoms in the ring portion. Preferably, the aryl is a $(C_6-C_{12})$ aryl. Non-limiting examples include phenyl, biphenyl, naphthyl or tetrahydronaphthyl, each of which may optionally be substituted by 1-4 substituents, such as optionally substituted alkyl, trifluoromethyl, cycloalkyl, halo, hydroxy, alkoxy, acyl, alkyl-C (O)—O—, aryl-O—, heteroaryl-O—, optionally substituted amino, thiol, alkylthio, arylthio, nitro, cyano, carboxy, alkyl-O—C(O)—, carbamoyl, alkylthiono, sulfonyl, sulfonamido, heterocycloalkyl and the like.

Furthermore, the term "aryl" as used herein, refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

As used herein, the term "carbamoyl" refers to H$_2$NC (O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aryl-alkyl-NHC(O)—, alkyl(aryl-alkyl)-NC(O)— and the like.

As used herein, the term "sulfonamido" refers to alkyl-S (O)$_2$—NH—, aryl-S(O)$_2$—NH—, aryl-alkyl-S(O)$_2$—NH—, heteroaryl-S(O)$_2$—NH—, heteroaryl-alkyl-S(O)$_2$—NH—, alkyl-S(O)$_2$—N(alkyl)-, aryl-S(O)$_2$—N(alkyl)-, aryl-alkyl-S (O)$_2$—N(alkyl)-, heteroaryl-S(O)$_2$—N(alkyl)-, heteroaryl-alkyl-S(O)$_2$—N(alkyl)- and the like.

As used herein, the term "heterocycloalkyl" or "heterocyclo" refers to an optionally substituted, fully saturated, partially saturated, or unsaturated, aromatic or nonaromatic heterocyclic group, e.g., which is a 4- to 7-membered monocyclic, 7- to 12-membered bicyclic or 10- to 15-membered tricyclic ring system, which can be fused, pedant, or spiro, and has at least one heteroatom in at least one carbon atom-containing ring. Each ring of the heterocyclic group containing a heteroatom may have 1, 2 or 3 heteroatoms selected from nitrogen, oxygen and sulfur atoms, where the —CH$_2$— on the ring can be replaced with a —C(O)— group, and sulfur heteroatom can also optionally be oxidized to S(O) or S(O)$_2$ groups. In the fused ring system, one ring can be nonaromatic heterocyclic ring, and the other ring(s) can be cycloalkyl, aryl, or heteroaryl. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroindolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

As used herein, the term "sulfonyl" refers to R—SO$_2$—, wherein R is hydrogen, alkyl, aryl, heteroaryl, aryl-alkyl, heteroaryl-alkyl, aryl-O—, heteroaryl-O—, alkoxy, aryloxy, cycloalkyl, or heterocycloalkyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. As used herein, the term "lower alkoxy" refers to the alkoxy groups having about 1-7 preferably about 1-4 carbons.

As used herein, the term "acyl" refers to a group R—C (O)— of from 1 to 10 carbon atoms of a straight, branched, or cyclic configuration or a combination thereof, attached to the parent structure through carbonyl functionality. Such group may be saturated or unsaturated, and aliphatic or aromatic. Preferably, R in the acyl residue is alkyl, or alkoxy, or aryl, or heteroaryl. Also preferably, one or more carbons in the acyl residue may be replaced by nitrogen, oxygen or sulfur as long as the point of attachment to the parent remains at the carbonyl. Examples include but are not limited to, acetyl, benzoyl, propionyl, isobutyryl, tert-butoxycarbonyl, benzyloxycarbonyl and the like. Lower acyl refers to acyl containing one to four carbons.

As used herein, the term "cycloalkyl" refers to optionally substituted saturated or unsaturated monocyclic, bicyclic or tricyclic hydrocarbon groups of 3-12 carbon atoms, each of which may be substituted by one or more substituents, such as alkyl, halo, oxo, hydroxy, alkoxy, alkyl-C(O)—, acylamino, carbamoyl, alkyl-NH—, (alkyl)$_2$N—, thiol, alkylthio, nitro, cyano, carboxy, alkyl-O—C(O)—, sulfonyl, sulfonamido, sulfamoyl, heterocycloalkyl and the like. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1] hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.

As used herein, the term "aryloxy" refers to both an —O-aryl and an —O— heteroaryl group.

As used herein, the term acylamino refers to the group—NRC(O)R' where each of R and R' is independently hydrogen, alkyl, aryl, heteroaryl, or heterocycloalkyl, where both R and R' groups are optionally joined to form a heterocyclic group (e.g., morpholino) wherein alkyl, aryl, heteroaryl and heterocycloalkyl are as defined herein.

As used herein, the term "heteroaryl" refers to a 5-14 membered monocyclic- or bicyclic- or fused polycyclic-aromatice ring system, having 1 to 8 heteroatoms selected from N, O or S. Preferably, the heteroaryl is a 5-10 membered aromatic ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloalkyl, or heterocycloalkyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4-aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-oxazinyl, 1-, 3-, or 5-1H-pyrazolo[4,3-d]-oxazolyl, 2-, 4-, or 5-4H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

As used herein, the term "halo" refers to fluoro, chloro, bromo, and iodo.

As used herein, the term "isomers" refers to different compounds that have the same molecular formula. Also as used herein, the term "an optical isomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences*, 20th ed., Mack Publishing Company, Easton, Pa., (1985), which is herein incorporated by reference.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The term "therapeutically effective amount" of a compound of the present invention refers to an amount of the compound of the present invention that will elicit the biological or medical response of a subject, or ameliorate symptoms, slow or delay disease progression, or prevent a disease, etc. In a preferred embodiment, the "effective amount" refers to the amount that inhibits or reduces expression or activity of MMP-2, and/or MMP-8, and/or MMP-9, and/or MMP-12, and/or MMP-13.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "a disorder" or "a disease" refers to any derangement or abnormality of function; a morbid physical or mental state. See *Dorland's Illustrated Medical Dictionary*, (W.B. Saunders Co. 27th ed. 1988).

As used herein, the term "inhibition" or "inhibiting" refers to the reduction or suppression of a given condition, symptom, or disease, or a significant decrease in the baseline activity of a biological activity or process. Preferably, the condition is associated with or mediated by MMP-2, and/or MMP-8, and/or MMP-9, and/or MMP-12, and/or MMP-13.

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Any asymmetric carbon atom on the compounds of the present invention can be present in the (R)-, (S)- or (R,S)-configuration, preferably in the (R)- or (S)-configuration. Substituents at atoms with unsaturated bonds may, if possible, be present in cis-(Z)- or trans (E)-form. Therefore, the compounds of the present invention can be in the form of one of the possible isomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure geometric or optical isomers, diastereomers, racemates, for example, by silica gel chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound.

The invention includes pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of formula (I), for example, those incorporating a radioactive isotope, are useful in drug and/or substrate tissue distribution studies. The radioactive isotopes $^{3}H$ and $^{14}C$ are particularly useful for this purpose in view of their ease of incorporation and ready means of detection. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labelled compounds of formula (I) can generally be prepared by conventional techniques known to those skilled in the art or by processes analogous to those described herein using an appropriate isotopically-labelled reagent in place of the non-labelled reagent previously employed.

Finally, compounds of the present invention are either obtained in the free form, as a salt thereof, or as prodrug derivatives thereof.

When a basic group is present in the compounds of the present invention, the compounds can be converted into acid addition salts thereof, in particular, acid addition salts with the imidazolyl moiety of the structure, preferably pharmaceutically acceptable salts thereof. These are formed, with inorganic acids or organic acids. Suitable inorganic acids include but are not limited to, hydrochloric acid, sulfuric acid, a phosphoric or hydrohalic acid. Suitable organic acids include but are not limited to, carboxylic acids, such as ($C_1$-$C_4$) alkanecarboxylic acids which, for example, are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, organic sulfonic acids, such as ($C_1$-$C_4$) alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

When an acidic group is present in the compounds of the present invention, the compounds can be converted into salts with pharmaceutically acceptable bases. Such salts include alkali metal salts, like sodium, lithium and potassium salts; alkaline earth metal salts, such as calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids such as arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

When both a basic group and an acid group are present in the same molecule, the compounds of the present invention can also form internal salts.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds are inactive or have low activity compared to the corresponding active drug compound, that contains one or more protective groups and are converted to an active form by metabolism or solvolysis. Both the active drug form and any released metabolic products should have acceptably low toxicity. Typically, the formation of active drug compound involves a metabolic process or reaction that is one of the follow types:

1. Oxidative reactions, such as oxidation of alcohol, carbonyl, and acid functions, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-delakylation, oxidative O- and S-delakylation, oxidative deamination, as well as other oxidative reactions.

2. Reductive reactions, such as reduction of carbonyl groups, reduction of alcoholic groups and carbon-carbon double bonds, reduction of nitrogen-containing functions groups, and other reduction reactions.

3. Reactions without change in the state of oxidation, such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. See, Cheng et al., US20040077595, application Ser. No. 10/656, 838. Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, *The Practice of Medicinal Chemistry*, Ch. 31-32, Ed. Werriuth, Academic Press, San Diego, Calif., 2001.

Exemplary prodrugs are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

In view of the close relationship between the compounds, the compounds in the form of their salts and the pro-drugs, any reference to the compounds of the present invention is to be understood as referring also to the corresponding pro-drugs of the compounds of the present invention, as appropriate and expedient.

Furthermore, the compounds of the present invention, including their salts, can also be obtained in the form of their hydrates, or include other solvents used for their crystallization.

The compounds of the present invention have valuable pharmacological properties, they are useful as inhibitors of matrix metalloproteinases such as matrix metalloproteinase 2 (MMP-2), matrix metalloproteinase 8 (MMP-8), matrix metalloproteinase 9 (MMP-9), matrix metalloproteinase 12 (MMP-12) and matrix metalloproteinase 13 (MMP-13). MMP-2 and MMP-9 are gelatinases involved in tissue remodeling and both have been implicated in aiding the tumor metastasis process. As such, selective inhibition of these gelatinase proteases may be useful in the treatment of metastatic tumors. MMP-8, also known as collagenase-2 or neutrophil collagenase, is also involved in tissue remodeling. Inhibition of MMP-8 is useful for the prevention, delay of progression, or treatment of diseases such as fibrotic diseases of the lung, degradative diseases such as pulmonary emphysema, and osteoarthritis, etc. MMP-12, also known as macrophage elastase or metalloelastase, is able to degrade extracellular matrix components such as elastin and is involved in tissue remodeling processes. MMP-12 has been indicated to be a key protein in the pathogenesis of tumor invasineness, arthritis, atherosclerosis, Alport syndrome, and chromical obstructive pulmonary disease (COPD). MMP-13, also known as collagenase 3, has been indicated in (1) extracellular matrix degradation and cell-matrix interaction associated with metastasis especially as observed in invasive breast cancer lesions and in malignant epithelia growth in skin carcinogenesis; and (2) during primary ossification and skeletal remodelling (M. Stahle-Backdahl et al., (1997) *Lab. Invest.* 76 (5):717-728; N. Johansson et al., (1997) *Dev. Dyn.* 208(3): 387-397), in destructive joint diseases such as rheumatoid and osteo-arthritis (D. Wernicke et al., (1996) *J. Rheumatol.* 23:590-595; P. G. Mitchell et al., (1996) *J. Clin. Invest.* 97(3): 761-768; O. Lindy et al., (1997) *Arthritis Rheum.* 40(8:1391-1399); and the aseptic loosening of hip replacements (S. Imai et al., (1998) *J. Bone Joint Surg. Br.* 80(4):701-710). MMP13 has also been implicated in chronic adult periodontitis as it has been localised to the epithelium of chronically inflamed mucosa human gingival tissue (V. J. Uitto et al., (1998) *Am. J. Pathol.* 152(6):1489-1499) and in remodelling of the collagenous matrix in chronic wounds (M. Vaalamo et al., (1997) *J. Invest. Dermatol.* 109(1): 96-101).

Accordingly, the compounds of the present invention are also useful for treatment of a disorder or a disease mediated by MMP-2, and/or MMP-8, and/or MMP-9, and/or MMP-12, and/or MMP-13. In particular, the compounds of the present invention are useful for treatment of at least one disorder or disease selected from Alport syndrome, asthma, rhinitis, chronic obstructive pulmonary diseases (COPD), arthritis (such as rheumatoid arthritis and osteoarthritis), atherosclerosis and restenosis, cancer invasion and metastasis, diseases involving tissue destruction, loosening of hip joint replacements, periodontal disease, fibrotic disease, infarction and heart disease, liver and renal fibrosis, endometriosis, diseases related to the weakening of the extracellular matrix, heart failure, aortic aneurysms, CNS related diseases such as Alzheimer's disease and Multiple Sclerosis (MS), hematological disorders.

Additionally, the present invention provides:
 a compound of the present invention for use as a medicament;
 the use of a compound of the present invention for the preparation of a pharmaceutical composition for the delay of progression and/or treatment of a disorder or disease mediated by MMP-2, and/or MMP-8, and/or MMP-9, and/or MMP-12, and/or MMP-13.
 the use of a compound of the present invention for the preparation of a pharmaceutical composition for the delay of progression and/or treatment of a disorder or disease mediated by MMP-2, and/or MMP-8, and/or MMP-9, and/or MMP-12, and/or MMP-13.
 the use of a compound of the present invention for the preparation of a pharmaceutical composition for the delay of progression and/or treatment of a disorder or disease selected from Alport syndrome, asthma, rhinitis, chronic obstructive pulmonary diseases (COPD), arthritis (such as rheumatoid arthritis and osteoarthritis), atherosclerosis and restenosis, cancer invasion and metastasis, diseases involving tissue destruction, loosening of hip joint replacements, periodontal disease, fibrotic disease, infarction and heart disease, liver and renal fibrosis, endometriosis, diseases related to the weakening of the extracellular matrix, heart failure, aortic aneurysms, CNS related diseases such as Alzheimer's disease and Multiple Sclerosis (MS), hematological disorders.

The compounds of formula (I) and (II) can be prepared by any of four general ketone synthesis procedures described in the following section.

The first method (method A) is the construction of the ketone by Friedel Crafts acylation, as in the following example:

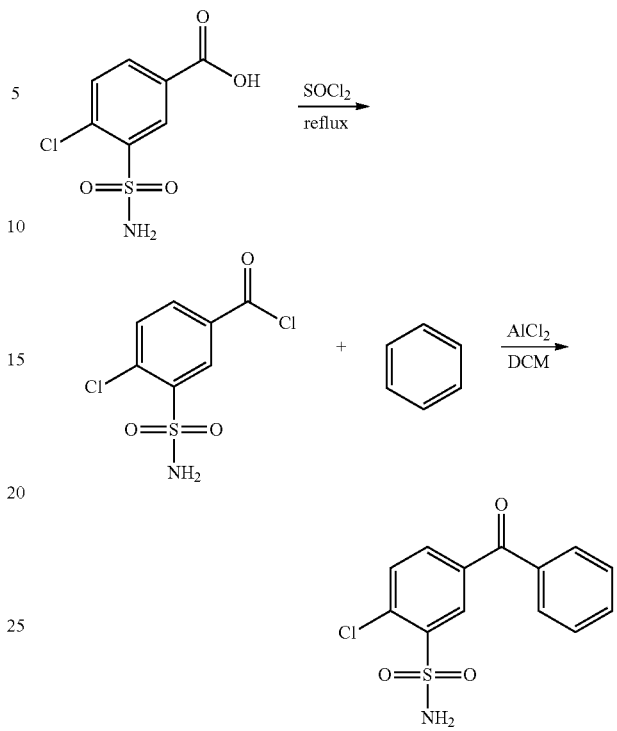

Typical procedure for the synthesis of benzoyl chlorides

4-Chloro-3-sulfamoyl-benzoyl chloride

A mixture of 4-chloro-3-sulfamoyl-benzoic acid (50 g, 212 mmol) and thionyl chloride (31 mL, 424 mmol) are heated to reflux for 5 h then allowed to cool to room temperature. To this mixture is added hexane and the resulting solid is filtered, washed with hexane and dried in vacuo to yield 52.3 g (97%) of the title compound as an off-white solid.

Typical Procedure for the Formation of Ketones by Friedel Crafts Acylation.

The requisite ketone may be generated by mixing the coupling partners in methylene chloride (dichloromethane) or 1,2-dichloroethane and introducing a Lewis acid (aluminium chloride, MeAlCl$_2$ or Me$_2$AlCl) to promote acylium ion formation which undergoes the Friedel Crafts acylation.

The second method (method B) involves the addition of an organometallic reagent to an aldehyde and subsequent oxidation of the resultant alcohol to the ketone. Typically, the requisite aldehyde (2-chloro-5-formyl-benzenesulfonamide), is synthesized as shown below.

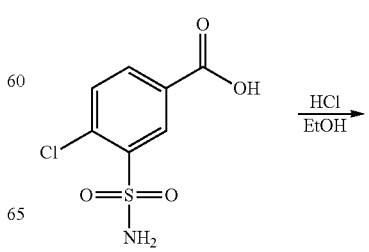

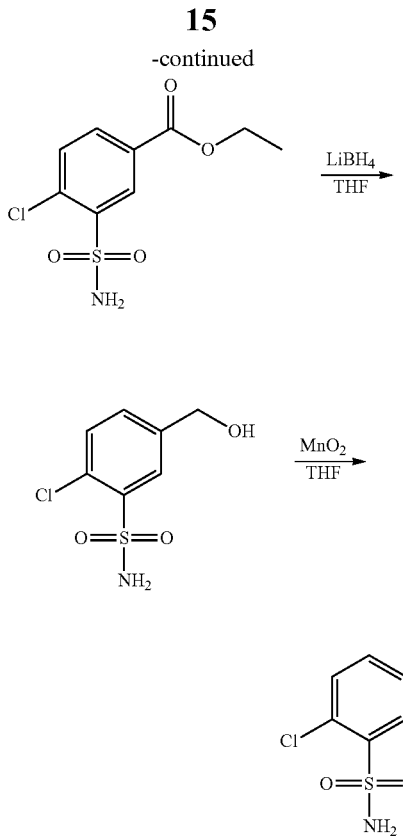

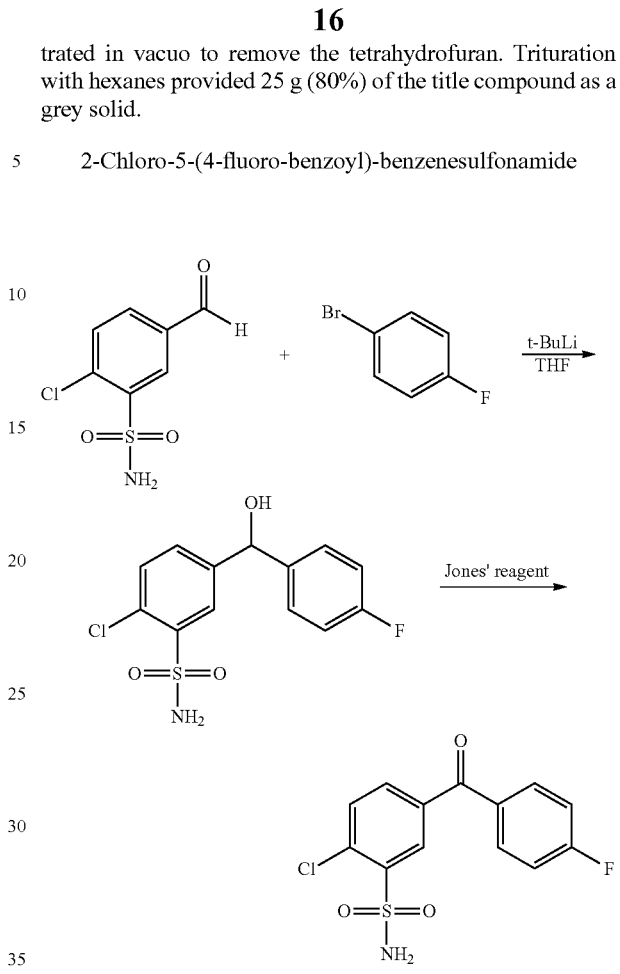

General procedure for the synthesis of
2-chloro-5-formyl-benzenesulfonamide

4-Chloro-3-sulfamoyl-benzoic acid ethyl ester

To a suspension of 4-chloro-3-sulfamoyl-benzoic acid (50 g, 212 mmol) in 500 mL ethanol is bubbled HCl gas for 10 minutes. The resulting suspension is then heated at reflux for 16 h, cooled and concentrated in vacuo. The resulting residue is recrystallized from isopronanol to yield 55.9 g (99%) of the title compound as an off-white solid.

2-Chloro-5-hydroxymethyl-benzenesulfonamide

To a solution of 4-chloro-3-sulfamoyl-benzoic acid ethyl ester (46.95 g, 166 mmol) in 500 mL of dry tetrahydrofuran is added dropwise, with stirring, 199 mL of a 2 M solution of lithium borohydride in tetrahydrofuran. The mixture is stirred and refluxed for 5 hr, then left at room temperature for 18 h, and is then carefully diluted with 400 mL of water. The mixture is cooled to 4° C. for 24 hours and filtered to yield 32.7 g (82%) of the title compound as an off-white solid.

2-Chloro-5-formyl-benzenesulfonamide

To a well stirred solution of 2-chloro-5-hydroxymethyl-benzenesulfonamide (31.6 g, 143 mmol) in 300 mL tetrahydrofuran is added 62.0 g (713 mmol) of $MnO_2$. The resulting solution is heated at reflux for 16 h, filtered through Celite then through a 0.4 µM Teflon filter and the filtrate is concentrated in vacuo to remove the tetrahydrofuran. Trituration with hexanes provided 25 g (80%) of the title compound as a grey solid.

2-Chloro-5-(4-fluoro-benzoyl)-benzenesulfonamide

2-Chloro-5-[(4-fluoro-phenyl)-hydroxy-methyl]-benzenesulfonamide

A solution of 590 mg of 1-bromofluorobenzene (1.11 mmol, 3 equivalent) in 10 mL of anhydrous tetrahydrofuran is stirred at −78° C. as 3.9 mL of tert-butyllithium (1.7 M in cyclohexane, 6.66 mmol, 6 equivalent) is added drop-wise. The reaction mixture is stirred at −78° C. for 2 h, then is transfered to a previously prepared a solution of 243 mg of 2 chloro-5-formyl-benzenesulfonamide (1.11 mmol, 1 equivalent) and 0.65 mL of tert-butyllithium (1.7 M in cyclohexane, 1 equivalent) in 10 mL of anhydrous tetrahydrofuran. The reaction is allowed to warm to room temperature and stirred at room temperature for 18 h. The reaction is quenched with 0.1 N HCl and then extracted several times with ethyl acetate. The combined organic extracts are dried over sodium sulfate, and concentrated in vacuo to give 65 mg of the title compound which is carried on without further purification.

2-Chloro-5-(4-fluoro-benzoyl)-benzenesulfonamide

A solution of 65 mg of 2-chloro-5-((4-fluoro-phenyl)-hydroxy-methyl)-benzenesulfonamide in 1 mL of acetone is stirred at room temperature as 0.2 mL of 3 M Jones' reagent is added. The reaction mixture is stirred at room temperature for 30 minutes then diluted with ethyl acetate, filtered through celite, the filtrate is concentrated in vacuo. The crude product is purified by silica gel chromatography to give 48 mg of the title compound as white foam. $^1$H NMR (CDCl$_3$): 5.15 (br, 2H), 7.12-7.30 (m, 3H), 7.70 (d, J=8 Hz, 1H), 7.80-7.90 (m, 2H), 7.90-8.0 (dd, 1H), 8.5 (d, J=2 Hz, 1H). MS (m/z): 312 (M−1).

In the third method (method C), ketone synthesis is accomplished using an electrophilic Weinreb amide coupling partner in lieu of the aldehyde.

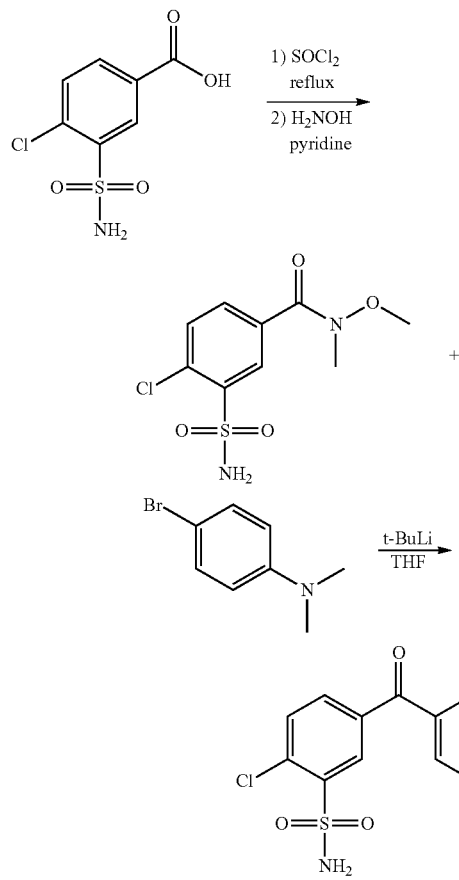

Typical Procedure for the Formation of the Weinreb Coupling Partner: Preparation of 4-Chloro-N-methoxy-N-methyl-3-sulfamoyl-benzamide 4-Chloro-3-sulfamoyl-benzoic acid (5 g) is treated with 20.5 mL of thionyl chloride and heated to reflux for 5.5 h. Thionyl chloride is removed and the residue is dried at 50° C. in vacuo to give 5.6 g of 4-chloro-3-sulfamoyl-benzoyl chloride as a tan powder. This material is taken up in 28 mL of methylene chloride and treated at 0° C. with 2.64 g of N,O-dimethylhydroxylamine hydrochloride followed by 10.9 mL of pyridine and stirred overnight at room temperature. The reaction mixture is quenched at 0° C. with 19 mL of 3 N aqueous HCl and extracted with ethyl acetate. The organics are combined, washed with saturated aqueous sodium bicarbonate, 0.1 N aqueous HCl and a saturated sodium chloride solution, dried over magnesium sulfate and concentrated in vacuo. The resulting crystals are filtered through a short pad of silica gel (1:2 hexanes/ethyl acetate) to give the title compound as a white powder. MS (m/z): (M−1) 277; Rf 0.36 (1:2 hexanes/ethyl acetate).

Typical Procedure for the Formation of Ketones Using Method C:

2-Chloro-5-(4-dimethylamino-benzoyl)-benzene-sulfonamide

A solution of 1.07 g of N,N-dimethyl-4-bromoamine (5.39 mmol, 3 equivalent) in 30 mL of anhydrous tetrahydrofuran is stirred at −78° C. as 6.34 mL of tert-butyllithium (1.7 M in pentane, 10.78 mmol, 6 equivalent) is added. The reaction mixture is stirred at −78° C. for 10 minutes, then 430 mg of 4-chloro-N-methoxy-N-methyl-3-sulfamoyl-benzamide (1.54 mmol, 1 equivalent) in 10 mL of anhydrous tetrahydrofuran is added. The reaction is stirred at −78° C. for 20 minutes, then warmed to room temperature and stirred at room temperature for 18 h. The reaction is quenched with water and extracted with ethyl acetate. The combined organic extracts are washed with a saturated sodium chloride solution, dried over sodium sulfate, and concentrated in vacuo. After purification by flash chromatography, 300 mg of product is obtained as a solid (yield, 57%). $^1$H NMR (400 MHz, CDCl$_3$): δ 3.10 (s, 6H), 5.17 (s, 2H), 6.68 (d, 2H, J=12 Hz), 7.64 (d, 1H, J=8 Hz), 7.74 (d, 2H, J=8 Hz), 7.86 (d, 1H, J=2 Hz), 8.41 (s, 1H). MS (m/z): 339 (M+1).

In the fourth method (method D), ketone synthesis is accomplished using palladium cross coupling of an organostannane with an acid chloride.

Typical Procedure for Palladium Cross Coupling, Synthesis of Indazole Derivatives

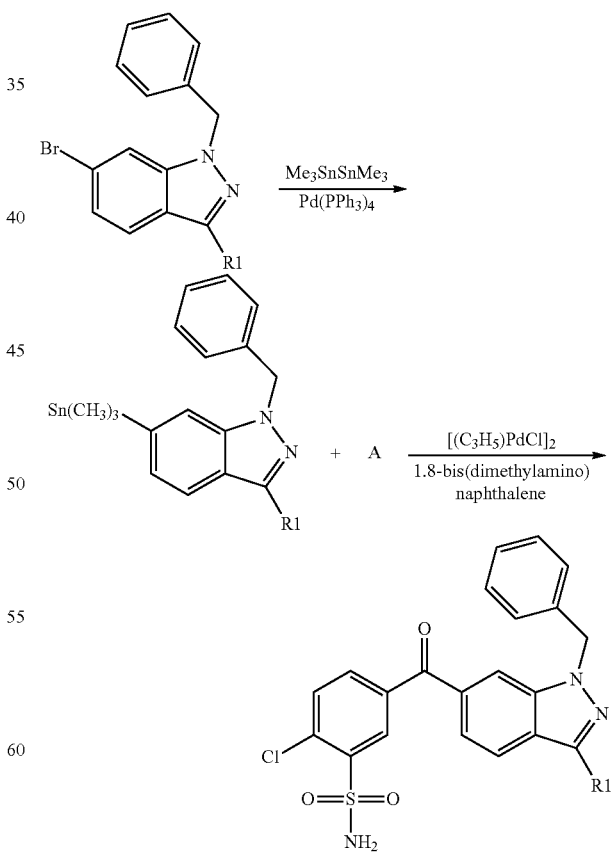

The bromo-indazole compound (1.0 equivalent) and hexamethylditin (1.25 equivalent) are dissolved in deoxygenated toluene under a nitrogen atmosphere. Palladium tetrakis (triphenylphosphine) (0.07 equivalent) is added, and the mixture is heated to reflux until LC-MS analysis shows complete disappearance of the bromide. The reaction mixture is portioned between pH 7 buffer and ethyl acetate, and the combined organics are dried over sodium sulfate, and concentrated to provide crude arylstannane which is used without additional purification. The arylstannane (1.0 equivalent) and 1,8-bis(dimethyl amino)naphthalene (0.5 equivalent) dissolved in tetrahydrofuran is treated with benzoyl chloride (1.0 equivalent). After a few minutes, allylpalladium chloride dimer (0.05 equivalent) is added, the reaction mixture is stirred for 5 min at ambient temperature and then refluxed for 2-18 h. After cooling to ambient temperature, the reaction is diluted with dichloromethane, washed with saturated aqueous sodium bicarbonate, and saturated aqueous sodium chloride. Drying with sodium sulfate, filtration, and concentration gives a crude product, which is purified by flash chromatography to afford a beige solid.

One of ordinary skill in the art would appreciate that modifications of these general ketone synthetic schemes are possible without departing from the scope of the invention. It is also obvious to those skilled in the art that other methods of ketone synthesis are available and these four methods are merely a sampling of strategies for ketone preparation.

In starting compounds and intermediates which are converted to the compounds of the present invention in a manner described herein, functional groups present, such as amino, thiol, carboxyl and hydroxy groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, carboxy, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, room temperature or elevated temperatures, preferably at or near the boiling point of the solvents used, and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Preferably, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable compositions for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

The present invention further provides anhydrous pharmaceutical compositions and dosage forms comprising the compounds of the present invention as active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical compositions contain a therapeutically effective amount of a compound of the invention as defined above, either alone or in a combination with another therapeutic agent, e.g., each at an effective therapeutic dose as reported in the art. In one embodiment, such therapeutic agents include, for example, 1) $AT_1$ receptor antagonists selected from the group consisting of abitesartan, benzyllosartan, candesartan, elisartan, embusartan, enoltasosartan, eprosartan, fonsartan, forasartan, glycyllosartan, irbesartan, isoteoline, losartan, milfasartan, olmesartan, opomisartan, pratosartan, ripisartan, saprisartan, saralasin, sarmesin, tasosartan, telmisartan, valsartan, zolasartan; Kissei KRH-94, Lusofarmaco LR-B/057, Lusofarmaco LR-B/081, Lusofarmaco LR B/087, Searle SC-52458, Sankyo CS-866, Takeda TAK-536, Uriach UR-7247, A-81282, A-81988, BIBR-363, BIBS39, BIBS-222, BMS-180560, BMS-184698, CGP-38560A, CGP-48369, CGP-49870, CGP-63170, CI-996, CV-11194, DA-2079, DE-3489, DMP-811, DuP-167, DuP-532, GA-0056, E-4177, EMD-66397, EMD-73495, EXP-063, EXP-929, EXP-3174, EXP-6155, EXP-6803, EXP-7711, EXP-9270, FK-739, HN-65021, HR-720, ICI-D6888, ICI-D7155, ICI-D8731, KR1-1177, KT3-671, KW-3433, L-158809, L-158978, L-159282, L-159689, L-159874, L-161177, L-162154, L-162234, L-162441, L-163007, L-163017, LY-235656, LY-285434, LY-301875, LY-302289, LY-315995, ME-3221, PD-123177, PD-123319, PD-150304, RG-13647, RWJ-38970, RWJ-46458, S-8307, S-8308, SL-91.0102, U-96849, U-97018, UP-269-6, UP-275-22, WAY-126227, WK-1492.2K, WK-1360, X-6803, XH-148, XR-510, YM-358, YM-31472, ZD-6888, ZD-7155 and ZD-8731 which are all known per se, or any physiologically compatible salts, solvates, prodrugs or esters thereof; 2) non-selective alpha-adrenoceptor antagonists, e.g. tolazoline or phenoxybenzamine; 3) selective alpha-adrenoceptor antagonists, e.g. doxazosin, prazosin, terazosin or urapidil; beta-adrenoceptor antagonists, e.g. acebutolol, alprenolol, atenolol, betaxolol, bisoprolol, bupranolol, carazolol, carteolol, celiprolol, mepindolol, metipranolol, metoprolol, nadolol, oxprenolol, penbutolol, pindolol, propranolol, sotalol and timolol; 4) mixed antagonists of alpha- and beta-adrenoceptors, e.g. carvedilol or labetolol; ganglion blockers, e.g. reserpine or guanethidine; 5) alpha2-adrenoceptor agonists (including centrally acting alpha2-adrenoceptor agonists), e.g. clonidine, guanfacine, guanabenz methyldopa and moxonidine; 6) rennin inhibitors, e.g. alskiren; 7) ACE inhibitors, e.g. benazepril, captopril, cilazapril, enalapril, fosinopril, imidapril, lisinopril, moexipril, quinapril, perindopril, ramipril, spirapril or trandolapril; 8) mixed or selective endothelin receptor antagonists e.g. atrasentan, bosentan, clazosentan, darusentan, sitaxsentan, tezosentan, BMS-193884 or J-104132; direct vasodilators, e.g. diazoxide, dihydralazine, hydralazine or minoxidil; 9) mixed ACE/NEP dual inhibitors, e.g. omapatrilat; ECE inhibitors, e.g. FR-901533; PD-069185; CGS-26303; CGS-34043; CGS-35066; CGS-30084; CGS-35066; SM-19712; Ro0677447; 10) selective NEP inhibitors; 11) vasopressin antagonists; 12) aldosterone receptor antagonists, e.g. eplerenone; 13) aldosterone inhibitors; 14) angiotensin vaccine; 15) urotensin II receptor antagonists; and 16) antiinflamatory agents or antirheumatic agents.

In another embodiment, such therapeutic agents include antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY 142886 from Array PioPharma, AZD6244 from AstraZeneca, PD181461 from Pfizer and leucovorin.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active agent" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating agent" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino]

methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, e.g. imatinib;

h) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

j) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; PD184352 or QAN697 (a PI3K inhibitor) or AT7519 (CDK inhibitor);

k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the 5-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

l) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, or CDC25, e.g. okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIAT™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

Furthermore, the combinations as described above can be administered to a subject via simultaneous, separate or sequential administration (use). Simultaneous administration (use) can take place in the form of one fixed combination with two or more active ingredients, or by simultaneously administering two or more compounds that are formulated independently. Sequential administration (use) preferably means administration of one (or more) compounds or active ingredients of a combination at one time point, other compounds or active ingredients at a different time point, that is, in a chronically staggered manner, preferably such that the combination shows more efficiency than the single compounds administered independently (especially showing synergism). Separate administration (use) preferably means administration of the compounds or active ingredients of the combination independently of each other at different time points, preferably meaning that two compounds are administered such that no overlap of measurable blood levels of both compounds are present in an overlapping manner (at the same time).

Also combinations of two or more of sequential, separate and simultaneous administrations are possible, preferably such that the combination compound-drugs show a joint therapeutic effect that exceeds the effect found when the combination compound-drugs are used independently at time intervals so large that no mutual effect on their therapeutic efficiency can be found, a synergistic effect being especially preferred.

Additionally, the present invention provides:
a pharmaceutical composition or combination of the present invention for use as a medicament;
the use of a pharmaceutical composition or combination of the present invention for the delay of progression and/or treatment of a disorder or disease mediated by MMP-2, and/or MMP-8, and/or MMP-9, and/or MMP-12 and/or MMP-13.
the use of a pharmaceutical composition or combination of the present invention for the delay of progression and/or treatment of a disorder or disease selected from hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction.

the use of a pharmaceutical composition or combination of the present invention for the delay of progression and/or treatment of a disorder or disease selected from gynecomastia, osteoporosis, prostate cancer, endometriosis, uterine fibroids, dysfunctional uterine bleeding, endometrial hyperplasia, polycystic ovarian disease, infertility, fibrocystic breast disease, breast cancer and fibrocystic mastopathy.

The pharmaceutical composition or combination of the present invention can be in unit dosage of about 1-1000 mg of active ingredients for a subject of about 50-70 kg, preferably about 5-500 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, preferably between about 1-100 mg/kg.

The compounds are particularly useful for the treatment of, for example, inflammatory conditions, osteoarthritis, rheumatoid arthritis and tumors. Beneficial effects are evaluated in pharmacological tests generally known in the art, and as illustrated herein.

Antiinflammatory activity can be determined in standard inflammation and arthritic animal models well-known in the art, e.g. the adjuvant arthritis model in rats and the collagen II induced arthritis model in mice (Mediators of Inflam. 1, 273-279 (1992).

Gelatinase (MMP-2) inhibitory activities can be determined as follows: Stock solutions of substrate (MCA-Lys-Pro-Leu-Gly-Leu-Dpa-Ala-Arg-NH$_2$) are prepared in DMSO at a concentration of 1.4 mM. Stock solutions of inhibitors (0.03 µM-3 mM) are also prepared in DMSO. The inhibitors are diluted into the assay solutions, and the controls use an equal volume of DMSO so that the final DMSO concentration from the inhibitor and substrate dilutions in all assays is 1.0%. Assays are performed in an assay buffer (100 mM sodium chloride, 10 µM ZnCl.Sub 2, 10 mM CaCl.sub.2, 100 mM Tris-Cl pH7.5, 0.05% Brij-35), containing 1.0% DMSO from the substrate and inhibitor additions. The substrate concentration used in the assays is 5 µM. The assays are carried out at 20-25° C. The fluorescence changes, as a result of substrate cleavage, are monitored using an excitation wavelength of 325 nm and an emission wavelength of 405 nm. The reaction mixtures are added in duplicate into appropriate wells of a 384-well assay plate. The reaction mixtures are preincubated with the inhibitors for 60 minutes The reactions are started by the addition of MMP substrate, and the fluorescence intensity changes are measured after 60 minutes The apparent enzyme activity in the presence of an inhibitor is then compared with that in the absence of any inhibitor to determine the inhibition effect of the inhibitor. These techniques are within the knowledge of one skilled in the art. The inhibition results are expressed as the inhibitor concentrations required to effect 50% inhibition (IC$_{50}$) of the enzyme activity, as compared with the control (non-inhibited) reactions.

Illustrative of the invention, compound 80 in the Tables below exhibits an IC$_{50}$ of 55 nM.

Collagenase-3 (MMP-13) inhibitory activity is determined as described above. Recombinant pro-collagenase-3 is activated with 1 mM APMA, and stored in the assay buffer after extensive dialysis in the assay buffer.

Illustrative of the invention, compound 80 in the Tables below exhibits an IC$_{50}$ of about 113 nM.

MMP-12 inhibitory activity is determined as described above

The effect of compounds of the invention in vivo can be determined in rats. Typically, six rats are dosed orally with a compound up to four hours before being injected intra-articularly in both knees (N=12) with 0.1 to 2 ug/knee of recombinant human MMP-13 dissolved 0.05 mL of saline. Two hours later the rats are sacrificed, synovial lavage is collected, and chondroitin sulfate (CS) fragments released into the joint are quantitated. Chondroitin sulfate is measured by an inhibition ELISA using a chondrotin sulfate specific antibody (CS-56-available from Sigma), in an analogous manner to the methods described by Thonar (Thonar, E. J.-M. A., Lenz, M. E., Klinsworth, G. K., Caterson, B., Pachman, L. M., Glickman, P., Katz, R., Huff, J., Keuttner, K. E. Quantitation of keratan sulfate in blood as a marker of cartilage catabolism, Arth. Rheum. 28, 1367-1376 (1985)).

The effect in protecting against cartilage degradation in arthritic disorders can be determined e.g. in a surgical model of osteoarthritis described in Arthritis and Rheumatism, Vol. 26, 875-886 (1983).

The effect of the compounds of the invention for the treatment of emphysema can be determined in animal models described in American Review of Respiratory Disease 117, 1109 (1978).

The antitumor effect of the compounds of the invention can be determined, for example, by measuring the growth of human tumors implanted subcutaneously in Balb/c nude mice according to methodology well-known in the art in comparison to placebo treated mice. Illustrative tumors are, for example, estrogen-dependent human breast carcinoma BT20 and MCF7, human bladder carcinoma T24, human colon carcinoma Colo 205, human lung adenocarcinoma A549, and human ovarian carcinoma NIH-OVCAR3.

The inhibition of tumor metastasis can be determined in two lung metastasis models. In the B16-F10 melanoma model, metastasis is measured by counting the numbers of lung metastasized melanoma nodules produced by intravenously injected B16-F10 melanoma cells into BDF1 treated mice, according to methodology well known in the art. In the HT1080 model, metastasis is quantified by measuring the fluorescence intensity of enhanced green fluorescent protein (EGFP) in the lung of Balb/c nude mice produced by the metastasized tumor from intravenously injected GFP-expressing human fibrosarcoma HT1080 cells. The inhibition is obtained by comparison of compound-treated and placebo-treated mice in both methods. In the HT1080 model, EGFP-expressing HT1080 cells are prepared by limiting dilution method in the presence of geneticin after transfecting the EGFP expression vector (pEGFP-C1) (CLONTECH Laboratories Inc., Palo Alto, Calif.). A suspension of cells ($10^6$ cells/0.1 mL of PBS) is injected intravenously into Balb/c nude mice. After administering test compounds and vehicle p.o. 3 weeks, tumor metastasized lungs of mice are removed after sacrifice and homogenized. After centrifugation, the cells are washed 3 times with lysing reagent (150 mM ammonium chloride, 0.1 mM EDTA-4 Na, 10 mM $KHCO_3$, pH 7.4) to lyse the red blood cells and 2 times with PBS. After centrifugation, EGFP is extracted from cells by 10% Triton in PBS and put into the wells of a 96-well multi plate. The fluorescence intensity is determined using a fluorescence plate reader at the excitation and emission wave lengths of 485 and 530 nm, respectively.

The effect of the compounds of the invention on atherosclerotic conditions can be evaluated using atherosclerotic plaques from cholesterol-fed rabbits which contain activated matrix metalloproteinases as described by Sukhova et al, Circulation 90, I 404 (1994). The inhibitory effect on matrix metalloproteinase enzyme activity in rabbit atherosclerotic plaques can be determined by in situ zymography, as described by Galis et al, J. Clin. Invest. 94, 2493 (1994), and is indicative of plaque rupture.

The compounds of the invention are particularly useful in mammals as antiinflammatory agents for the treatment of, for example, osteoarthritis and rheumatoid arthritis, as antitumor agents for the treatment and prevention of tumors growth, tumor metastasis, tumor invasion or progression, and as antiatherosclerotic agents for the treatment and prevention of the rupture of atherosclerotic plaques.

The present invention also relates to methods of using the compounds of the invention and their pharmaceutically acceptable salts, or pharmaceutical compositions thereof, in mammals for inhibiting the matrix-degrading metalloproteinases, e.g. stromelysin, gelatinase, collagenase and macrophage metalloelastase, for inhibiting tissue matrix degradation, and for the treatment of matrix-degrading metalloproteinase dependent conditions as described herein, e.g. inflammation, rheumatoid arthritis, osteoarthritis, also tumors (tumor growth, metastasis, progression or invasion), pulmonary disorders, and the like described herein. Tumors (carcinomas) include mammalian breast, lung, bladder, colon, prostate and ovarian cancer, and skin cancer, including melanoma and Kaposi's sarcoma.

The following Examples are intended to illustrate the invention and are not to be construed as being limitations thereon. Temperatures are given in degrees Centigrade. If not mentioned otherwise, all evaporations are performed under reduced pressure, preferably between about 15 and 100 mmHg (20-133 mbar). The structures of final products, intermediates and starting materials are confirmed by standard analytical methods, e.g. microanalysis and/or spectroscopic characteristics (e.g. MS, IR, or NMR). Abbreviations used are those conventional in the art.

EXAMPLES

The present invention will now be illustrated by reference to the following examples which set forth particularly advantageous embodiments. However, it should be noted that these embodiments are illustrative and are not to be construed as restricting the invention in any way.

Example 1

3-(4-Methoxy-benzoyl)-benzenesulfonamide

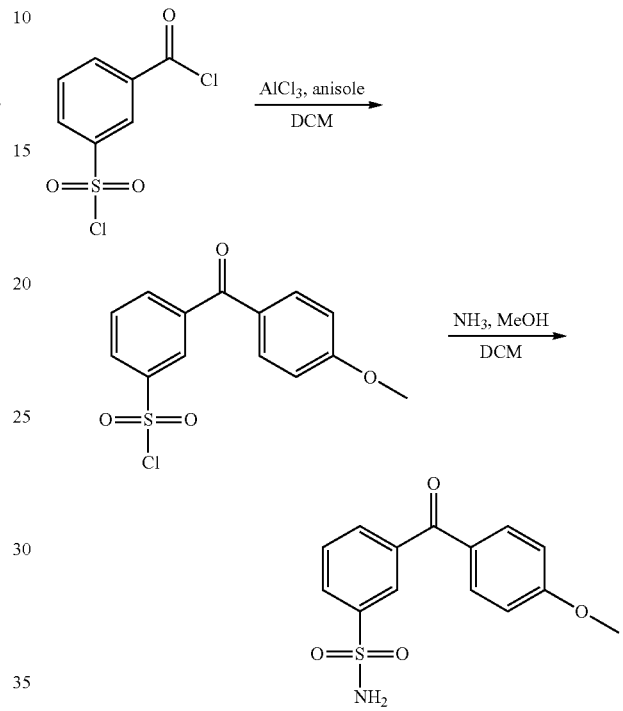

3-(4-Methoxy-benzoyl)-benzenesulfonyl chloride

Under a nitrogen atmosphere, aluminum chloride (7.5 g, 56.5 mmol) is slurried in dichloromethane (150 mL) then 3-chlorosulfonyl-benzoyl chloride (7.5 g, 31.4 mmol) is added and allowed to stir at ambient temperature for 10 minutes. Anisole (4.06 g, 37.65 mmol) is added. The reaction is allowed to stir at ambient temperature for 18 hours. The reaction mixture is poured over ice-cold 6 N HCl and extracted with dichloromethane to give a purple oil. Purification by silica gel chromatography (10% ethyl acetate in hexanes) yielded 4 g (41% yield) of the title compound as a yellow powder. $^1$H NMR ($CDCl_3$): δ 8.5 (t, 1H, J=1.7 Hz), 8.25 (m, 1H), 8.1 (m, 1H), 7.7-7.9 (m, 3H), 7.0 (d, 2H, J=6.9 Hz), 3.9 (s, 3H).

3-(4-Methoxy-benzoyl)-benzenesulfonamide 3-(4-Methoxy-benzoyl)-benzenesulfonyl chloride is dissolved in dichloromethane (10 ml) and treated with 1.7 mL of a 2 M solution of ammonia in methanol. The reaction is stirred at ambient temperature for 2 hours and quenched with 1N HCl. The organic phase is separated and evaporated under reduced pressure to give the crude sulfonamide. Purification by silica gel chromatography (gradient of ethyl acetate in hexanes 5-25%) yielded 100 mg (50% yield) of the title compound. $^1$H NMR ($CDCl_3$, 300 MHz): δ 8.3 (t, 1H, J=1.6 Hz), 8.1 (m, 1H), 7.95 (m, 1H), 7.8 (d, 2H, J=6.98 Hz), 7.65 (t, 1H, J=7.8 Hz), 7.0 (d, 2H, J=6.98 Hz), 4.95 (s, 2H), 3.9 (s, 3H). MP: 119-122° C. LCMS Elution time 0.81 MS (m/z): 291 (M+1). CHN Calc C, 57.72; H, 4.50; N, 4.81 Found C, 57.65; H, 4.33; N, 4.69

Example 2

2-fluoro-5-(4-methoxy-benzoyl)-benzenesulfonamide

3-Chlorosulfonyl-4-fluoro benzoic acid

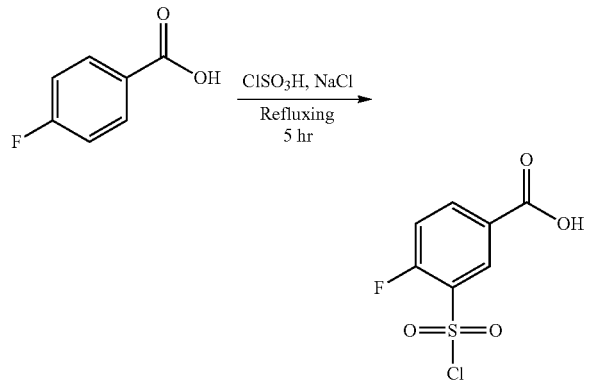

4-Fluoro-benzoic acid (8 g, 57 mmol) is added carefully to chlorosulfonic acid (58 g, 498 mmol) then sodium chloride (10 g, 169 mmol) is added in small portions. After complete addition, the reaction is heated at 160° C. for 5 h. The reaction mixture is cooled down and poured into ice-water. A white solid precipitate is collected and redissolved in ethyl acetate. The organic layer is washed with a saturated sodium chloride solution, dried over magnesium sulfate, filtered, and the solvent is removed in vacuo. The residue is triturated with hexane to give 7 g (51% yield) of the title compound as a white solid. $^1$H NMR (CDCl$_3$): δ 8.78 (m, 1H), 8.52 (m, 1H), 7.5 (t, 1H). MS (m/z): 308 (M−1).

3-Chlorosulfonyl-4-fluoro benzoyl chloride

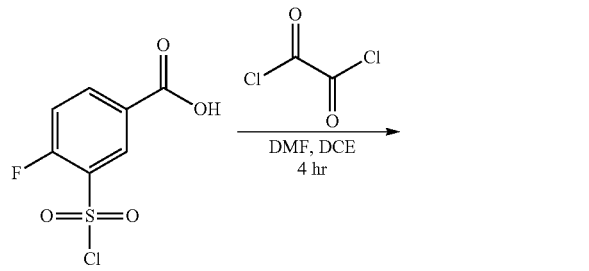

To a suspension of 3-chlorosulfonyl-4-fluoro benzoic acid (2.5 g, 10 mmol) in methylene chloride at 0° C. is added oxalyl chloride (1.33 g, 11 mmol), followed by the addition of 1 drop of N,N,-dimethylformamide. The reaction mixture is warmed up to room temperature and stirred for an additional 4 h. The solvent is removed, and the residue is dried under vacuum for 1 hr to obtain the title compound as an oil, which is used for the next step without further purification.

2-Fluoro-5-(4-methoxy-benzoyl)-benzenesulfonyl chloride

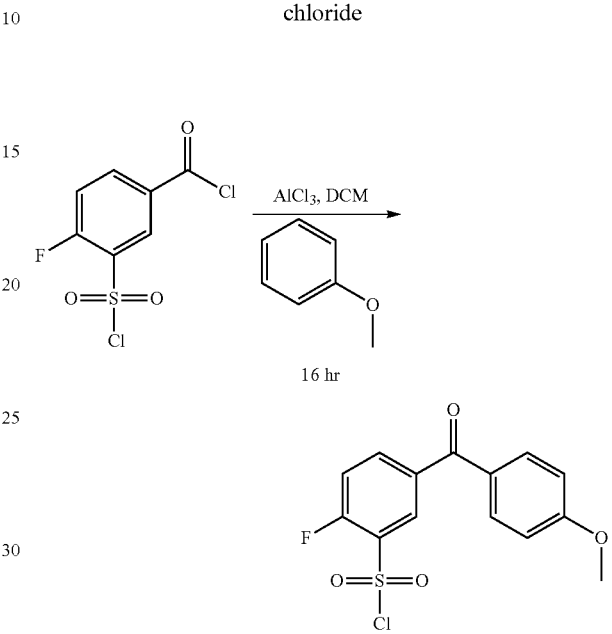

To a suspension of aluminium chloride (2.1 g, 15.7 mmol) in methylene chloride (50 mL) is added 3-chlorosulfonyl-4-fluoro benzoyl chloride (10.5 mmol). The reaction mixture is stirred at room temperature for 10 minutes then anisole (1.36 g, 12.5 mmol) is added. After the mixture is stirred at room temperature for 16 h, the reaction is quenched with 6 N HCl, and extracted with methylene chloride three times. The combined organic layers are washed with a saturated sodium chloride solution, dried with magnesium sulfate, and concentrated in vacuo. Purification by silica gel chromatography (ethyl acetate/hexane: 1:9) followed by recrystallization (methylene chloride-hexane) provides 1.8 g (54% yield) of the title compound as a white solid. $^1$H NMR (CDCl$_3$): δ 8.41 (m, 1H), 8.20 (m, 1H), 7.82 (d, J=15 Hz, 2H), 7.50 (t, 1H), 7.08 (d, J=15 Hz, 2H), 3.95 (s, 3H).

2-Fluoro-5-(4-methoxy-benzoyl)-benzenesulfonamide

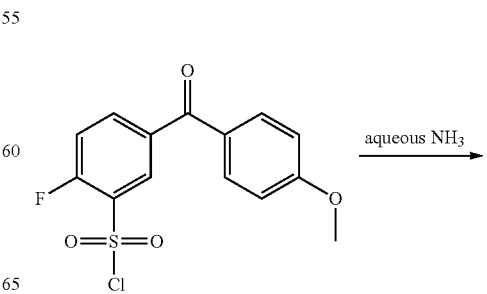

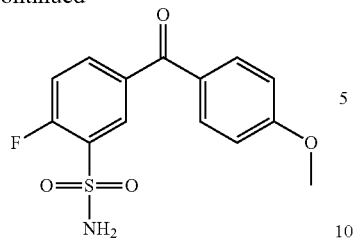

To a solution of 2-fluoro-5-(4-methoxy-benzoyl)-benzenesulfonyl chloride (0.45 g, 1.0 mmol) in methylene chloride is added aqueous ammonium solution (1 mL). The reaction mixture is stirred for 10 min at room temperature. The solvent is removed and the residue is redissolved in ethyl acetate and extracted with water. The organic layers are washed with a saturated sodium chloride solution, dried with magnesium sulfate, and concentrated in vacuo. The residue is recrystallized with methylene chloride-hexane to give 100 mg (32% yield) of the title compound as pale yellow solid. $^1$H NMR (CDCl$_3$): δ 8.40 (m, 1H), 8.05 (m, 1H), 7.80 (d, J=8 Hz, 2H), 7.32 (t, 1H), 7.00 (d, J=8 Hz, 2H), 5.15 (s, 1H), 3.90 (s, 3H). Analytics calculated for C$_{14}$H$_{12}$FNO$_4$S: C, 54.36; H, 3.91; N, 4.53. Found: C, 53.89; H, 3.50; N, 4.50.

Example 3

2-Chloro-5-(4-methoxy-benzoyl)-benzenesulfonamide

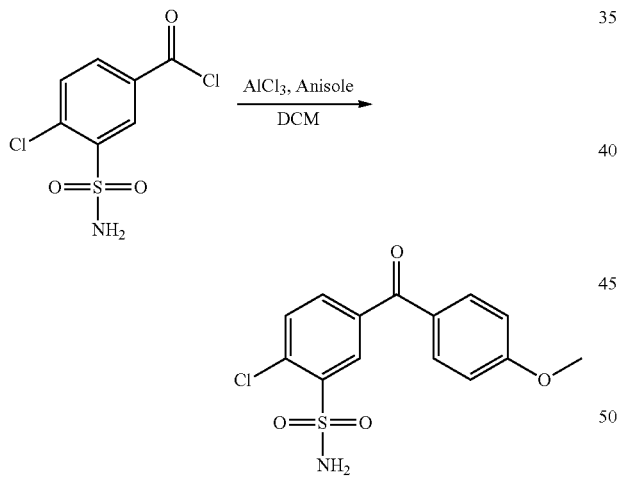

2-Chloro-5-(4-methoxy-benzoyl)-benzenesulfonamide

Under nitrogen, aluminum chloride (1.95 g, 14.6 mmol) is slurried in dichloromethane (50 mL) then 4-chloro-3-sulfamoyl benzoyl chloride is added and allowed to stir at ambient temperature for 30 minutes. Anisole (683 mg, 6.3 mmol) is added in 2 mL methylene chloride. The reaction is allowed to stir at ambient temperature for 18 hours. The reaction mixture is poured over ice-cold 6 N HCl and extracted with dichloromethane to give a colorless oil. Purification by silica gel chromatography (gradient of ethyl acetate in hexanes 5-25%) yielded a white foam which is crystallized three times from ether to afford the title compound. $^1$H NMR (MeOD) δ 3.9 (s, 3H), 7.1 (d, 2H, J=8.84 Hz), 7.7-8.0 (m, 4H), 8.4 (d, 1H, J=1.96 Hz). MS (m/z): 326 (M+1). CHN Calc C, 51.62; H, 3.71; N, 4.3. Found C, 51.70; H, 3.76, N, 4.22. M.P. 156-158° C.

Example 4

2,3-Difluoro-5-(4-methoxy-benzoyl)-benzenesulfonamide

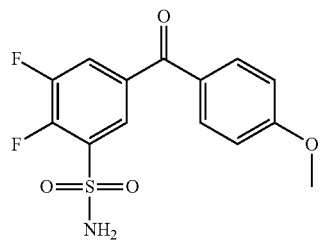 [SMILES: COc1ccc(C(=O)c2cc(F)c(F)c(S(N)(=O)=O)c2)cc1]

2,3-Difluoro-5-(4-methoxy-benzoyl)-benzenesulfonamide is prepared as described above for 2-fluoro-5-(4-methoxy-benzoyl)-benzenesulfonamide. $^1$H NMR (CDCl$_3$): δ 8.0 (m, 1H), 7.88 (m, 1H), 7.80 (d, J=15 Hz, 2H), 7.00 (d, J=15 Hz, 2H), 5.30 (s, 2H), 3.92 (s, 3H). Analytics calculated for C$_{14}$H$_{11}$F$_2$NO$_4$S: C, 51.38; H, 3.39; N, 4.28. Found: C, 51.98; H, 3.76; N, 3.86. MS (m/z): 326 (M−1).

Example 5

5-(4-Methoxy-benzoyl)-2-nitro-benzenesulfonamide

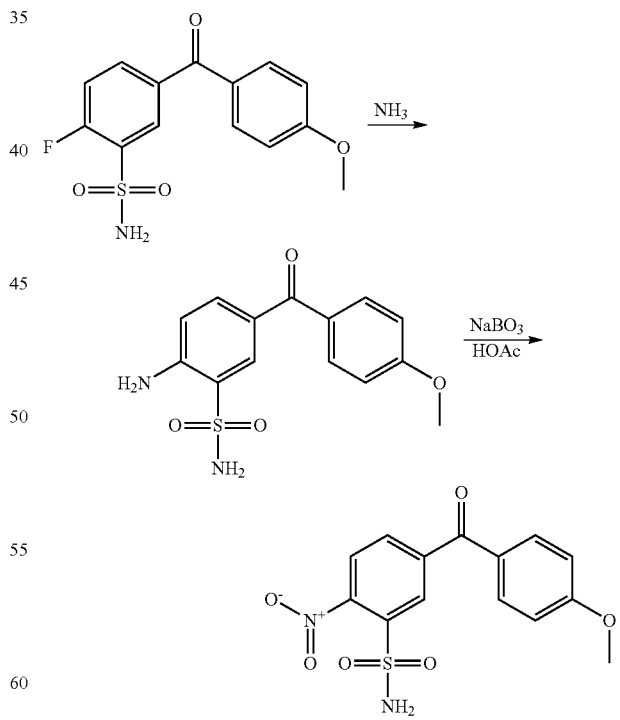

2-Amino-5-(4-methoxy-benzoyl)-benzenesulfinamide

To a solution of 2-fluoro-5-(4-methoxy-benzoyl)-benzenesulfonamide (0.25 g, 0.81 mmol) dissolved in dioxane (3 mL)

is added aqueous ammonia solution (1 mL). The reaction mixture is heated at 100° C. for 6 h in sealed tube and then cooled to room temperature and concentrated in vacuo. The residue is partitioned between water and ethyl acetate, and the aqueous phase is extracted with ethyl acetate three times. The combined organic extracts are washed with a saturated sodium chloride solution, dried with magnesium sulfate, and concentrated in vacuo to provide 0.2 g (81%) of the title compound as a pale yellow solid. $^1$H NMR (DMSO): δ 8.05 (d, J=2 Hz, 1H), 7.70 (m, 3H), 7.40 (s, 2H), 7.05 (d, J=9 Hz, 2H), 6.92 (d, J=9 Hz, 1H), 3.88 (s, 3H).

5-(4-Methoxy-benzoyl)-2-nitro-benzenesulfonamide

To a solution of 2-amino-5-(4-methoxy-benzoyl)-benzenesulfinamide (0.15 g, 0.49 mmol) dissolved in acetic acid (2 mL) is added NaBO$_3$.water (0.215 g, 2.16 mmol). The reaction mixture is heated at 50° C. for 7 h and then cooled to room temperature. Sodium hydroxide (solid) is added to neutralize the mixture, and the solution is then extracted with methylene chloride three times. The combined organic extracts are washed with a saturated sodium chloride solution, dried with magnesium sulfate, and concentrated in vacuo. The resulting residue is dissolved in dioxane, followed by the addition of 1 N of sodium hydroxide solution (2 mL). After stirring at 50° C. for 1 h, the mixture is cooled to room temperature and concentrated in vacuo. The residue is partitioned between water and methylene chloride, and the aqueous phase is extracted with methylene chloride three times. The combined organic extracts are washed with a saturated sodium chloride solution, dried with magnesium sulfate, and concentrated in vacuo. Purification by silica gel chromatography (50% ethyl acetate-hexane) followed by recrystallization (methylene chloride-hexane) provides 0.038 g (28%) of the title compound as a pale yellow solid. $^1$H NMR (CDCl$_3$): δ 8.50 (d, J=1 Hz, 1H), 8.05 (m, 2H), 7.80 (d, J=8 Hz, 2H), 7.00 (d, J=8 Hz, 2H), 5.50 (s, 1H), 3.90 (s, 3H). Analytics calculated for C$_{14}$H$_{12}$N$_2$O$_6$S: C, 50.00; H, 3.60; N, 8.33. Found: C, 49.99; H, 3.41; N, 7.96. MS (m/z): 335 (M−1).

Example 6

5-(4-Methoxy-benzoyl)-2-methyl-benzenesulfonamide

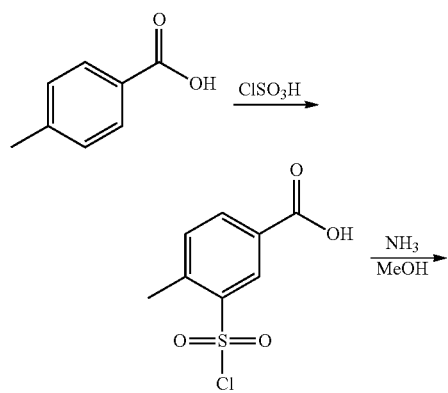

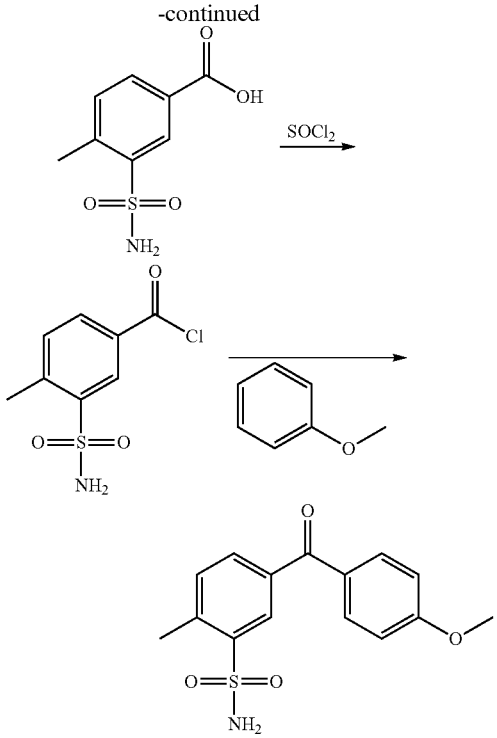

3-Chlorosulfonyl-4-methyl-benzoic acid

Sodium chloride (8 g, 138 mmol) is added to chlorosulfonic acid (30 mL, 451 mmol) and in small portions 4-methyl-benzoic acid (4 g, 29 mmol) is added to the stirred mixture. After complete addition, the reaction is heated at 122° C. for 16 h. The reaction mixture is cooled and poured into ice-water. The organic material is extracted with ethyl acetate. The organic layer is washed with a saturated sodium chloride solution, dried over magnesium sulfate, filtered, and the solvent is removed in vacuo. The residue is used as is in the next step.

4-Methyl-3-sulfamoyl-benzoic acid

A solution of ammonia in methanol (40 mL, 2 M) is added to the crude 3-chlorosulfonyl-4-methyl-benzoic acid and the solution stirred at room temperature for 16 hours. The volume is reduced by 50% by heating under reduced pressure, the solution is filtered to remove the precipitate and the precipitate washed with additional methanol. The sulphonamide precipitate is used directly in the next step.

4-methyl-3-sulfamoyl-benzoyl chloride

4-Methyl-3-sulfamoyl-benzoic acid (2 g, 10 mmol) is added to thionyl chloride (15 mL) and heated at reflux for 3 hours. Hexanes are added to the cooled solution and an oil forms. The hexanes are decanted and the oil is dissolved in methylene chloride and washed with hexanes. The solvent is removed under reduced pressure and the crude oil used in the next step.

5-(4-Methoxy-benzoyl)-2-methyl-benzenesulfonamide

To a suspension of aluminium chloride (906 mg, 6.8 mmol) in methylene chloride (20 mL) is added 4-methyl-3-sulfamoyl-benzoyl chloride (1.1 g, 4.7 mmol) and anisole (1.1 g, 10.2 mmol). After the mixture is stirred at room temperature for 16 h, the reaction is quenched with 6 N HCl, and extracted with methylene chloride three times. The combined organic layers are washed with a saturated sodium chloride solution, dried with magnesium sulfate, and concentrated in vacuo. On standing, crystals form and trituration with diethyl ether and ethyl acetate provides 0.84 g (58% yield) of the title compound as a white solid. MS (m/z): 306 (M+1).

Example 7

5-(4-Methoxy-benzoyl)-2-methylsulfanyl-benzenesulfonamide

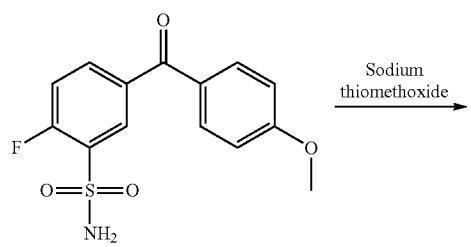

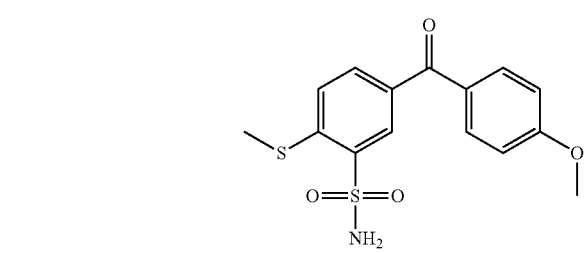

To a solution of 2-fluoro-5-(4-methoxy-benzoyl)-benzenesulfonamide (0.15 g, 0.48 mmol) dissolved in dioxane (3 mL) is added sodium thiomethoxide (0.041 g, 0.57 mmol). The reaction mixture is heated at 90° C. for 4 h and then cooled to room temperature and concentrated in vacuo. The residue is partitioned between water and methylene chloride, and the aqueous phase is extracted with methylene chloride three times. The combined organic extracts are washed with a saturated sodium chloride solution, dried with magnesium sulfate, and concentrated in vacuo. Purification by silica gel chromatography (50% ethyl acetate-hexane) gives 0.11 g (68%) of the title compound as a white solid. $^1$H NMR (CDCl$_3$): δ 8.4 (d, J=2 Hz, 1H), 7.90 (dd, J=8, 2 Hz, 1H), 7.80 (d, J=9 Hz, 2H), 7.50 (d, J=8 Hz, 1H), 7.00 (d, J=9 Hz, 2H), 5.20 (s, 2H), 3.90 (s, 3H), 2.65 (s, 3H). Analytics calculated for C$_{15}$H$_{15}$NO$_4$S$_2$: C, 53.04; H, 4.48; N, 4.15. Found: C, 52.67; H, 4.57; N, 4.08. MS (m/z): 336 (M–1).

Example 8

2-Methanesulfinyl-5-(4-methoxy-benzoyl)-benzenesulfonamide

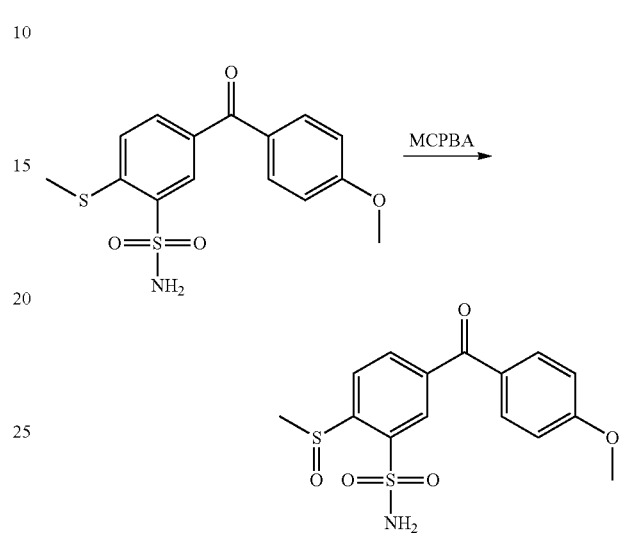

To a solution of 5-(4-methoxy-benzoyl)-2-methylsulfanyl-benzenesulfonamide (0.06 g, 0.18 mmol) dissolved in methylene chloride (3 mL) at 0° C. is added m-chloroperoxybenzoic acid (0.061 g, 0.36 mmol). The reaction mixture is stirred at room temperature for 30 minutes Then, the reaction is quenched with saturated sodium sulfite and sodium bicarbonate solution. The aqueous layer is extracted with methylene chloride three times. The combined organic extracts are washed with a saturated sodium chloride solution, dried with magnesium sulfate, and concentrated in vacuo. Purification by silica gel chromatography (75% ethyl acetate-hexane) followed by recrystallization (methylene chloride-hexane) provides 0.022 g (35%) of the title compound as a pale yellow solid. $^1$H NMR (CDCl$_3$): δ 8.35 (d, J=8 Hz, 1H), 8.10 (dd, J=8, 1 Hz, 1H), 7.80 (d, J=9 Hz, 2H), 7.00 (d, J=9 Hz, 2H), 5.60 (s, 2H), 3.95 (s, 3H), 3.00 (s, 3H). Analytics calculated for C$_{15}$H$_{15}$NO$_5$S$_2$: C, 50.98; H, 4.28; N, 3.96. Found: C, 50.17; H, 4.46; N, 3.40. MS (m/z): 352 (M–1).

Example 9

2-Methanesulfonyl-5-(4-methoxy-benzoyl)-benzenesulfonamide

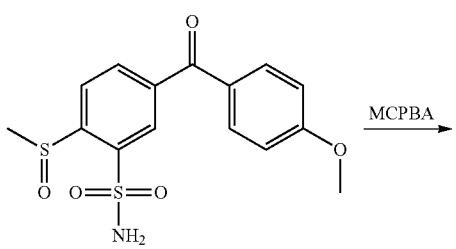

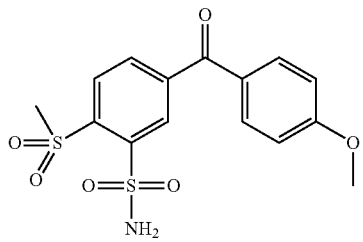

To a solution of 5-(4-methoxy-benzoyl)-2-methylsulfanyl-benzenesulfonamide (0.12 g, 0.36 mmol) dissolved in methylene chloride (3 mL) at 0° C. is added m-chloroperoxybenzoic acid (0.153 g, 0.90 mmol). The reaction mixture is stirred at room temperature for 2 h. Then, the reaction is quenched with saturated sodium sulfite and sodium bicarbonate solution. The aqueous layer is extracted with methylene chloride three times. The combined organic extracts are washed with a saturated sodium chloride solution, dried with magnesium sulfate, and concentrated in vacuo. Purification by silica gel chromatography (75% ethyl acetate-hexane) followed by recrystallization (methylene chloride-hexane) provides 0.038 g (28%) of the title compound as a pale yellow solid. $^1$H NMR (CDCl$_3$): δ 8.55 (d, J=1 Hz, 1H), 8.40 (d, J=8 Hz, 1H), 8.10 (dd, J=8, 1 Hz, 1H), 7.80 (d, J=8 Hz, 2H), 7.00 (d, J=8 Hz, 2H), 5.80 (s, 2H), 3.95 (s, 3H), 3.44 (s, 3H). Analytics calculated for $C_{15}H_{15}NO_6S_2$: C, 48.77; H, 4.09; N, 3.79. Found: C, 48.51; H, 4.16; N, 3.40. MS (m/z): 368 (M−1).

Example 10

2-Chloro-5-(4-methoxy-benzoyl)-N-phenethyl-benzenesulfonamide

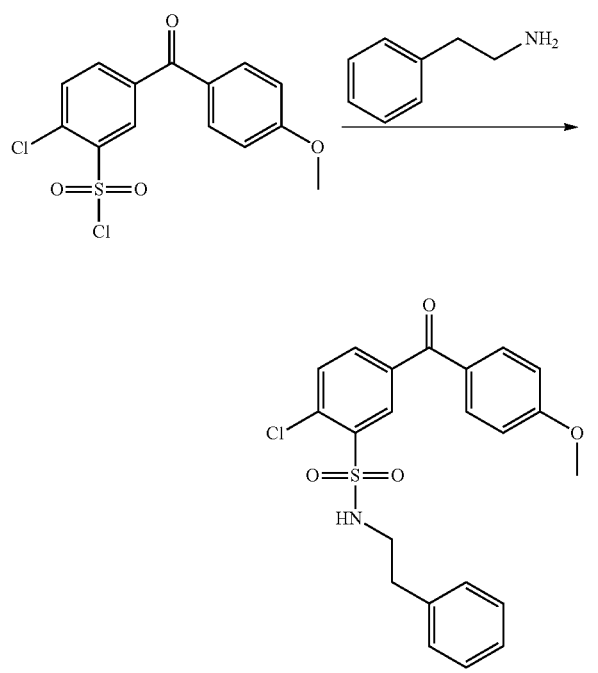

2-Chloro-5-(4-methoxy-benzoyl)-benzenesulfonyl chloride

The title compound is prepared as described above for 2-fluoro-5-(4-methoxy-benzoyl)-benzenesulfonyl chloride, starting with 4-chloro-benzoic acid.

2-Chloro-5-(4-methoxy-benzoyl)-N-phenethyl-benzenesulfonamide

2-Chloro-5-(4-methoxy-benzoyl)-benzenesulfonyl chloride (0.2 g, 5.79 mmol) is dissolved in methylene chloride (10 mL). Phenethylamine (0.077 g, 6.36 mmol) is added, followed by the addition of triethylamine (0.146 g, 14.5 mmol). The reaction mixture is stirred for 2 h at room temperature. Water is added, and the mixture extracted with methylene chloride. The solvent is removed and the mixture is purified by flash column chromatography, using 50% of ethyl acetate-hexane as an eluent. The product is obtained as a colorless oil (0.13 g, 52% yield). $^1$H NMR (CDCl$_3$): δ 8.4 (m, 1H), 7.90 (m, 1H), 7.50 (d, J=8 Hz, 2H), 7.28 (m, 3H), 7.00 (d, J=8 Hz, 2H), 7.17 (m, 2H), 4.97 (m, 1H), 3.91 (s, 3H), 3.20 (m, 2H), 2.80 (m, 2H). Analytics calculated for $C_{22}H_{20}ClNO_4S$: C, 61.46; H, 4.69; N, 3.26. Found: C, 61.20; H, 4.95; N, 3.10. MS (m/z): 430.0 (M+1).

Example 11

2-Chloro-N-[2-(4-fluoro-phenyl)-ethyl]-5-(4-methoxy-benzoyl)-benzenesulfonamide

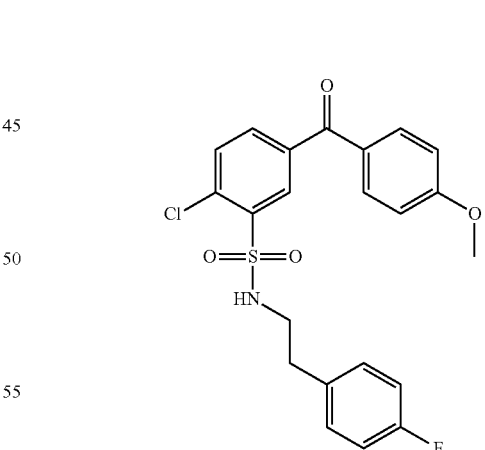

The title compound is prepared as described for 2-chloro-5-(4-methoxy-benzoyl)-N-phenethyl-benzenesulfonamide, except using 4-fluoro-phenethylamine. $^1$H NMR (CDCl$_3$): δ 8.4 (m, 1H), 7.90 (m, 1H), 7.80 (d, J=8 Hz, 2H), 7.60 (m, 1H), 7.08 (m, J=8 Hz, 2H), 7.00 (m, 3H), 4.97 (m, 1H), 3.91 (s, 3H), 3.20 (m, 2H), 2.80 (m, 2H). Analytics calculated for C$_{22}$H$_{19}$ClFNO$_4$S: C, 58.99; H, 4.28; N, 3.13. Found: C, 58.58; H, 4.33; N, 3.12. MS (m/z): 448.0 (M+1)⁻.

Example 12

2-Chloro-5-(3-hydroxy-4-methoxy-benzoyl)-benzenesulfonamide

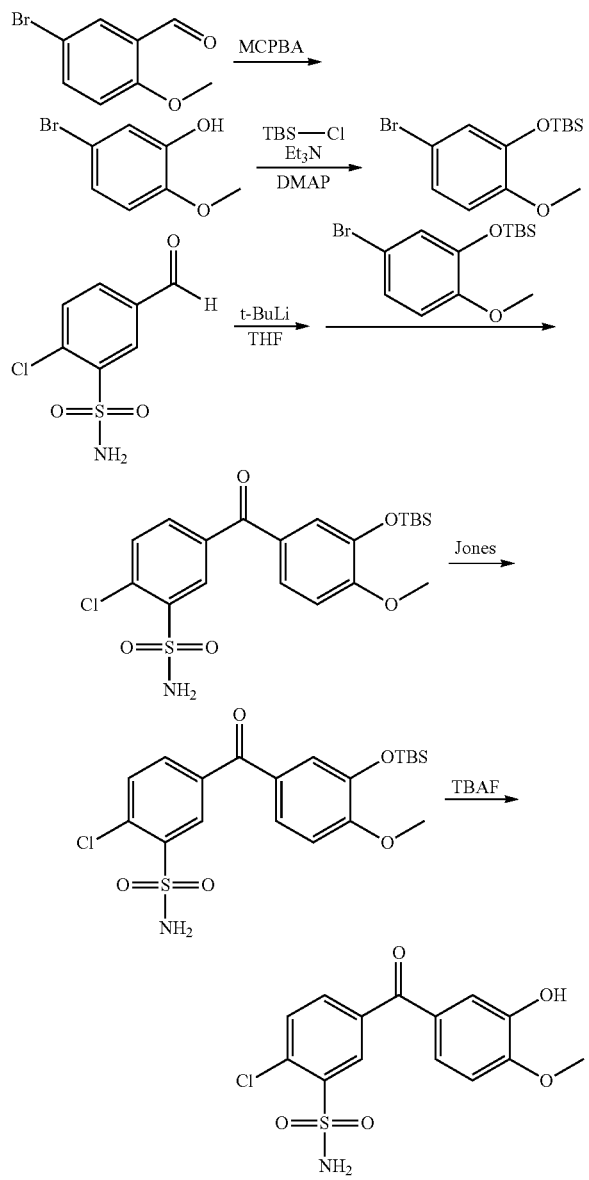

5-Bromo-2-methoxy-phenol

To a solution of 5-bromo-2-methoxy-benzaldehyde (8 g, 4.67 mmol) dissolved in methylene chloride (24 mL) at 0° C. is slowly added a solution of m-chloroperoxybenzoic acid (10.90 g, 5.60 mmol) in methylene chloride (80 mL). The reaction mixture is slowly warmed up to room temperature and stirred for 72 h. The white solid is filtered off and the filtrate is stirred for 2 h with 2 M sodium sulfite (32 mL). The organic layer is concentrated in vacuo then the residue is dissolved in diethyl ether and washed with 1 M sodium sulfite and a half-saturated sodium bicarbonate solution. The organic phase is extracted with 2 M sodium hydroxide. The combined basic extract is acidified to pH 3-4 with concentrated HCl, and extracted with diethyl ether. The combined organic extracts are washed with a saturated sodium chloride solution, dried with magnesium sulfate, and concentrated in vacuo to provide 3.5 g (37%) of the title compound as a brown solid. ¹H NMR (CDCl$_3$): δ 7.10 (d, J=2 Hz, 1H), 7.00 (dd, J=8, 2 Hz, 1H), 6.70 (d, J=8 Hz, 1H), 3.95 (s, 3H).

(5-Bromo-2-methoxy-phenoxy)-tert-butyl-dimethyl-silane

To a solution of 5-bromo-2-methoxy-phenol (3.5 g, 17.2 mmol) dissolved in methylene chloride (50 mL) are added triethylamine (2.08 g, 20.6 mmol) and 4-dimethylaminopyridine (0.15 g, 0.86 mmol). Then tert-butyldimethylsilyl chloride is added slowly and the reaction mixture is stirred at room temperature for 16 h. The reaction is quenched with 10% of citric acid, and then the organic layer is washed with saturated sodium bicarbonate solution, a saturated sodium chloride solution, dried with magnesium sulfate, and concentrated in vacuo. Purification by silica gel chromatography (15% ethyl acetate-hexane) provides 5.6 g (100%) of the title compound as a colorless oil. ¹H NMR (CDCl$_3$): δ 6.82 (m, 2H), 6.58 (d, J=9 Hz, 1H), 3.74 (s, 3H), 0.95 (s, 9H), 0.05 (s, 6H).

5-{[3-(tert-butyl-dimethyl-silanyloxy)-4-methoxy-phenyl]-hydroxy-methyl}-2-chloro-benzenesulfonamide To a solution of (5-bromo-2-methoxy-phenoxy)-tert-butyl-dimethyl-silane (2 g, 6.32 mmol) dissolved in tetrahydrofuran (25 mL) at −78° C. under nitrogen is dropwisely added 1.7 M of tert-butyllithium (8.06 mL, 12.6 mmol). The reaction mixture is stirred at −78° C. for 5 minutes Then, the solution of 2-chloro-5-formyl-benzenesulfonamide (0.462 g, 2.11 mmol) in tetrahydrofuran (5 mL) is added slowly. The reaction mixture is warmed up to room temperature and stirred for 24 h. The reaction is quenched with 1 N of HCl, and extracted with ethyl acetate three times. The combined organic extracts are washed with a saturated sodium chloride solution, dried with magnesium sulfate, and concentrated in vacuo. Purification by silica gel chromatography (50% ethyl acetate-hexane) provides 0.57 g (59%) of the title compound as a brown oil. ¹H NMR (CDCl$_3$): δ 8.00 (m, 1H), 7.40 (m, 2H), 6.70 (d, 3H), 5.70 (s, 1H), 5.00 (m, 2H), 3.70 (s, 3H), 0.90 (s, 9H), 0.05 (s, 6H).

5-[3-(tert-Butyl-dimethyl-silanyloxy)-4-methoxy-benzoyl]-2-chloro-benzenesulfonamide To a solution of 5-{[3-(tert-butyl-dimethyl-silanyloxy)-4-methoxy-phenyl]-hydroxy-methyl}-2-chloro-benzenesulfonamide (0.57 g, 1.24 mmol) dissolved in acetone (100 mL) is added Jones reagent (3 M, 0.4 mL), and the reaction mixture is stirred at room temperature for 15 minutes The reaction is quenched with water, and the aqueous layer is extracted with methylene chloride three times. The combined organic extracts are washed with saturated sodium bicarbonate solution, a saturated sodium chloride solution, dried with magnesium sulfate, and concentrated in vacuo. Recrystallization from methylene chloride/hexane provides 0.28 g (50%) of the title compound as a grey solid. ¹H NMR (CDCl$_3$): δ 8.23 (d, J=2 Hz, 1H), 7.80 (dd, J=8, 2 Hz, 1H), 7.50 (d, J=8 Hz, 1H), 7.20 (m, 2H), 6.70 (d, J=8 Hz, 1H), 5.00 (s, 2H), 3.70 (s, 3H), 0.90 (s, 9H), 0.05 (s, 6H).

2-Chloro-5-(3-hydroxy-4-methoxy-benzoyl)-benzenesulfonamide

To a solution of 5-[3-(tert-butyl-dimethyl-silanyloxy)-4-methoxy-benzoyl]-2-chloro-benzenesulfonamide (0.28 g, 0.61 mmol) dissolved in tetrahydrofuran (20 mL) is added 1 M tetrabutylammonium fluoride (1.23 mL, 1.22 mmol) in tetrahydrofuran. The reaction mixture is stirred at room temperature for 30 minutes The reaction is quenched with 1 N of HCl, and extracted with ethyl acetate three times. The combined organic extracts are washed with a saturated sodium chloride solution, dried with magnesium sulfate, and concentrated in vacuo. Recrystallization from ethyl acetate/methylene chloride provides 0.11 g (49%) of the title compound as a brown solid. $^1$H NMR (DMSO): δ 9.60 (s, 1H), 8.20 (d, J=2 Hz, 1H), 7.80 (m, 4H), 7.20 (m, 2H), 7.10 (d, J=8 Hz, 1H), 3.90 (s, 3H). Analytics calculated for $C_{14}H_{12}ClNO_5S$: C, 49.20; H, 3.54; N, 4.10. Found: C, 49.90; H, 3.30; N, 5.06. MS (m/z): 342 (M+1).

Example 13

2-Chloro-5-[4-(2-hydroxy-ethoxy)-benzoyl]-benzenesulfonamide

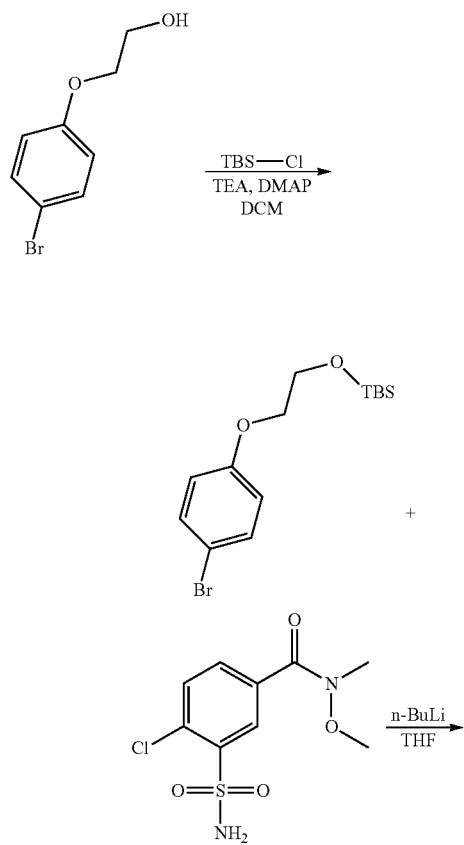

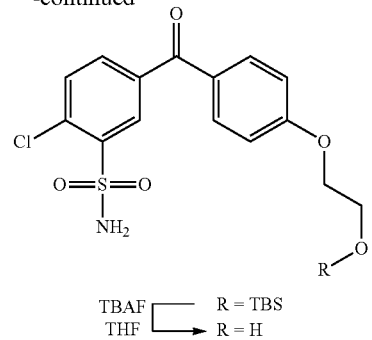

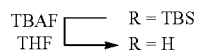

[2-(4-Bromo-phenoxy)-ethoxy]-tert-butyl-dimethyl-silane 2-(4-Bromo-phenoxy)-ethanol (5 g, 23 mmol) is dissolved in dichloromethane (40 mL). Triethylamine (2.8 g, 28 mmol) and 4-dimethylaminopyridine (140 mg, 1.15 mmol) were then added followed by tert-butyldimethylsilyl chloride (3.65 g, 24.3 mmol) as a solution in dichloromethane (10 mL). The reaction is allowed to stir at ambient temperature for 18 hours. The reaction mixture is washed with 10% aqueous citric acid, the organic layer is separated and concentrated in vacuo to afford 7.5 g (98% yield) of the title compound. $^1$H NMR (CDCl$_3$) δ 0.05 (s, 6H), 0.85 (s, 9H), 3.85-3.94 (m, 4H), 6.72 (d, 2H, J=6.90 Hz), 7.28 (d, 2H, J=6.90 Hz).

5-{4-[2-(tert-Butyl-dimethyl-silanyloxy)-ethoxy]-benzoyl}-2-chloro-benzenesulfonamide

[2-(4-Bromo-phenoxy)-ethoxy]tert-butyl-dimethyl-silane (7.3 g, 22.12 mmol) is dissolved in tetrahydrofuran (120 mL) and cooled to −78° C. The solution is treated with a solution of n-butyllithium (1.6 M in hexanes, 13.8 mL, 22.12 mmol) and stirred 30 minutes after which a solution of 4-chloro-N-methoxy-N-methyl-3-sulfamoyl-benzamide (2.05 g, 7.37 mmol) in tetrahydrofuran (20 mL) is added. The reaction is allowed to stir for 18 hours while warming to ambient temperature. The reaction is quenched with a saturated solution of ammonium chloride and extracted twice with ether. The organic phase is separated and concentrated in vacuo. The residue is purified by column chromatography (gradient of ethyl acetate in hexanes 10-50%) affording 1.84 g (53% yield) of the title compound. MS (m/z): 470.2 (M+1).

2-Chloro-5-[4-(2-hydroxy-ethoxy)-benzoyl]-benzenesulfonamide

5-{4-[2-(tert-Butyl-dimethyl-silanyloxy)-ethoxy]-benzoyl}-2-chloro-benzenesulfonamide (1.84 g, 3.92 mmol) is dissolved in tetrahydrofuran (50 mL), and treated with a solution of tetrabutylammonium fluoride reagent (1 M in tetrahydrofuran, 2.2 mmol). The reaction is allowed to stir for 1 hour. The reaction is diluted with water and extracted with ether. The organic phase is separated and concentrated in vacuo affording 1.39 g (100% yield) of the title compound.

$^1$H NMR (DMSO) δ 3.75 (t, 2H, J=4.55 Hz), 4.12 (t, 2H, J=4.80 Hz), 4.95 (s, 2H), 7.12 (d, 2H, J=8.84 Hz), 7.76-7.90 (m, 4H), 8.24 (d, 1H, J=2.02). MS (m/z): 354 (M−1).

Example 14

2-Chloro-5-(4-butoxy-benzoyl)-benzenesulfonamide

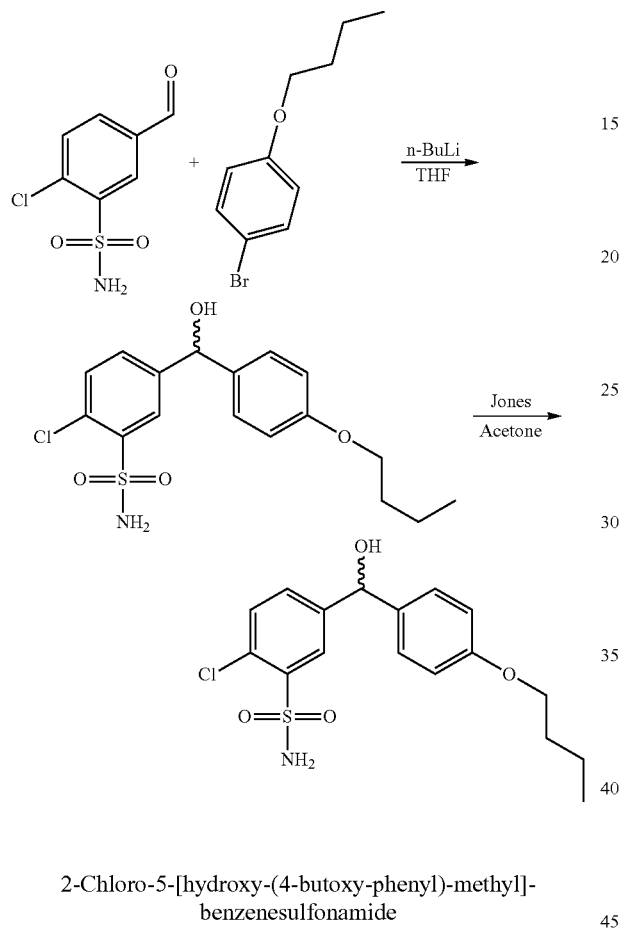

2-Chloro-5-[hydroxy-(4-butoxy-phenyl)-methyl]-benzenesulfonamide

1-Bromo-4-butoxy-benzene (625 mg, 2.73 mmol) is dissolved in tetrahydrofuran (2 mL) and cooled to −78° C. The solution is treated with a solution of n-butyllithium (1.6 M in hexanes, 1.7 mL, 2.73 mmol) which resulted in precipitation of the aryllithium. The suspension is allowed to warm to ambient temperature and is added via canula to a solution of 2-chloro-5-formyl-benzenesulfonamide (200 mg, 0.91 mmol) in tetrahydrofuran (2 mL) at −78° C. The reaction is allowed to warm to ambient temperature, at which point it is quenched with a saturated solution of ammonium chloride. The tetrahydrofuran is removed in vacuo and the residue is diluted with water and extracted with ethyl acetate. The organic phase is separated and concentrated in vacuo. The residue is used without further purification.

2-Chloro-5-(4-butoxy-benzoyl)-benzenesulfonamide

2-Chloro-5-[hydroxy-(4-butoxy-phenyl)-methyl]-benzenesulfonamide is dissolved in acetone (10 mL), and treated with a solution of Jones reagent (3 M in water, 0.91 mmol). The reaction is allowed to stir for 30 minutes. The reaction is diluted with water and extracted with dichloromethane. The organic phase is separated and concentrated in vacuo. The residue is purified by silica gel chromatography (gradient of ethyl acetate in hexanes 10-50%) affording 74 mg of the title compound. $^1$H NMR (CDCl$_3$) δ 0.95 (t, 3H, J=7.31 Hz), 1.50 (m, 2H), 1.80 (m, 2H), 4.05 (t, 2H, J=6.48 Hz), 5.15 (s, 2H), 6.95 (d, 2H, J=9.04 Hz), 7.65 (d, 1H, J=8.22), 7.80 (d, 2H, J=9.04 Hz), 7.90 (dd, 1 h, J=1.88, 7.91), 8.45 (d, 1H, J=1.88). MS (m/z): 368 (M+1). CHN Calc C, 55.51; H, 4.93; N, 3.81. Found C, 55.47; H, 4.84; N, 3.63.

Example 15

2-Chloro-5-(4-isobutoxy-benzoyl)-benzenesulfonamide

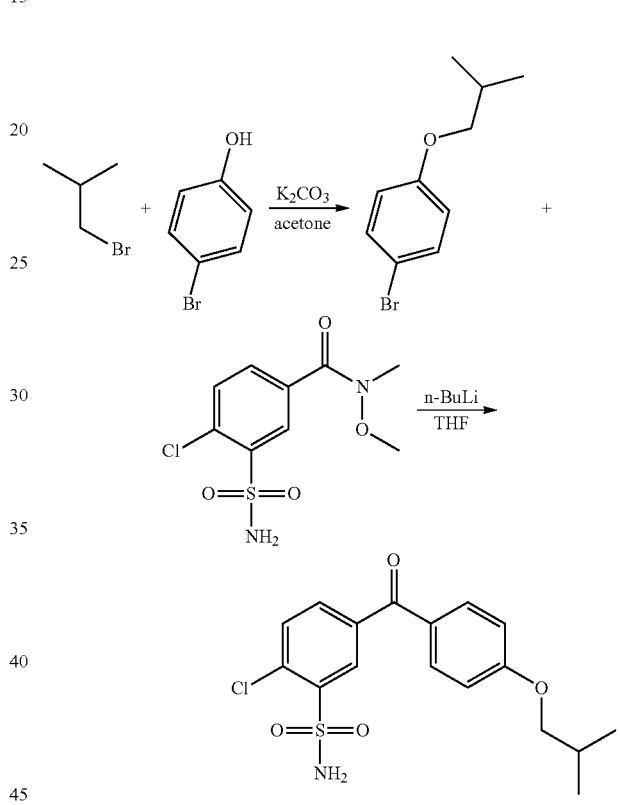

1-Bromo-4-isobutoxy-benzene

4-Bromo-phenol (2 g, 11.6 mmol) is dissolved in acetone (40 mL). Potassium carbonate (8 g, 38.4 mmol) is then added followed by isobutyl bromide (4 g, 29.2 mmol). The reaction is heated to reflux for four days, refilling solvent as necessary. The reaction mixture is diluted with water and extracted with ether, the organic layer is separated and concentrated in vacuo. The residue is dissolved in hexane dried with magnesium sulfate, and filtered through a plug of silica gel. The solvent is removed in vacuo to afford 1.6 g (60% yield) of the title compound as a colorless non-viscous oil. $^1$H NMR (CDCl$_3$) δ 1.01 (d, 6H, J=6.56 Hz), 2.05-2.08 (m, 1H), 3.67 (d, 2H, J=6.57 Hz), 6.77 (d, 2H, J=9.09 Hz), 7.36 (d, 2H, J=9.09 Hz).

2-Chloro-5-(4-isobutoxy-benzoyl)-benzenesulfonamide

1-Bromo-4-isobutoxy-benzene (625 mg, 2.73 mmol) is dissolved in tetrahydrofuran (2 mL) and cooled to −78° C.

The solution is treated with a solution of n-butyllithium (1.6 M in hexanes, 1.7 mL, 2.73 mmol) and stirred 30 minutes after which a solution of 4-chloro-N-methoxy-N-methyl-3-sulfamoyl-benzamide (250 mg, 0.91 mmol) in tetrahydrofuran (2 mL) is added. The reaction is allowed to stir for 18 hours while warming to ambient temperature. The reaction is quenched with a saturated solution of ammonium chloride and extracted with ethyl acetate. The organic phase is separated and concentrated in vacuo. The residue is purified by column chromatography (gradient of ethyl acetate in hexanes 10-50%) affording 120 mg (37% yield) of the title compound. $^1$H NMR (DMSO) δ 1.00 (d, 6H, J=6.56 Hz), 2.01-2.10 (m, 1H), 3.88 (d, 2H, J=6.57 Hz), 7.11 (d, 2H, J=8.85 Hz), 7.76 (d, 2H, J=8.85 Hz), 7.81-7.84 (m, 3H), 7.89 (dd, 1H, J=2.02, 8.08), 8.24 (d, 1H, J=2.02). MS (m/z): 366 (M−1). CHN Calc C, 55.51; H, 4.93; N, 3.81. Found C, 55.38; H, 4.74; N, 3.77.

Example 16

2-Chloro-5-[4-(3-methyl-butoxy)-benzoyl]-benzene-sulfonamide

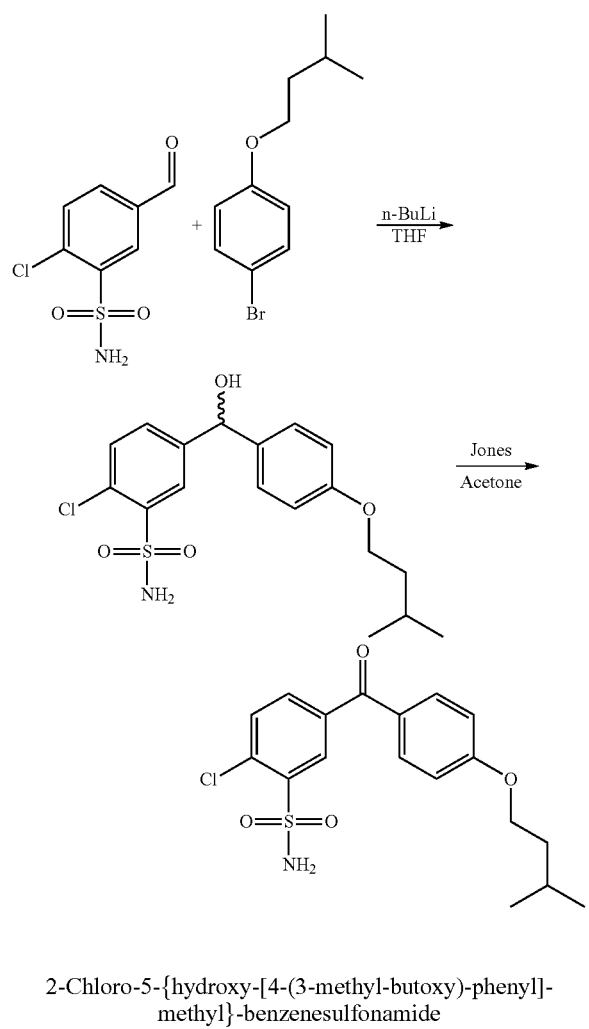

2-Chloro-5-{hydroxy-[4-(3-methyl-butoxy)-phenyl]-methyl}-benzenesulfonamide

1-Bromo-4-(3-methyl-butoxy)-benzene (665 mg, 2.73 mmol) is dissolved in tetrahydrofuran (2 mL) and cooled to −78° C. The solution is treated with a solution of n-butyllithium (1.6 M in hexanes, 1.7 mL, 2.73 mmol) which resulted in precipitation of the aryllithium. The suspension is allowed to warm to ambient temperature and is added via canula to a solution of 2-chloro-5-formyl-benzenesulfonamide (200 mg, 0.91 mmol) in tetrahydrofuran (2 mL) at −78° C. The reaction is allowed to warm to ambient temperature, at which point it is quenched with a saturated solution of ammonium chloride. The tetrahydrofuran is removed in vacuo and the residue is diluted with water and extracted with ethyl acetate. The organic phase is separated and concentrated in vacuo. The residue is used without further purification.

2-Chloro-5-[4-(3-methyl-butoxy)-benzoyl]-benzene-sulfonamide

2-Chloro-5-{hydroxy-[4-(3-methyl-butoxy)-phenyl]-methyl}-benzenesulfonamide is dissolved in acetone (10 mL), and treated with a solution of Jones reagent (3 M in water, 0.91 mmol). The reaction is allowed to stir for 30 minutes. The reaction is diluted with water and extracted with dichloromethane. The organic phase is separated and concentrated in vacuo. The residue is purified by silica gel chromatography (gradient of ethyl acetate in hexanes 25-75%) followed by recrystallization from ether affording 25 mg of the title compound. $^1$H NMR (DMSO) δ 0.93 (s, 3H), 0.95 (s, 3H), 1.64-1.82 (m, 3H), 4.13 (t, 2H, J=6.41 Hz), 7.12 (d, 2H, J=8.67 Hz), 7.75-7.91 (m, 4H), 8.24 (d, 1H, J=1.89). MS (m/z): 380 (M−1). CHN Calc C, 56.62; H, 5.28; N, 3.67. Found C, 56.54; H, 5.04; N, 3.73.

Example 17

2-Chloro-5-[4-(3-phenyl-propoxy)-benzoyl]-benzenesulfonamide

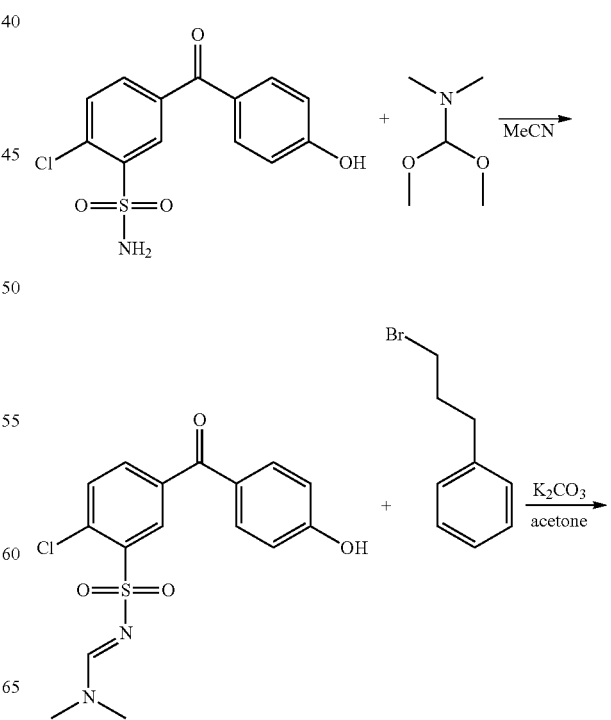

(t, 2H, J=6.41 Hz), 7.10 (d, 2H, J=8.67 Hz), 7.17-7.32 (m, 5H), 7.75-7.91 (m, 6H), 8.24 (d, 1H, J=1.88 Hz). MS (m/z): 430 (M+1).

Example 18

2-Chloro-5-(4-pentyloxy-benzoyl)-benzenesulfonamide

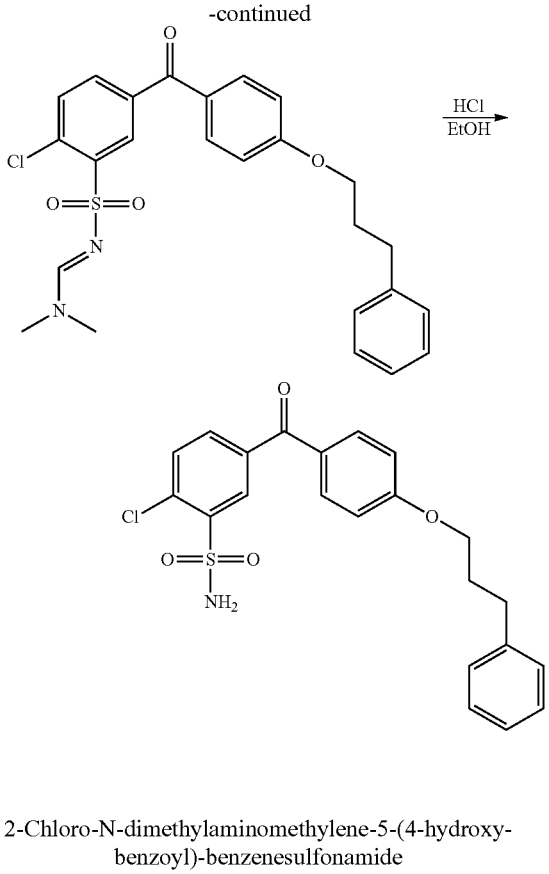

2-Chloro-N-dimethylaminomethylene-5-(4-hydroxy-benzoyl)-benzenesulfonamide

A solution of N,N,-dimethylformamide dimethyl acetal (1.2 g, 10.1 mmol) in acetonitrile (10 mL) is slowly added to a solution of 2-chloro-5-(4-hydroxy-benzoyl)-benzenesulfonamide (2.61 g, 8.4 mmol) in acetonitrile (10 mL). The reaction is allowed to stir for 5 hours at ambient temperature. Volatiles were removed in vacuo. The residue is partitioned between ethyl acetate and water, the organic layer is separated and the solvent is removed in vacuo, affording 2.5 g (81% yield) of the title compound which is carried on directly in the next step.

2-Chloro-5-[4-(3-phenyl-propoxy)-benzoyl]-benzenesulfonamide

2-Chloro-N-dimethylaminomethylene-5-(4-hydroxy-benzoyl)-benzenesulfonamide (250 mg, 0.68 mmol) is dissolved in N,N,-dimethylformamide (5 mL). Potassium carbonate (235 mg, 1.7 mmol) is then added followed by (3-bromopropyl)-benzene (135 mg, 0.68 mmol). The reaction is heated to 65° C. for 18 hours. The reaction mixture is diluted with water and extracted with ethyl acetate, the organic layer is separated and concentrated in vacuo. The crude ether is purified by column chromatography (gradient of ethyl acetate in hexanes 25-75%). The residue is dissolved in ethanol (3 mL), treated with concentrated HCl (400 µl) and heated to reflux for 2.5 hours after which the reaction is allowed to cool to ambient temperature overnight. The volatiles were removed in vacuo and the crude sulfonamide is purified by column chromatography (gradient of ethyl acetate in hexanes 20-70%) affording 10 mg of the title compound. $^1$H NMR (DMSO) δ 2.02-2.11 (m, 2H), 2.76 (t, 2H, J=7.16 Hz), 4.10

2-Chloro-5-[(4-pentyloxy-phenyl)-hydroxy-methyl]-benzenesulfonamide

1-Bromo-4-pentyloxy-benzene (656 mg, 2.73 mmol) is dissolved in tetrahydrofuran (2 mL) and cooled to −78° C. The solution is treated with a solution of n-butyllithium (1.6 M in hexanes, 1.7 mL, 2.73 mmol) which resulted in precipitation of the aryllithium. The suspension is allowed to warm to ambient temperature and is added via canula to a solution of 2-chloro-5-formyl-benzenesulfonamide (200 mg, 0.91 mmol) in tetrahydrofuran (2 mL) at −78° C. The reaction is allowed to warm to ambient temperature, at which point it is quenched with a saturated solution of ammonium chloride. The tetrahydrofuran is removed in vacuo and the residue is diluted with water and extracted with ethyl acetate. The organic phase is separated and concentrated in vacuo. The residue is used without further purification.

2-Chloro-5-(4-pentyloxy-benzoyl)-benzenesulfonamide

2-Chloro-5-[(4-pentyloxy-phenyl)-hydroxy-methyl]-benzenesulfonamide is dissolved in acetone (10 mL), and treated with a solution of Jones reagent (3 M in water, 0.91 mmol). The reaction is allowed to stir for 30 minutes. The reaction is diluted with water and extracted with dichloromethane. The organic phase is separated and concentrated in vacuo. The residue is purified by silica gel chromatography (gradient of ethyl acetate in hexanes 25-75%) followed by recrystallization from ether affording 15 mg of the title compound. $^1$H NMR (DMSO) $\delta$ 0.90 (t, 3H, J=6.79 Hz), 1.31-1.46 (m, 4H), 1.70-1.79 (m, 2H), 4.09 (t, 2H, J=6.49 Hz), 7.10 (d, 2H, J=9.04 Hz), 7.75-7.90 (m, 4H), 8.24 (d, 1H, J=1.89). MS (m/z): 382 (M+1).

Example 19

2-Chloro-5-(4-hexyloxy-benzoyl)-benzenesulfonamide

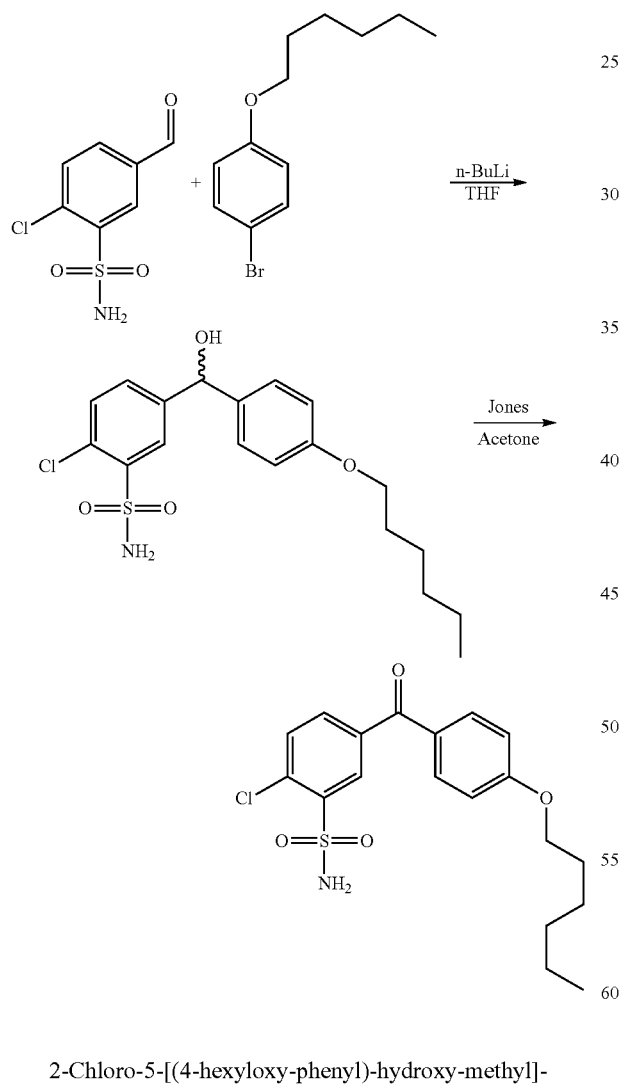

2-Chloro-5-[(4-hexyloxy-phenyl)-hydroxy-methyl]-benzenesulfonamide

1-Bromo-4-hexyloxy-benzene (695 mg, 2.73 mmol) is dissolved in tetrahydrofuran (2 mL) and cooled to −78° C. The solution is treated with a solution of n-butyllithium (1.6 M in hexanes, 1.7 mL, 2.73 mmol) which resulted in precipitation of the aryllithium. The suspension is allowed to warm to ambient temperature and is added via canula to a solution of 2-chloro-5-formyl-benzenesulfonamide (200 mg, 0.91 mmol) in tetrahydrofuran (2 mL) at −78° C. The reaction is allowed to warm to ambient temperature, at which point it is quenched with a saturated solution of ammonium chloride. The tetrahydrofuran is removed in vacuo and the residue is diluted with water and extracted with ethyl acetate. The organic phase is separated and concentrated in vacuo. The residue is used without further purification.

2-Chloro-5-(4-hexyloxy-benzoyl)-benzenesulfonamide

2-Chloro-5-[(4-hexyloxy-phenyl)-hydroxy-methyl]-benzenesulfonamide is dissolved in acetone (10 mL), and treated with a solution of Jones reagent (3 M in water, 0.91 mmol). The reaction is allowed to stir for 30 minutes. The reaction is diluted with water and extracted with dichloromethane. The organic phase is separated and concentrated in vacuo. The residue is purified by silica gel chromatography (gradient of ethyl acetate in hexanes 25-75%) followed by recrystallization from ether affording 30 mg of the title compound. $^1$H NMR (DMSO) $\delta$ 0.88 (t, 3H, J=6.78 Hz), 1.28-1.45 (m, 6H), 1.70-1.79 (m, 2H), 4.09 (t, 2H, J=6.4 Hz), 7.10 (d, 2H, J=9.04 Hz), 7.75-7.90 (m, 4H), 8.24 (d, 1H, J=1.89). MS (m/z): 396 (M+1).

Example 20

2-Chloro-5-(4-trifluoromethoxy-benzoyl)-benzenesulfonamide

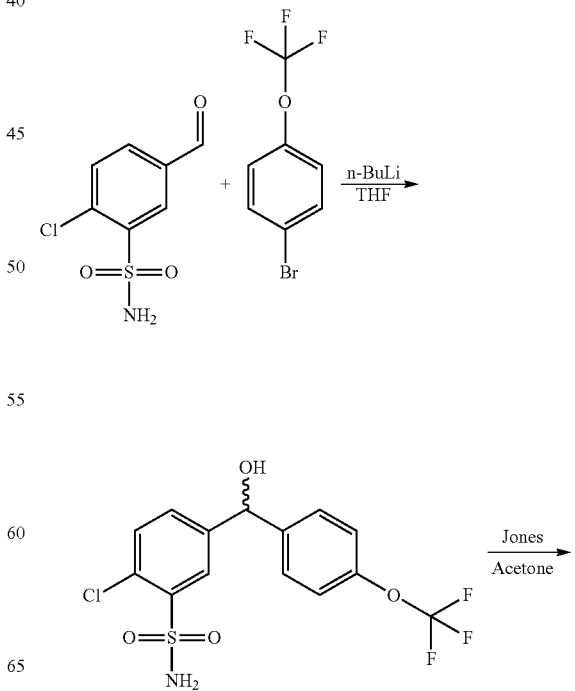

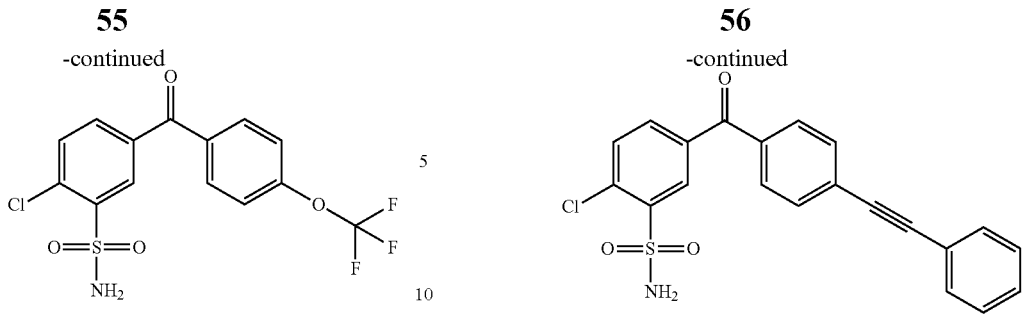

2-Chloro-5-[hydroxy-(4-trifluoromethoxy-phenyl)-methyl]-benzenesulfonamide

1-Bromo-4-trifluoromethoxy-benzene (660 mg, 2.73 mmol) is dissolved in tetrahydrofuran (2.5 mL) and cooled to −78° C. The solution is treated with a solution of n-butyllithium (1.6 M in hexanes, 1.7 mL, 2.73 mmol) which resulted in precipitation of the aryllithium. The suspension is allowed to warm to ambient temperature and is added via canula to a solution of 2-chloro-5-formyl-benzenesulfonamide (200 mg, 0.91 mmol) in tetrahydrofuran (2.5 mL) at −78° C. The reaction is allowed to warm to ambient temperature, at which point it is quenched with a saturated solution of ammonium chloride. The tetrahydrofuran is removed in vacuo and the residue is diluted with water and extracted with ethyl acetate. The organic phase is separated and concentrated in vacuo. The residue is used without further purification.

2-Chloro-5-(4-trifluoromethoxy-benzoyl)-benzenesulfonamide

2-Chloro-5-[hydroxy-(4-trifluoromethoxy-phenyl)-methyl]-benzenesulfonamide is dissolved in acetone (10 mL), and treated with a solution of Jones reagent (3 M in water, 0.91 mmol). The reaction is allowed to stir for 30 minutes. The reaction is diluted with water and extracted with dichloromethane. The organic phase is separated and concentrated in vacuo. The residue is purified by silica gel chromatography (gradient of ethyl acetate in hexanes 10-50%) affording 92 mg of the title compound. $^1$H NMR (CDCl$_3$) δ 5.20 (s, 2H), 7.35 (d, 2H, J=8.3 Hz), 7.70 (d, 1H, J=8.3), 7.84 (d, 2H, J=8.7 Hz), 7.95 (dd, 1 h, J=1.9, 8.3), 8.48 (d, 1H, J=1.9). MS (m/z): 378 (M−1). CHN Calc C, 44.28; H, 2.39; N, 3.69. Found C, 43.97; H, 2.22; N, 3.60.

Example 21

2-Chloro-5-(4-phenylethynyl-benzoyl)-benzenesulfonamide

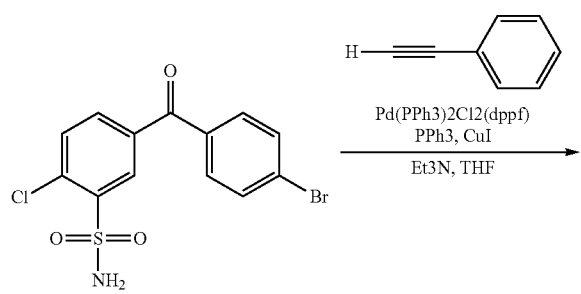

To a degassed solution of 5-(4-bromo-benzoyl)-2-chloro-benzenesulfonamide (500 mg, 1.33 mmol), phenylacetylene (204 mg, 2.00 mmol), copper iodide (15 mg), triphenylphosphine (9 mg, 0.033 mmol) and triethylamine (0.278 mL, 2 mmol) in tetrahydrofuran (4 mL) is added dichlorobis(triphenylphosphine)-palladium (47 mg, 0.067 mmol). The reaction mixture is allowed to stir at room temperature for 18 hours then poured into water (25 mL) and extracted twice with ethyl acetate. The organic fractions are combined, washed twice with a saturated sodium chloride solution, dried with magnesium sulfate, filtered and concentrated in vacuo. The resulting residue is purified via silica gel chromatography (20-50% ethyl acetate in hexanes) to yield the title compound as a white solid. MS (m/z): 394 (M−1).

Example 22

4-(4-Chloro-3-sulfamoyl-benzoyl)-N-(2-pyridin-2-yl-ethyl)-benzamide

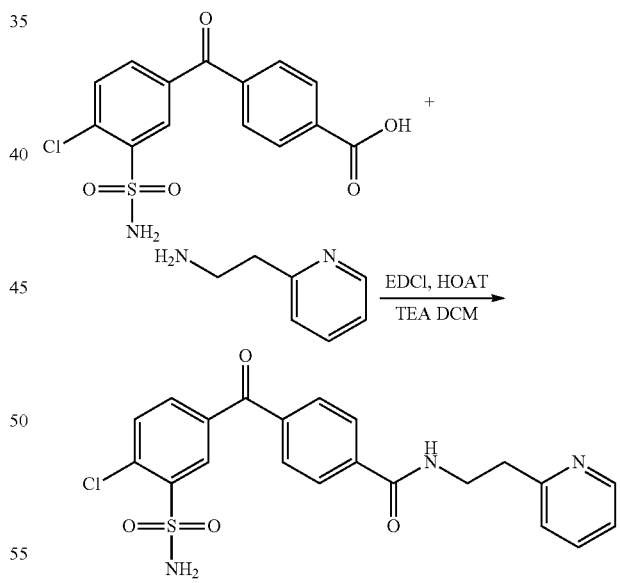

4-(4-Chloro-3-sulfamoyl-benzoyl)-N-(2-pyridin-2-yl-ethyl)-benzamide 4-(4-Chloro-3-sulfamoyl-benzoyl)-benzoic acid (50 mg, 0.15 mmol), 1-ethyl-3-(3'-dimethylaminopropyl)carbodiimide (57 mg, 0.30 mmol), 1-hydroxy-7-azabenzotriazole (41 mg, 0.30 mmol) were dissolved in dichloromethane (5 mL), then triethylamine (61 mg, 0.60 mmol) is added followed by 2-pyridin-2-yl-ethylamine (23 mg, 0.19 mL) and the reaction is allowed to stir at ambient temperature overnight. The reaction is then quenched with trifluoroacetic acid (1 mmol) and loaded directly onto a silica gel column, chromatography (gradient of ethyl acetate in hexanes 10-100%) followed by crystallization from ether afforded 20 mg of the title compound. $^1$H NMR (DMSO) δ 3.02 (t, 2H, J=7.57 Hz), 3.63-3.68 (m, 2H), 7.22-7.25 (m, 1H), 7.30 (d, 1H, J=7.83 Hz), 7.70-7.74 (m, 1H), 7.83-7.87 (m, 5H), 7.92-7.99 (m, 3H), 8.31 (d, 1H, J=2.02), 8.51-8.53 (m, 1H), 8.85-8.82 (m, 1H). MS (m/z): 442 (M−1). CHN Calc C, 56.82; H, 4.09; N, 9.47. Found C, 55.65; H, 3.90; N, 9.22. (+0.5 water).

Example 23

2-Chloro-5-(4-pyrrolidin-1-yl-benzoyl)-benzene-sulfonamide

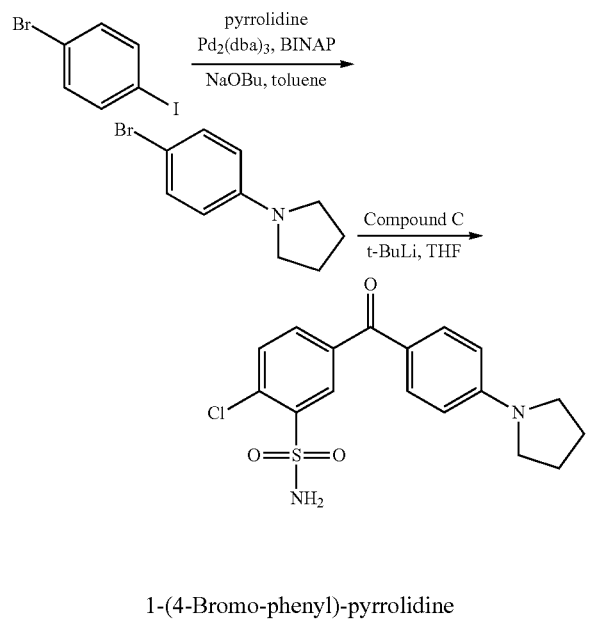

1-(4-Bromo-phenyl)-pyrrolidine

A oven-dried 50 mL of round bottom flask is charged with Pd$_2$(dba)$_3$ (116 mg, 0.13 mmol), BINAP (158 mg, 0.25 mmol), and sodium tert-butoxide (916 mg, 9.54 mmol). The flask is evacuated and backfilled with argon. Degassed toluene (5 mL), 1-iodo-4-bromobenzene (1.8 g, 6.36 mmol), pyrrolidine (542 mg, 7.63 mmol) are then added. The mixture is heated at 80° C. until the starting aryl iodide is completed consumed judged by LC-MS analysis. The mixture is diluted with ethyl acetate, filtered through Celite, and concentrated in vacuo. The crude product is purified by flash chromatography to give 1.1 g of product as light brown solid. $^1$H NMR (400 MHz, CDCl$_3$): δ 2.00 (t, 4H, J=4 Hz), 3.24 (t, 4H, J=4 Hz), 6.42 (d, 2H, J=8 Hz), 7.29 (d, 2H, J=8 Hz).

2-Chloro-5-(4-pyrrolidin-1-yl-benzoyl)-benzene-sulfonamide

Following method C, 1-(4-bromo-phenyl)-pyrrolidine is converted into the title compound. $^1$H NMR (400 MHz, CDCl$_3$): δ2.06 (t, 4H, J=8 Hz), 3.40 (t, 4H, J=8 Hz), 5.19 (s, 2H), 6.55 (d, 2H, J=6 Hz), 7.63 (d, 1H, J=8 Hz), 7.72 (d, 2H, J=8 Hz), 7.86 (d, 1H, J=8 Hz), 8.41 (s, 1H). MS (m/z): 365 (M+1).

Example 24

2-Chloro-5-[4-(2,5-dihydro-pyrrol-1-yl)-benzoyl]-benzenesulfonamide

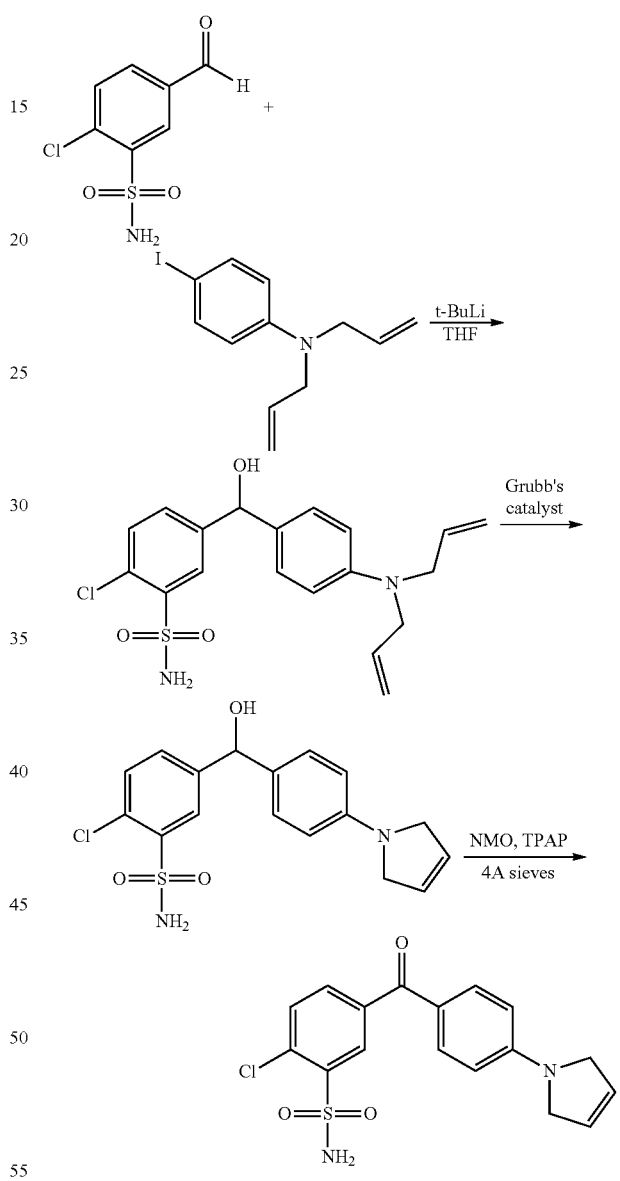

Following method B, 2-chloro-5-((4-diallylamino-phenyl)-hydroxy-methyl)-benzenesulfonamide is synthesized from the appropriate aryl iodide.

2-Chloro-5-{[4-(2,5-dihydro-pyrrol-1-yl)-phenyl]-hydroxy-methyl}-benzenesulfonamide A solution of 100 mg of 2-chloro-5-((4-diallylamino-phenyl)-hydroxy-methyl)-benzenesulfonamide (0.25 mmol, 1 equivalent) in 5 mL of chloroform is degassed with argon for 5 minutes, then 5 mg of Grubb's catalyst (0.005 mmol, 2% mmol) is added. The reaction mixture is stirred at room temperature for 1 h, then diluted with dichloromethane, filtered through Celite, and a pad of silica gel, then concentrated in vacuo to give 70 mg of the title compound which is carried forward without further purification.

2-Chloro-5-[4-(2,5-dihydro-pyrrol-1-yl)-benzoyl]-benzenesulfonamide

Following method B the title compound is prepared from 2-chloro-5-{[4-(2,5-dihydro-pyrrol-1-yl)-phenyl]-hydroxymethyl}-benzenesulfonamide. ¹H NMR (400 MHz, CDCl₃): δ 0.92 (s, 4H), 5.28 (m, 2H), 6.42 (s, 2H), 7.180 (t, 1H, J=2 Hz), 7.55-7.7 (m, 3H), 7.85-8.05 (m, 2H). MS (m/z): 361 (M−1).

Example 25

2-Chloro-5-(4-piperidin-1-yl-benzoyl)-benzenesulfonamide

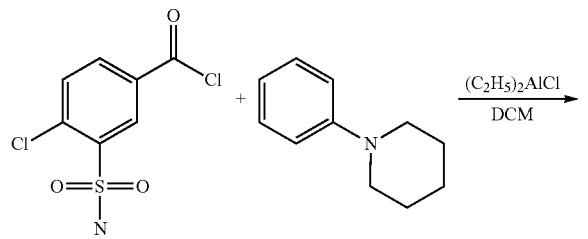

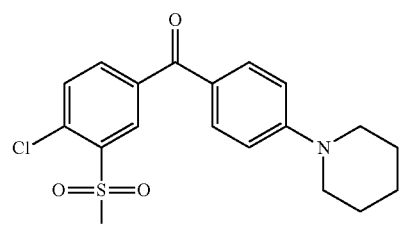

A solution of 300 mg of 4-chloro-3-sulfamoyl-benzoyl chloride (1.186 mmol, 1 equivalent) in 20 mL of dichloromethane is stirred at room temperature as 2.37 mL of diethyl aluminum chloride (1.0 M in hexane) is added dropwise. The reaction is stirred at room temperature for 10 minutes, then 229 mg of 1-phenyl piperidine is added. The reaction is stirred at room temperature for 30 minutes. The reaction mixture is poured onto ice-2 N HCl and extracted with dichloromethane. The aqueous layer is then basified with 2 N sodium hydroxide and extracted with dichloromethane. The combined organic extracts are washed with water, dried over sodium sulfate, and concentrated in vacuo. After purification by flash chromatography, 180 mg of product is obtained. ¹H NMR (400 MHz, CDCl₃): δ 1.69 (s, 6H), 3.18 (m, 1H), 3.42 (s, 3H), 5.18 (s, 2H), 6.86 (d, 2H, J=8 Hz), 7.62 (d, 1H, J=8 Hz), 7.70 (d, 2H, J=8 Hz), 7.87 (d, 1H, J=8 Hz), 8.42 (s, 1H). MS (m/z): 379 (M+1). Analytics calculated for C₁₈H₁₉ClN2O₃S: C, 57.06; H, 5.05; N, 7.39. Found: C, 56.88; H, 5.04; N, 7.13.

Example 26

2-Chloro-5-[4-(3-methyl-piperidin-1-yl)-benzoyl]-benzenesulfonamide

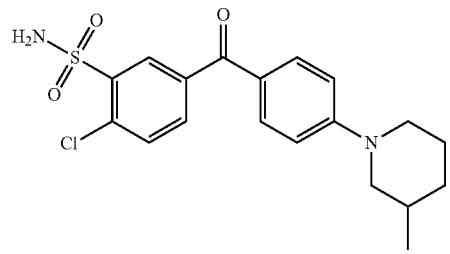 [SMILES: CC1CCCN(c2ccc(C(=O)c3ccc(Cl)c(S(N)(=O)=O)c3)cc2)C1]

Preparation of 1-(4-bromo-phenyl)-3-methyl-piperidine 1-(4-Bromo-phenyl)-3-methyl-piperidine is prepared from 0.25 mL of 3-methylpiperidine according to the procedure described in example 25. MS (m/z): 255 (M+1).

A solution of 0.821 g of 1-(4-bromo-phenyl)-3-methyl-piperidine in tetrahydrofuran is cooled to −78° C. and treated with 0.3 g of 4-chloro-N-methoxy-N-methyl-3-sulfamoyl-benzamide. The mixture is stirred for 10 min and treated slowly with 4.31 mL of a solution of tert-butyl lithium (1.5 M) in tetrahydrofuran (3 mL). The orange solution is stirred at −78° C. for 15 min then at 0° C. for 1 hour. The reaction mixture is quenched with saturated aqueous ammonium chloride (100 mL) and extracted with ethyl acetate (2×50 mL). The organics are washed with water, a saturated sodium chloride solution, dried over sodium sulfate, filtered and concentrated in vacuo. The residue is loaded on Celite and purified by silica gel chromatography (1:1 hexanes/ethyl acetate) to give 2-chloro-5-[4-(3-methyl-piperidin-1-yl)-benzoyl]-benzenesulfonamide as a light yellow syrup. MS (m/z): 393 (M+1). HPLC Reverse Phase (Nucleosil 100-5 C18, gradient 10->100% CH₃CN in 5 min) room temperature=5.40 minutes.

Example 27

2-Chloro-5-[4-(4-phenyl-piperidin-1-yl)-benzoyl]-benzenesulfonamide

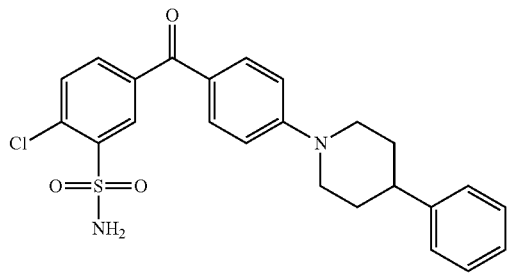 [SMILES: NS(=O)(=O)c1cc(C(=O)c2ccc(N3CCC(c4ccccc4)CC3)cc2)ccc1Cl]

A solution of 0.227 g of 1-(4-bromo-phenyl)-4-phenyl-piperidine in tetrahydrofuran (5 mL) is cooled to −78° C. and treated with 2 portions of 0.29 mL each of tert-butyllithium (1.5 M in pentane). After 20 min at −78° C. the reaction mixture is treated with 0.1 g of 4-chloro-N-methoxy-N-methyl-3-sulfamoyl-benzamide in tetrahydrofuran (5 mL) and stirred for another 1.5 h. The temperature is then increased slowly to 0° C. and after completion the reaction is quenched by addition of 2 mL of saturated aqueous ammonium chloride and extracted with diethyl ether. The organics are washed with water, dried over magnesium sulfate, concentrated to 0.27 g of crude product which is purified by silica gel chromatography (1:1 hexanes/ethyl acetate) to give 2-chloro-5-[4-(4-phenyl-piperidin-1-yl)-benzoyl]-benzenesulfonamide as a powder. MS (m/z): (M−1) 453; Rf 0.65 (1:1 hexanes/ethyl acetate)

Example 28

2-Chloro-5-[4-(4-methyl-piperazin-1-yl)-benzoyl]-benzenesulfonamide

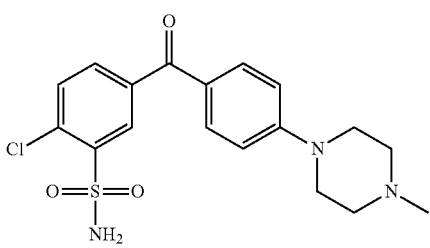 [SMILES: CN1CCN(c2ccc(C(=O)c3ccc(Cl)c(S(N)(=O)=O)c3)cc2)CC1]

A solution of 0.275 g of 1-(4-bromo-phenyl)-4-methyl-piperazine in tetrahydrofuran (90 mL) is cooled to −78° C. and treated with 1.44 mL of tert-butyllithium (1.5 M in pentane). After 15 min at −78° C. the reaction mixture is treated with 0.1 g of 4-chloro-N-methoxy-N-methyl-3-sulfamoyl-benzamide in tetrahydrofuran (3 mL). The temperature is then increased slowly to 0° C. and after completion the reaction is quenched by addition of 2 mL of saturated aqueous ammonium chloride and extracted with diethyl ether. The organics are washed with water, dried (magnesium sulfate) and concentrated to give 0.32 g of crude product which is purified by silica gel chromatography (95:5 methylene chloride/methanol) to give 2-chloro-5-[4-(4-methyl-piperazin-1-yl)-benzoyl]-benzenesulfonamide as a tan powder. MS (m/z): 394 (M+1); Rf 0.06 (95:5 methylene chloride/methanol).

Example 29

2-Chloro-5-(indane-5-carbonyl)-benzenesulfonamide

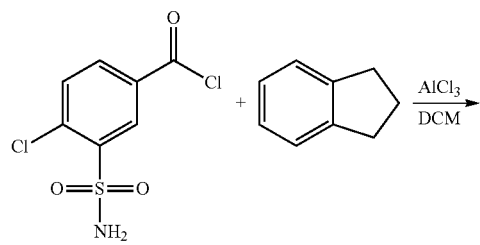

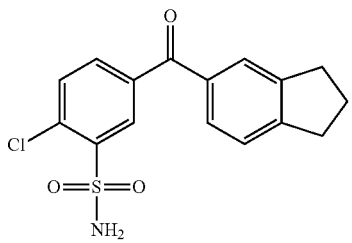

2-Chloro-5-(indane-5-carbonyl)-benzenesulfonamide

Under nitrogen, aluminum chloride (315 mg, 2.4 mmol) is slurried in dichloromethane (20 mL) then 3-chlorosulfonyl-benzoyl chloride (200 mg, 0.79 mmol) is added and the reaction is allowed to stir at ambient temperature for 10 minutes. Indan (100 mg, 0.79 mmol) is added. The reaction is allowed to stir at ambient temperature for 18 hours. The reaction mixture is poured over ice-water and extracted with dichloromethane. The organic layer is concentrated to give 265 mg of the title compound (100% yield). $^1$H NMR (CDCl$_3$, 300 MHz): δ 8.47 (d, 1H, J=2.19 Hz), 7.93 (dd, 1H, J=2.19, 8.33 Hz), 7.67 (d, 1H, J=8.11), 7.64 (s, 1H), 7.53 (d, 1H, J=7.89 Hz), 7.33 (d, 1H, J=7.89 Hz), 5.17 (s, 2H), 2.98 (m, 4H), 2.15 (m, 2H). M.P.: 164-166° C. MS (m/z): 336 (M+1).

Example 30

2-Chloro-5-(1H-pyrrole-3-carbonyl)-benzenesulfonamide

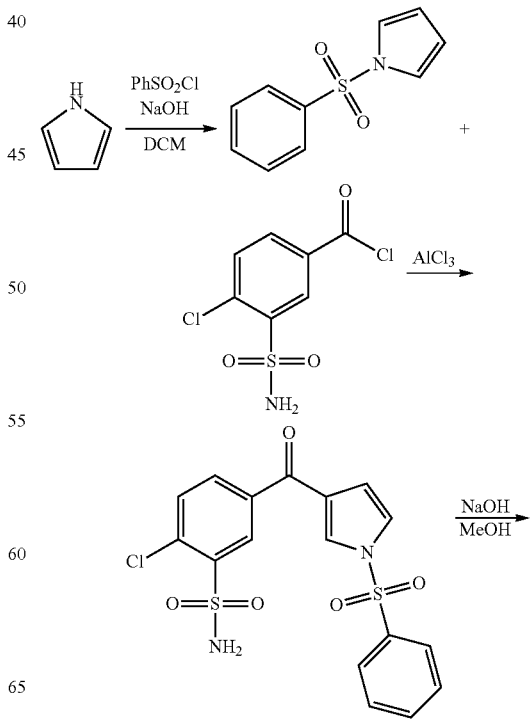

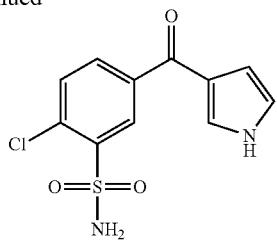

1-Benzenesulfonyl-1H-pyrrole

To a well-agitated suspension of sodium hydroxide (4.46 g, 111 mmol) in methylene chloride (26 mL) at 0° C. is added pyrrole (2.5 g, 0.37 mmol), and the reaction mixture is stirred for 10 min, following which a solution of benzenesulfonyl chloride (7.86 g, 0.44 mmol) in methylene chloride (5.15 mL) is slowly added, allowed to warm to room temperature and stirred overnight. The reaction is quenched by pouring into water (100 mL). The organic layer is separated, and the aqueous layer is extracted with methylene chloride three times. The combined organic extracts are water, dried with sodium sulfate, and concentrated in vacuo. Purification by silica gel chromatography (10% ethyl acetate-hexane) provides 4.6 g (60%) of the title compound as a white solid. $^1$H NMR (CDCl$_3$): δ 7.80 (m, 2H), 7.50 (m, 3H), 7.25 (m, 2H), 6.30 (m, 2H).

5-(1-Benzenesulfonyl-1H-pyrrole-3-carbonyl)-2-chloro-benzenesulfonamide

To a suspension of aluminum chloride (1.89 g, 14 mmol) in methylene chloride (10 mL) is added 4-chloro-3-sulfamoyl-benzoyl chloride (2 g, 7.9 mmol). The reaction mixture is stirred at room temperature for 10 minutes then a solution of 1-benzenesulfonyl-1H-pyrrole (1.13 g, 5.45 mmol) in methylene chloride (3.3 mL) is added. After stirring at room temperature overnight, the reaction is quenched with 6 N HCl and extracted with ethyl acetate three times. The combined organic layers are washed with a saturated sodium chloride solution, dried with magnesium sulfate and concentrated in vacuo. Purification by silica gel chromatography (ethyl acetate/hexane: 2:8) provides 0.6 g (26%) of the title compound as a yellow solid. $^1$H NMR (DMSO): δ 8.30 (s, 1H), 8.15 (m, 2H), 8.05 (m, 2H), 7.80 (m, 4H), 7.70 (m, 2H), 7.40 (m, 1H), 6.70 (m, 1H).

2-Chloro-5-(1H-pyrrole-3-carbonyl)-benzenesulfonamide 5-(1-Benzenesulfonyl-1H-pyrrole-3-carbonyl)-2-chloro-benzenesulfonamide (0.1 g, 0.23 mmol) is dissolved in 3 mL of 2:1 (v:v) mixture of methanol and 5 N aqueous sodium hydroxide and heated at reflux for 20 minutes then the reaction mixture is allowed to cool down and the organic solvent is removed in vacuo. The aqueous solution is acidified with 5 N HCl to pH 3, thoroughly extracted with ethyl acetate, then the combined organic extracts are washed with water, a saturated sodium chloride solution, dried with magnesium sulfate, and concentrated in vacuo. Recrystallization from ethyl acetate/methylene chloride provides 43 mg (66%) of the title compound as a white solid. $^1$H NMR (DMSO): δ 11.70 (s, 1H), 8.70 (m, 1H), 8.00 (m, 1H), 7.80 (m, 3H), 7.50 (m, 1H), 7.00 (m, 1H), 6.60 (m, 1H). MS (m/z): 285 (M+1) Analytics calculated For C$_{11}$H$_9$N$_2$ClO$_3$S: C, 46.40; H, 3.19; N, 9.84. Found: C, 45.84; H, 2.90; N, 9.41.

Example 31

2-Chloro-5-(thiophene-2-carbonyl)-benzenesulfonamide

2-Chloro-5-(thiophene-2-carbonyl)-benzenesulfonamide

To a solution of thiophene (0.27 g, 3.20 mmol) dissolved in tetrahydrofuran (10 mL) at −78° C. under nitrogen is dropwisely added 1.6 M of n-butyllithium (2 mL, 3.40 mmol). The reaction mixture is stirred at −78° C. for 1 h then a solution 4-chloro-N-methoxy-N-methyl-3-sulfamoyl-benzamide (0.3 g, 1.08 mmol) in tetrahydrofuran (2 mL) is added slowly and the reaction mixture is allowed to warm to room temperature and stirred for 1 h. The reaction is quenched with saturated ammonium chloride and extracted with ethyl acetate three times. The combined organic extracts are washed with a saturated sodium chloride solution, dried with magnesium sulfate, and concentrated in vacuo. Purification by silica gel chromatography (50% ethyl acetate-hexane) provides 0.059 g (18%) of the title compound as a yellow solid. $^1$H NMR (DMSO): δ 8.33 (d, J=2 Hz, 1H), 8.15 (dd, J=4, 1 Hz, 1H), 8.05 (dd, J=8, 4 Hz, 1H), 7.85 (m, 4H), 7.35 (m, 1H). Analytics calculated for $C_{11}H_8ClO_3S_2$: C, 43.78; H, 2.67; N, 4.64. Found: C, 43.70; H, 2.61; N, 4.61. MS (m/z): 300.0 (M−1).

Example 32

2-Chloro-5-(2-methyl-3H-benzoimidazole-5-carbonyl)-benzenesulfonamide

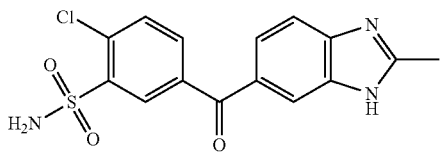 [SMILES: Cc1nc2ccc(C(=O)c3ccc(Cl)c(S(N)(=O)=O)c3)cc2[nH]1]

A solution of 0.303 g of 6-bromo-2-methyl-1H-benzoimidazole in tetrahydrofuran (20 mL) is cooled to −50° C. and treated with 2.7 mL of tert-butyllithium (1.5 M in pentane). After 2 h at −50° C. the reaction mixture is treated with 0.12 g of 4-chloro-N-methoxy-N-methyl-3-sulfamoyl-benzamide in tetrahydrofuran (10 mL). After 3 h the mixture is quenched with saturated aqueous ammonium chloride, taken up in ethyl acetate, and washed with saturated aqueous sodium chloride. The organics are dried (magnesium sulfate), concentrated and purified by silica gel chromatography (98:2 methylene chloride/methanol) to give 2-chloro-5-(2-methyl-3H-benzoimidazole-5-carbonyl)-benzenesulfonamide. MS (m/z): 348 (M−1); Rf 0.30 (9:1 methylene chloride/methanol).

Example 33

5-(9H-Carbazole-2-carbonyl)-2-chloro-benzenesulfonamide

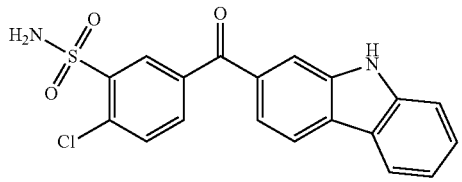 [SMILES: NS(=O)(=O)c1cc(C(=O)c2ccc3c(c2)[nH]c2ccccc23)ccc1Cl]

A mixture of 0.5 g of 5-(9-acetyl-9H-carbazole-2-carbonyl)-2-chloro-benzenesulfonamide and 20 mL of potassium hydroxide solution (10% in water) is heated at reflux overnight and is allowed to cool to room temperature. The reaction mixture is extracted with ethyl acetate, washed with water then a saturated sodium chloride solution, and dried over sodium sulfate. After concentration the residue is loaded on Celite and purified by silica gel chromatography (1:1 hexanes/ethyl acetate) to give 5-(9H-carbazole-2-carbonyl)-2-chloro-benzenesulfonamide as dark orange crystals. MS (m/z): 385 (M+1).

Preparation of 5-(9-acetyl-9H-carbazole-2-carbonyl)-2-chloro-benzenesulfonamide

To a solution of 1 g of 1-carbazol-9-yl-ethanone and 2.43 g of 4-chloro-3-sulfamoyl-benzoyl chloride in methylene chloride (20 mL) is added 2.55 g of aluminum chloride. The mixture is stirred at 50° C. overnight. The solution is then cooled at −78° C., quenched with a 6 N HCl solution and allowed to warm up to room temperature. Methylene chloride is added to dissolve the precipitate and the solution is extracted, washed with a saturated sodium chloride solution, dried over sodium sulfate, filtered and concentrated. The residue is loaded on Celite and purified by silica gel chromatography (1:1 hexanes/ethyl acetate) to afford 5-(9-acetyl-9H-carbazole-2-carbonyl)-2-chloro-benzenesulfonamide as yellow foam. MS (m/z): 427 (M+1). HPLC Reverse Phase (Nucleosil 100-5 C18, gradient 10->100% $CH_3CN$ in 5 min) room temperature=5.35 minutes.

Example 34 and Example 35

8-(4-Chloro-3-sulfamoyl-benzoyl)-1,3,4,5-tetrahydro-pyrido[4,3-b]indole-2-carboxylic acid ethyl ester and 7-(4-chloro-3-sulfamoyl-benzoyl)-1,3,4,5-tetrahydro-pyrido[4,3-b]indole-2-carboxylic acid ethyl ester

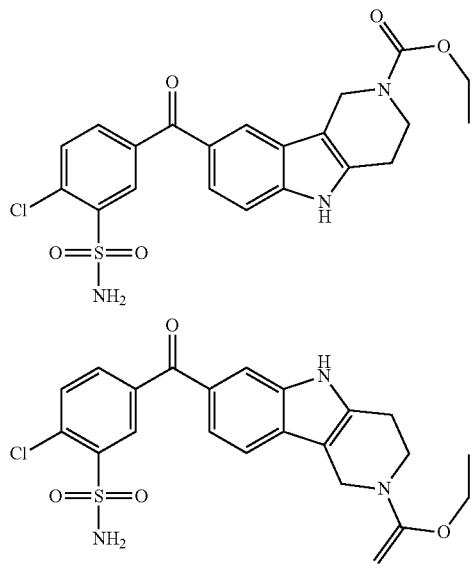

A mixture of 5-benzenesulfonyl-8-(4-chloro-3-sulfamoyl-benzoyl)-1,3,4,5-tetrahydro-pyrido[4,3-b]indole-2-carboxylic acid ethyl ester and 5-benzenesulfonyl-7-(4-chloro-3-sulfamoyl-benzoyl)-1,3,4,5-tetrahydro-pyrido[4,3-b]indole-2-carboxylic acid ethyl ester (1 g) is dissolved in 5 mL of tetrahydrofuran-methanol-water (10:10:1) and treated with 0.344 g of potassium carbonate. The reaction mixture is heated at 140° C. for 15 min (microwave irradiation), filtered and concentrated. The residue is purified on reverse phase HPLC to give pure 8-(4-chloro-3-sulfannoyl-benzoyl)-1,3,4,5-tetrahydro-pyrido[4,3-b]indole-2-carboxylic acid ethyl ester MS (m/z): 462 (M+1); and 7-(4-chloro-3-sulfamoyl-benzoyl)-1,3,4,5-tetrahydro-pyrido[4,3-b]indole-2-carboxylic acid ethyl ester MS (m/z): 462 (M+1); both as yellow syrups. Both isomers are separated by HPLC (Chiracel OD-H 250-4.6 mm, flow 1 ml/Min, UV 235 nM, gradient hexane-ethanol 70-30). The retention times are 6.91 min for 8-(4-chloro-3-sulfamoyl-benzoyl)-1,3,4,5-tetrahydro-pyrido[4,3-b]indole-2-carboxylic acid ethyl ester and 10.20 min for 7-(4-chloro-3-sulfamoyl-benzoyl)-1,3,4,5-tetrahydro-pyrido[4,3-b]indole-2-carboxylic acid ethyl ester.

Preparation of 5-benzenesulfonyl-8-(4-chloro-3-sulfamoyl-benzoyl)-1,3,4,5-tetrahydro-pyrido[4,3-b]indole-2-carboxylic acid ethyl ester and 5-benzenesulfonyl-7-(4-chloro-3-sulfamoyl-benzoyl)-1,3,4,5-tetrahydro-pyrido[4,3-b]indole-2-carboxylic acid ethyl ester Step 1

A solution of 3 g of 1,3,4,5-tetrahydro-pyrido[4,3-b]indole-2-carboxylic acid ethyl ester in methylene chloride (50 mL) is treated with 0.982 g of sodium hydroxide and stirred and room temperature overnight. Benzenesulfonylchloride (6.30 mL) is added to the reaction and stirred at room temperature overnight. The reaction mixture is diluted with water (250 mL) and extracted with methylene chloride. The organics are combined, washed with water then a saturated sodium chloride solution, dried over sodium sulfate and concentrated in vacuo The residue is loaded on Celite and purified by silica gel chromatography (1:1 hexanes/ethyl acetate) to give 5-benzenesulfonyl-1,3,4,5-tetrahydro-pyrido[4,3-b]indole-2-carboxylic acid ethyl ester as a yellow powder. MS (m/z): 385 (M+1).

Step 2

The mixture of regioisomers 5-benzenesulfonyl-8-(4-chloro-3-sulfamoyl-benzoyl)-1,3,4,5-tetrahydro-pyrido[4,3-b]indole-2-carboxylic acid ethyl ester and 5-benzenesulfonyl-7-(4-chloro-3-sulfannoyl-benzoyl)-1,3,4,5-tetrahydro-pyrido[4,3-b]indole-2-carboxylic acid ethyl ester is prepared from 0.5 g of 5-benzenesulfonyl-1,3,4,5-tetrahydro-pyrido[4,3-b]indole-2-carboxylic acid ethyl ester according to the procedure described in example 102. MS (m/z): 603 (M+1).

Example 36

2-Chloro-5-(1-oxo-2,3,4,9-tetrahydro-1H-pyrido[3,4-b]indole-7-carbonyl)-enzenesulfonamide

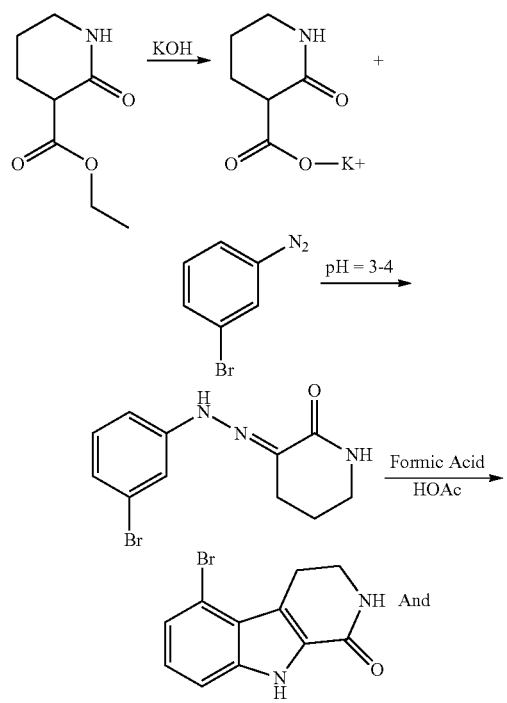

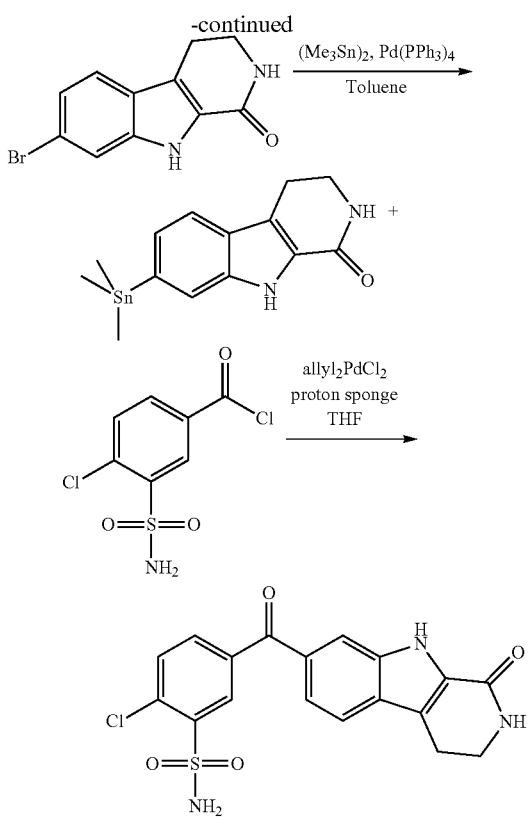

2,3-Piperidinedione 3-(3-bromophenyl) hydrazone

3-Carbethoxy-2-piperidone (4.7 g, 27.4 mmol) is stirred with potassium hydroxide (1.64 g) in water (56 mL) and kept at 30° C. on an oil bath overnight. 3-Bromoaniline (4.99 g, 29 mmol) is treated with water (50 mL) and concentrated HCl (10 mL) and cooled to 0° C. Sodium nitrite (2.46 g, 35 mmol) in water (9 mL) is added dropwise to the above solution at 0° C. and stirred for an additional 20 minutes. Urea is added to decompose the excess nitrous acid, and the diazotized solution is neutralized with 10% aqueous sodium carbonate solution (45-50 mL). The resulting solution is filtered into the solution of previously hydrolyzed 3-carbethoxy-2-piperidone (2-piperidone-3-carboxylic acid) at 0° C. After a few minutes, glacial acetic acid is added to bring the pH of the solution to 3-4. The reaction mixture is stirred at 0° C. for 5-6 h, and the yellow precipitate which resulted is filtered, washed with water, and dried to get the title compound (2.5 g, 32% yield).

7-Bromo-2,3,4,9-tetrahydro-pyrido[3,4-b]indol-1-one

A solution of 2,3-piperidinedione 3-(3-bromophenyl) hydrazone (2.5 g, 22.3 mmol) in formic acid (40 mL) is refluxed for 1 h then cooled to room temperature. The reaction mixture is neutralized with sodium carbonate to basic condition. The resulting precipitate is filtered and collected. Recrystallization with ethanol provides 1.0 g (56%) of the title compound as a yellow solid.

7-Trimethylstannanyl-2,3,4,9-tetrahydro-pyrido[3,4-b]indol-1-one

7-Bromo-2,3,4,9-tetrahydro-pyrido[3,4-b]indol-1-one (0.42 g, 1.59 mmol) and hexamethylditin (0.64 g, 1.96 mmol)

are dissolved in deoxygenated toluene (16 mL) under a nitrogen atmosphere. Palladium tetrakis(triphenylphosphine) (0.118 g, 0.11 mmol) is added, and the mixture is heated at reflux for 7 h. The reaction mixture is partitioned between pH 7 buffer and ethyl acetate, and the aqueous layer is extracted with ethyl acetate three times. The combined organics are dried over magnesium sulfate and concentrated in vacuo. The title compound is obtained as the yellow oil, which is used in the next step without further purification.

2-Chloro-5-(1-oxo-2,3,4,9-tetrahydro-1H-pyrido[3,4-b]indole-7-carbonyl)-enzenesulfonamide 7-Trimethylstannanyl-2,3,4,9-tetrahydro-pyrido[3,4-b]indol-1-one (0.66 g, 1.88 mmol) and 1,8-bis(dimethylamino)naphthalene (0.210 g, 0.94 mmol) in tetrahydrofuran (25 mL) is treated with 4-chloro-3-sulfamoyl-benzoyl chloride (0.48 g, 1.88 mmol). After a few minutes, allylpalladium chloride dimer (0.057 g, 0.15 mmol) is added. The reaction mixture is stirred for 5 min at room temperature and then refluxed for 2 h. After cooling to room temperature the reaction mixture is diluted with methylene chloride and washed with a saturated sodium chloride solution then concentrated in vacuo. Purification by silica gel chromatography (75% ethyl acetate-hexane) followed by recrystallization (ethanol-ethyl acetate) provides 0.014 g (1.8%) of the title compound as a pale yellow solid. $^1$H NMR (DMSO): δ 12.00 (s, 1H), 8.30 (s, 1H), 8.00 (m, 1H), 7.90 (m, 6H), 7.60 (m, 1H), 3.40 (m, 2H), 3.00 (m, 2H). MS (m/z): 402.0 (M−1).

Example 37

2-Chloro-5-[2-(2,2-dimethyl-propionyl)-2,3,4,9-tetrahydro-1H-pyrido[3,4-b]indole-6-carbonyl]-benzenesulfinamide

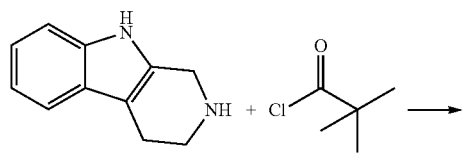

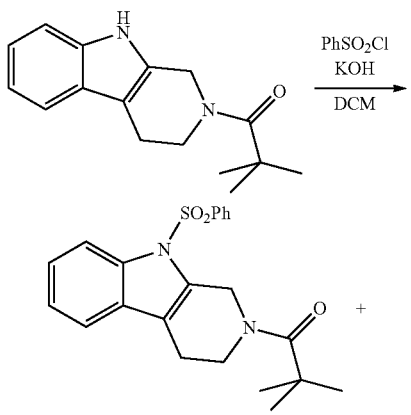

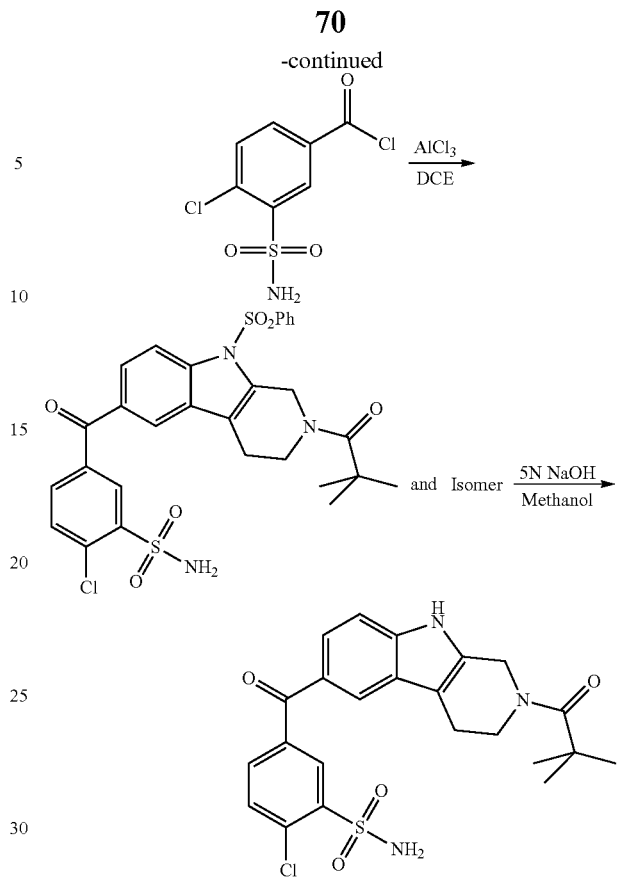

2,2-Dimethyl-1-(1,3,4,9-tetrahydro-pyrido[3,4-b]indol-2-yl)-propan-1-one

To a solution of 2,3,4,9-tetrahydro-1H-pyrido[3,4-b]indole (2 g, 11.6 mmol) dissolved in methylene chloride (20 mL) is added 2,2-dimethyl-propionyl chloride (1.42 mL, 11.6 mmol) followed by the addition of triethylamine (1.61 mL, 11.6 mmol). The reaction mixture is stirred at room temperature for 30 minutes The reaction is quenched with water and extracted with methylene chloride three times. The combined organic extracts are washed with saturated sodium bicarbonate, a saturated sodium chloride solution, dried with magnesium sulfate, and concentrated in vacuo to give 2.8 g (94%) of the title compound as a grey solid.

1-(9-Benzenesulfonyl-1,3,4,9-tetrahydro-pyrido[3,4-b]indol-2-yl)-2,2-dimethyl-propan-1-one To a well-agitated suspension of sodium hydroxide (0.81 g, 20.2 mmol) in methylene chloride (10 mL) is added 2,2-dimethyl-1-(1,3,4,9-tetrahydro-pyrido[3,4-b]indol-2-yl)-propan-1-one (2.3 g, 8.98 mmol). The reaction mixture is stirred for 15 min, and then benzenesulfonyl chloride (1.89 g, 10.7 mmol) is added. The solution is stirred at room temperature for 1 h. The reaction is diluted with methylene chloride, washed with water then a saturated sodium chloride solution, dried with sodium sulfate and concentrated in vacuo. Purification by silica gel chromatography (50% ethyl acetate-hexane) provides 2.0 g (56.2%) of the title compound as a white solid.

5-[9-Benzenesulfonyl-2-(2,2-dimethyl-propionyl)-2,
3,4,9-tetrahydro-1H-pyrido[3,4-b]indole-6-carbonyl]-2-chloro-benzenesulfinamide and 5-[9-Benzenesulfonyl-2-(2,2-dimethyl-propionyl)-2,3,4,9-tetrahydro-1H-pyrido[3,4-b]indole-7-carbonyl]-2-chloro-benzenesulfinamide To a suspension of aluminum chloride (0.338 g, 2.54 mmol) in methylene chloride (10 mL) is added 4-chloro-3-sulfamoyl-benzoyl chloride (0.36 g, 1.41 mmol). The reaction mixture is stirred at room temperature for 15 min then 1-(9-benzenesulfonyl-1,3,4,9-tetrahydro-pyrido[3,4-b]indol-2-yl)-2,2-dimethyl-propan-1-one is added. After the mixture is stirred at room temperature overnight, the reaction is quenched with 6 N HCl and extracted with methylene chloride three times. The combined organic layers are washed with a saturated sodium chloride solution, dried with magnesium sulfate, and concentrated in vacuo. Purification by silica gel chromatography (ethyl acetate/hexane: 2:8) provides 0.12 g (13.8%) of the two title compounds as a yellow solid.

2-Chloro-5-[2-(2,2-dimethyl-propionyl)-2,3,4,9-tetrahydro-1H-pyrido[3,4-b]indole-6-carbonyl]-benzenesulfinamide 5-[9-Benzenesulfonyl-2-(2,2-dimethyl-propionyl)-2,3,4,9-tetrahydro-1H-pyrido[3,4-b]indole-6-carbonyl]-2-chloro-benzenesulfinamide and its isomer (0.12 g, 0.195 mmol) are dissolved in 3 mL of 2:1 (v:v) mixture of methanol and 5 N aqueous sodium hydroxide then heated at reflux for 20 minutes The reaction mixture is allowed to cool to room temperature and the methanol is removed in vacuo. The aqueous solution is acidified with 5 N HCl to pH 3 and then thoroughly extracted with ethyl acetate, the combined organic extracts are washed with water then a saturated sodium chloride solution, dried with magnesium sulfate, and concentrated in vacuo. Purification via preparative HPLC provides 0.014 g (15%) of the title compound as a yellow solid. ¹H NMR (DMSO): δ 11.40 (s, 1H), 8.30 (s, 1H), 7.90 (m, 2H), 7.80 (m, 3H), 7.50-7.60 (m, 2H), 4.74 (s, 2H), 4.00 (m, 2H), 2.80 (m, 2H). MS (m/z): 472.1 (M−1).

Example 38

2-Chloro-5-(1-methyl-2-oxo-2,3,4,9-tetrahydro-1H-indeno[2,1-b]pyridine-7-carbonyl)-benzenesulfonamide

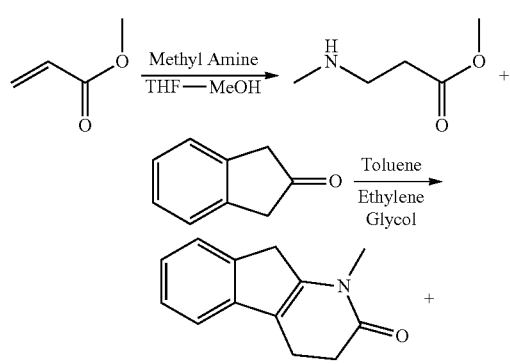

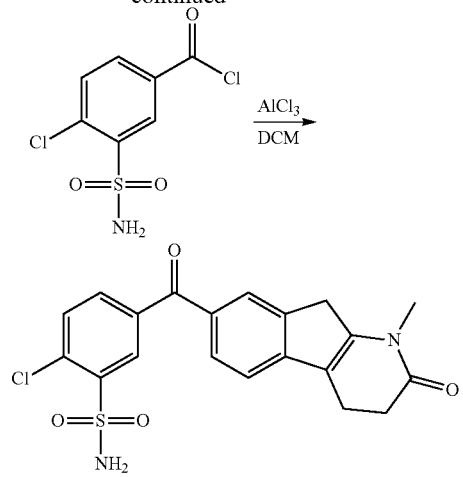

3-Methylamino-propionic acid methyl ester

Methyl acrylate (10 g, 116 mmol) is dissolved in methanol (20 mL) and cooled to −20° C. Methylamine (2 M in tetrahydrofuran, 90 mL, 180 mmol) is added via addition funnel and the reaction is allowed to stir at −20° C. for 2 hours. Solvents were then removed in vacuo and the residue is distilled under reduced pressure (45° C. at 5 torr) to afford the title compound as a colorless liquid (3.5 g, 28% yield). ¹H NMR (CDCl₃) δ 2.44 (s, 3H), 2.52 (t, 2H, J=6.31 Hz), 2.86 (t, 2H, J=6.31 Hz), 3.69 (s, 3H).

1-Methyl-1,3,4,9-tetrahydro-indeno[2,1-b]pyridin-2-one

3-Methylamino-propionic acid methyl ester (1.5 g, 13.64 mmol) is added to a solution of 2-indanone (1.7 g, 12.86 mmol) in toluene (20 mL) and the reaction is brought to reflux for 2.5 hours. Toluene is removed in vacuo and the residue is dissolved in ethylene glycol (17 mL) and the resulting solution is heated to reflux for 8 hours. The reaction is allowed to cool to ambient temperature, is poured over water and extracted with dichloromethane. The organic phase is dried over magnesium sulfate and concentrated in vacuo to afford the crude title compound as a brown oil. The crude product is purified by silica gel chromatography (gradient of ethyl acetate in hexanes 10-100%) affording 720 mg (28% yield) of the title compound. ¹H NMR (CDCl₃) δ 2.70-2.80 (m, 4H), 3.23 (s, 3H), 3.5 (s, 2H), 7.07-7.15 (m, 2H), 7.24-7.33 (m, 1H), 7.38 (d, 1H, J=7.07). MS (m/z): 199.2 (M+1).

2-Chloro-5-(1-methyl-2-oxo-2,3,4,9-tetrahydro-1H-indeno[2,1-b]pyridine-7-carbonyl)-benzenesulfonamide Under nitrogen, aluminum chloride (2.0 g, 15.06 mmol) is slurried in dichloromethane (100 mL) then 4-chloro-3-sulfamoyl-benzoyl chloride (1.28 g, 5.02 mmol) is added and allowed to stir at ambient temperature for 30 minutes. To this mixture 1-methyl-1,3,4,9-tetrahydro-indeno[2,1-b]pyridin-2-one (1.0 g, 5.02 mmol) is added in 13 mL dichloromethane. The reaction is allowed to stir at ambient temperature for 1 hour. The reaction mixture is poured over ice-water (300 mL) and extracted with dichloromethane, organic separated and concentrated to give crude title compound. Recrystallization from warm methanol afforded the title compound as a yellow powder (1.11 g, 53% yield). ¹H NMR (MeOD) δ 2.77-2.83 (m, 4H), 3.28 (s, 3H), 3.59 (s, 2H), 5.17 (s, 2H), 7.19 (d, 1H, J=7.83 Hz), 7.68-7.73 (m, 2H), 7.86 (s, 1H), 7.94 (dd, 1H, J=2.27, 8.33 Hz), 8.46 (d, 1H, J=2.02 Hz). MS (m/z): 417 (M+1). M.P. 259-260° C.

Example 39

2-Chloro-5-(1-ethyl-2-oxo-2,3,4,9-tetrahydro-1H-indeno[2,1-b]pyridine-7-carbonyl)-benzenesulfonamide

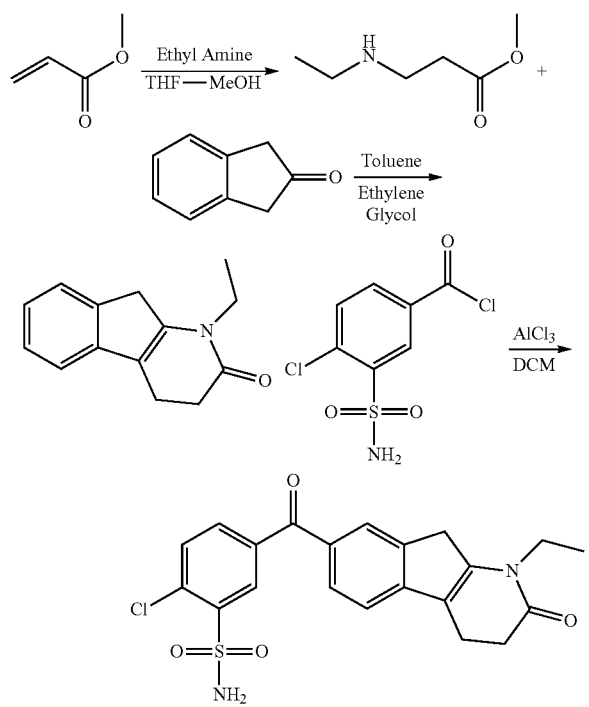

3-Ethylamino-propionic acid methyl ester

Methyl acrylate (5.22 g, 60.6 mmol) is dissolved in methanol (20 mL) and cooled to −20° C. Ethylamine (2 M in tetrahydrofuran, 47 mL, 94 mmol) is added via addition funnel and the reaction is allowed to stir at −20° C. for 2 hours. Solvents were then removed in vacuo and the residue is distilled under reduced pressure to afford the title compound as a colorless liquid (2.41 g, 30% yield). ¹H NMR (CDCl₃) δ 1.11 (t, 3H, J=7.02 Hz), 2.53 (t, 2H, J=6.58 Hz), 2.66 (q, 2H, J=7.02 Hz), 2.89 (t, 2H, J=6.58 Hz), 3.69 (s, 3H).

1-Ethyl-1,3,4,9-tetrahydro-indeno[2,1-b]pyridin-2-one

3-Ethylamino-propionic acid methyl ester (2.41 g, 18.4 mmol) is added to a solution of 2-indanone (2.3 g, 17.33 mmol) in toluene (27 mL), and the reaction is brought to reflux for 2 hours. Toluene is removed in vacuo and the residue is dissolved in ethylene glycol (23 mL) and the resulting solution is heated to reflux for 8 hours. The reaction is allowed to cool to ambient temperature and is poured over water and extracted with dichloromethane. The organic phase is dried over magnesium sulfate and concentrated in vacuo to afford the crude title compound. The crude product is purified by silica gel chromatography (gradient of ethyl acetate in hexanes 10-100%) affording 1 g (27% yield) of the title compound. MS (m/z): 213.3 (M+1).

2-Chloro-5-(1-ethyl-2-oxo-2,3,4,9-tetrahydro-1H-indeno[2,1-b]pyridine-7-carbonyl)-benzenesulfonamide Under nitrogen, aluminum chloride (0.7 g, 4.9 mmol) is slurried in dichloromethane (15 mL) then 4-chloro-3-sulfamoyl-benzoyl chloride (287 mg, 1.13 mmol) is added and allowed to stir at ambient temperature for 30 minutes. Then 1-ethyl-1,3,4,9-tetrahydro-indeno[2,1-b]pyridin-2-one (240 mg, 1.13 mmol) is added in 4 mL dichloromethane. The reaction is allowed to stir at ambient temperature for 1.5 hours. The reaction mixture is poured over ice-water and extracted with dichloromethane, the organic layer is separated and concentrated to give crude title compound as a brown oil. Recrystallization from warm dichloromethane afforded the title compound as a yellow powder (125 mg, 26% yield). ¹H NMR (MeOD) δ 1.26 (t, 2H, J=7.01 Hz), 2.76-2.83 (m, 4H), 3.6 (s, 2H), 3.77 (q, 2H, J=7.01), 5.19 (s, 2H), 7.19 (d, 1H, J=8.11 Hz), 7.68-7.73 (m, 2H), 7.86 (d, 1H, J=1.09), 7.94 (dd, 1H, J=2.19, 8.11 Hz), 8.46 (d, 1H, J=1.97 Hz). MS (m/z): 431 (M+1).

Example 40

2-Chloro-5-[4-(2,5-dimethyl-pyrrol-1-yl)-3-fluoro-benzoyl]-benzenesulfonamide

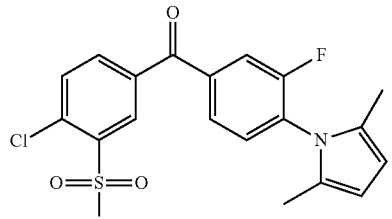

Following method B, 2-chloro-5-((4-(2,5-dimethyl-pyrrol-1-yl)-3-fluoro-phenyl)-hydroxy-methyl)-benzenesulfonamide is synthesized from the corresponding aryl bromide. In the next step, a solution of 100 mg of 2-chloro-5-((4-(2,5-dimethyl-pyrrol-1-yl)-3-fluoro-phenyl)-hydroxy-methyl)-benzenesulfonamide (0.24 mmol, 1 equivalent), 43 mg of 4-methylmorpholine N-oxide, and 122 mg of 4 Å molecular sieves in 5 mL of dichloromethane is stirred at room temperature as 5 mg of tetrapropylammonium perruthenate is added. The reaction is stirred at room temperature for 1 h, then filtered through a pad of silica gel, eluted with ethyl acetate and concentrated in vacuo. After purification by flash chromatography, 45 mg of product is obtained. ¹H NMR (400 MHz, CDCl₃): δ 2.05 (s, 6H), 5.20 (s, 2H), 6.0 (s, 2H), 7.40 (t, 1H, J=8 Hz), 7.65-7.75 (m, 3H), 8.05 (dd, 1H, J=8 Hz), 8.55 (d, 1H, J=2 Hz). MS (m/z): 407 (M+1).

Example 41

2-Chloro-5-(1H-indole-6-carbonyl)-benzenesulfonamide

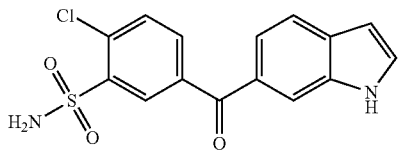 [SMILES: NS(=O)(=O)c1cc(C(=O)c2ccc3cc[nH]c3c2)ccc1Cl]

A dispersion of potassium hydride in oil (33.15 mmol) is washed with hexanes under argon then tetrahydrofuran (310 mL) is added at 0° C. and the resulting suspension is treated by dropwise addition of 6.77 g of 6-bromoindole in tetrahydrofuran (61 mL). The reaction mixture is stirred at 0° C. for 15 min to give a yellow solution. A solution of 44.2 mL of tert-butyllithium (1.5 M in pentane) is added slowly at −78° C. while maintaining the temperature below −75° C. to produce a yellow suspension. After 15 min a solution of 3.08 g of 4-chloro-N-methoxy-N-methyl-3-sulfamoyl-benzamide in tetrahydrofuran (61 mL) is added and the temperature is allowed to increase slowly to 0° C. The reaction mixture is quenched by addition of 62 mL of saturated aqueous ammonium chloride and extracted with ethyl ether. The organics were washed with water, dried over magnesium sulfate and concentrated to 9.65 g of a brown oil which is chromatographed on silica gel (1:1 hexanes/ethyl acetate) to give 2-chloro-5-(1H-indole-6-carbonyl)-benzenesulfonamide as a yellow foam. MS (m/z): 333 (M−1); Rf 0.37 (1:1 hexanes/ethyl acetate).

Example 42

2-Fluoro-5-(1H-indole-6-carbonyl)-benzenesulfonamide

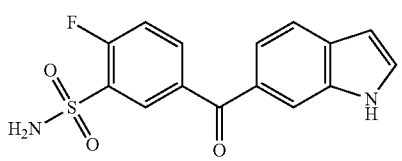 [SMILES: NS(=O)(=O)c1cc(C(=O)c2ccc3cc[nH]c3c2)ccc1F]

A solution of 0.997 g of 6-bromoindole in tetrahydrofuran (20 mL) is cooled to −50° C. and treated by slow addition of 8.79 mL of tert-butyllithium (1.5 M in pentane). After 2 h at −50° C. the reaction mixture is treated with 0.4 g of 4-fluoro-N-methoxy-N-methyl-3-sulfamoyl-benzamide in tetrahydrofuran (10 mL), stirred for an additional 3 h at −50° C. and quenched by addition of 2 mL of saturated aqueous ammonium chloride. The reaction mixture is taken up in ethyl acetate, washed with a saturated sodium chloride solution and dried (magnesium sulfate). After concentration in vacuo the residue is purified by silica gel chromatography (1:1 hexanes/ethyl acetate) to give 2-fluoro-5-(1H-indole-6-carbonyl)-benzenesulfonamide as an amorphous solid. MS (m/z): 317 (M−1); Rf 0.32 (1:1 hexanes/ethyl acetate).

Example 43

5-(1H-Indole-6-carbonyl)-2-methyl-benzenesulfonamide

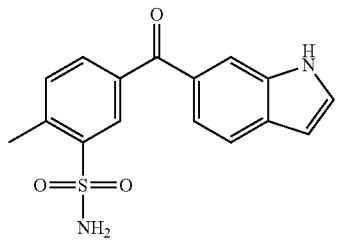 [SMILES: Cc1ccc(C(=O)c2ccc3cc[nH]c3c2)cc1S(N)(=O)=O]

5-(1H-Indole-6-carbonyl)-2-methyl-benzenesulfonamide is prepared from 4 g of N-methoxy-4,N-dimethyl-3-sulfamoyl-benzamide according to the procedure described in Method C. MS (m/z): 313 (M−1); Rf 0.28 (1:1 hexanes/ethyl acetate).

Preparation of N-methoxy-4,N-dimethyl-3-sulfamoyl-benzamide

A mixture of 3.63 g of 4-methyl-3-sulfamoyl-benzoic acid, 1.92 g of N,O-dimethylhydroxylaminehydrochloride, and 5.02 mL of triethylamine in methylene chloride (120 mL) is treated with 8.32 g of benzotriazole-1-yl-oxy-tris-(dimethylamino)-phosphonium hexafluorophosphate. The reaction mixture is stirred overnight at room temperature, washed sequentially with saturated aqueous sodium bicarbonate, water and a saturated sodium chloride solution, dried (magnesium sulfate) and concentrated in vacuo. The crude material is purified by silica gel chromatography (1:2 hexanes/ethyl acetate) to give N-methoxy-4,N-dimethyl-3-sulfamoyl-benzamide as a white powder. MS (m/z): 257 (M−1); Rf 0.25 (1:2 hexanes/ethyl acetate).

Example 44

3-(1H-Indole-6-carbonyl)-benzenesulfonamide

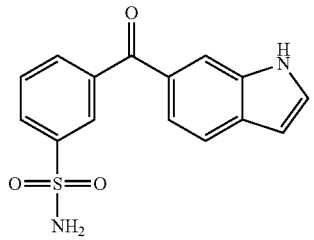 [SMILES: NS(=O)(=O)c1cccc(C(=O)c2ccc3cc[nH]c3c2)c1]

3-(1H-Indole-6-carbonyl)-benzenesulfonamide is prepared from 2.95 g of N-methoxy-N-methyl-3-sulfamoyl-benzamide according to the procedure described in method C. MS (m/z): 299 (M−1); Rf 0.25 (1:1 hexanes/ethyl acetate).

Preparation of
N-methoxy-N-methyl-3-sulfamoyl-benzamide

N-Methoxy-N-methyl-3-sulfamoyl-benzamide is prepared from 3.14 g of 3-sulfamoyl-benzoic acid according to the procedure described in method C. MS (m/z): 243 (M−1); Rf 0.21 (1:2 hexanes/ethyl acetate).

Preparation of
4-fluoro-N-methoxy-N-methyl-3-sulfamoyl-benzamide

4-Fluoro-N-methoxy-N-methyl-3-sulfamoyl-benzamide is prepared from 0.5 g of 4-fluoro-3-sulfamoyl-benzoic acid according to the procedure described in method C. MS (m/z): 261 (M−1); Rf 0.45 (9:1 methylene chloride/methanol).

Example 45

2-chloro-5-(3-phenyl-1H-indole-6-carbonyl)-benzenesulfonamide

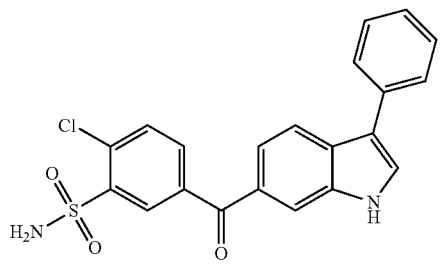 [SMILES: NS(=O)(=O)c1cc(C(=O)c2ccc3c(-c4ccccc4)c[nH]c3c2)ccc1Cl]

Method for the preparation of 5-[3-bromo-1-(tert-butyldimethylsilyl)-1H-indole-6-carbonyl]-2-chloro-N-(tert-butyldimethylsilyl)-benzenesulfonamide Step 1:
A solution of 3.89 g of 2-chloro-5-(1H-indole-6-carbonyl)-benzenesulfonamide in tetrahydrofuran (370 mL) is cooled to −78° C. and treated by dropwise addition of n-butyllithium in hexane (1.6 M, 24.4 mL). After 15 min at −78° C. the orange solution is treated by addition of 3.47 g of tert-butyldimethylchlorosilane in tetrahydrofuran (50 mL) and the temperature is allowed to increase slowly to 0° C. After 1.5 h at 0° C. the reaction mixture is treated with water at 0° C. and extracted with diethyl ether. The organic phase is washed with a saturated sodium chloride solution, dried (magnesium sulfate) and concentrated to an oil which is triturated under sonication in diisopropylether to give 5-[1-(tert-butyldimethylsilyl)-1H-indole-6-carbonyl]-2-chloro-N-(tert-butyldimethylsilyl)-benzenesulfonamide as a white powder. MS (m/z): 563 (M+1), Rf 0.60 (2:1 hexanes/ethyl acetate).

Step 2:
A solution of 1.7 g of 5-[1-(tert-butyldimethylsilyl)-1H-indole-6-carbonyl]-2-chloro-N-(tert-butyldimethylsilyl)-benzenesulfonamide in tetrahydrofuran (110 mL) at −78° C. is treated with 0.564 g of N-bromosuccinimide. After 6 h at −78° C. the temperature is allowed to reach room temperature. The reaction mixture is taken up in diethyl ether, washed with water and dried (magnesium sulfate). The solvent is evaporated and the residue is triturated under sonication with diisopropylether to give 5-[3-bromo-1-(tert-butyldimethylsilyl)-1H-indole-6-carbonyl]-2-chloro-N-(tert-butyldimethylsilyl)-benzenesulfonamide as a tan powder. MS (m/z): 643 (M+1); Rf 0.90 (95:5 methylene chloride/methanol).

2-chloro-5-(3-phenyl-1H-indole-6-carbonyl)-benzenesulfonamide

To a mixture of 0.1 g of 5-[3-bromo-1-(tert-butyl-dimethyl-silyl)-1H-indole-6-carbonyl]-2-chloro-N-(tert-butyl-dimethyl-silyl)-benzenesulfonamide, 0.039 g of phenylboronic acid and 0.025 g of 1,1′-bis(diphenylphosphino)-ferrocenedichloropalladium(II)-dichloromethane complex in dimethoxyethane (3.6 mL) is added 0.099 g of tri-potassium phosphate in water (1.2 mL). The solution is heated to 130° C. for 5 minutes (microwave irradiation). The reaction mixture is extracted with ethyl acetate. The organic phase is washed with water, dried (magnesium sulfate) and concentrated to 0.094 g of crude product. Purification via flash chromatography on silica gel (98:2 methylene chloride/methanol) afforded 2-chloro-5-(3-phenyl-1H-indole-6-carbonyl)-benzenesulfonamide as a tan powder. MS (m/z): 409 (M−1); Rf 0.22 (95:5:0.5 methylene chloride/methanol/ammonium hydroxide).

Likewise the following compounds are prepared from 5-[3-bromo-1-(tert-butyl-dimethyl-silyl)-1H-indole-6-carbonyl]-2-chloro-N-(tert-butyl-dimethyl-silyl)-benzenesulfonamide.

2-Chloro-5-[3-(4-methoxy-phenyl)-1H-indole-6-carbonyl]-benzenesulfonamide
MS (m/z): 439 (M−1); Rf 0.22 (95:5 methylene chloride/methanol).

2-Chloro-5-[3-(4-fluoro-phenyl)-1H-indole-6-carbonyl]-benzenesulfonamide
MS (m/z): 427 (M−1); Rf 0.16 (3:1 methylene chloride/diethyl ether).

5-[3-(3-Acetyl-phenyl)-1H-indole-6-carbonyl]-2-chloro-benzenesulfonamide
MS (m/z): 452 (M−1); Rf 0.18 (3:1 methylene chloride/diethyl ether).

5-[3-(4-Acetyl-phenyl)-1H-indole-6-carbonyl]-2-chloro-benzenesulfonamide
MS (m/z): 451 (M−1); Rf 0.16 (3:1 methylene chloride/diethyl ether).

2-Chloro-5-[3-(3-methanesulfonyl-phenyl)-1H-indole-6-carbonyl]-benzenesulfonamide
MS (m/z): 487 (M−1); Rf 0.11 (1:1 methylene chloride/diethyl ether).

2-Chloro-5-[3-(4-methanesulfonyl-phenyl)-1H-indole-6-carbonyl]-benzenesulfonamide
MS (m/z): 487 (M−1); Rf 0.09 (2:1 methylene chloride/diethyl ether).

2-Chloro-5-[3-(4-ethanesulfonyl-phenyl)-1H-indole-6-carbonyl]-benzenesulfonamide
MS (m/z): 501 (M−1); Rf 0.12 (3:1 methylene chloride/diethyl ether).

5-(3-Biphenyl-4-yl-1H-indole-6-carbonyl)-2-chloro-benzenesulfonamide
MS (m/z): 485 (M−1); Rf 0.19 (95:5:0.5 methylene chloride/methanol/ammonium hydroxide).

2-Chloro-5-(3-thiophen-3-yl-1H-indole-6-carbonyl)-benzenesulfonamide
MS (m/z): 415 (M−1); Rf 0.23 (3:1 methylene chloride/diethyl ether).

5-[3-(5-Acetyl-thiophen-2-yl)-1H-indole-6-carbonyl]-2-chloro-benzenesulfonamide
MS (m/z): 451 (M−1); Rf 0.16 (3:1 methylene chloride/diethyl ether).

5-(1H,1'H-[3,5']Biindolyl-6-carbonyl)-2-chloro-benzenesulfonamide

MS (m/z): 447 (M−1); Rf 0.22 (3:1 methylene chloride/diethyl ether).

2-Chloro-5-(3-pyridin-3-yl-1H-indole-6-carbonyl)-benzenesulfonamide

MS (m/z): 410 (M−1); Rf 0.23 (90:10:1 methylene chloride/methanol/ammonium hydroxide).

2-Chloro-5-(3-pyrimidin-5-yl-1H-indole-6-carbonyl)-benzenesulfonamide

MS (m/z): 411 (M−1); Rf 0.08 (95:5:0.5 methylene chloride/methanol/ammonium hydroxide).

2-Chloro-5-{3-[4-(morpholine-4-carbonyl)-phenyl]-1H-indole-6-carbonyl}-benzenesulfonamide MS (m/z): 522 (M−1); Rf 0.12 (95:5 methylene chloride/methanol).

2-Chloro-5-[3-(3,5-dimethyl-isoxazol-4-yl)-1H-indole-6-carbonyl]-benzenesulfonamide MS (m/z): 428 (M−1); Rf 0.13 (3:1 methylene chloride/diethyl ether).

2-Chloro-5-[3-(5-chloro-2-methoxy-pyridin-4-yl)-1H-indole-6-carbonyl]-benzenesulfonamide MS (m/z): 474 (M−1); Rf 0.21 (3:1 methylene chloride/diethyl ether).

2-Chloro-5-(3-pyridin-4-yl-1H-indole-6-carbonyl)-benzenesulfonamide

MS (m/z): 410 (M−1); Rf 0.26 (90:10:1 methylene chloride/methanol/ammonium hydroxide).

2-Chloro-5-[3-(2-chloro-pyridin-4-yl)-1H-indole-6-carbonyl]-benzenesulfonamide

MS (m/z): 444 (M−1); Rf 0.08 (95:5:0.5 methylene chloride/methanol/ammonium hydroxide).

Example 46

2-Chloro-5-[3-(2-methyl-pyridin-4-yl)-1H-indole-6-carbonyl]-benzenesulfonamide

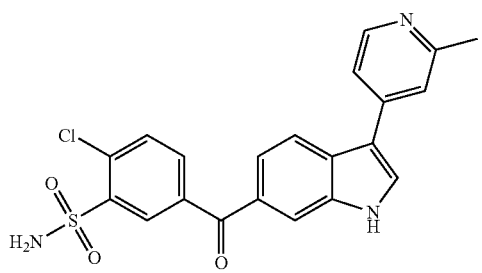 [SMILES: Cc1cc(-c2c[nH]c3cc(C(=O)c4ccc(Cl)c(S(N)(=O)=O)c4)ccc23)ccn1]

To a mixture of 0.1 g of 5-[3-bromo-1-(tert-butyl-dimethyl-silyl)-1H-indole-6-carbonyl]-2-chloro-N-(tert-butyl-dimethyl-silyl)-benzenesulfonamide, 0.095 g of crude (2-methyl-4-pyridinyl)-boronic acid and 0.025 g of 1,1'-bis(diphenylphosphino)-ferrocenedichloropalladium(II)-dichloromethane complex in dimethoxyethane (3.6 mL) is added 0.099 g of tri-potassium phosphate in water (1.2 mL). The solution is heated to 130° C. for 5 minutes (microwave irradiation). The reaction mixture is extracted with ethyl acetate. The organic phase is washed with water, dried over magnesium sulfate and concentrated to 0.071 g of crude product. Purification via flash chromatography on silica gel (95:5:0.5 methylene chloride/methanol/ammonium hydroxide) afforded 2-chloro-5-[3-(2-methyl-pyridin-4-yl)-1H-indole-6-carbonyl]-benzenesulfonamide as a tan powder. MS (m/z): 424 (M−1); Rf 0.06 (95:5:0.5 methylene chloride/methanol/ammonium hydroxide).

Preparation of (2-methyl-4-pyridinyl)-boronic acid

Step 1:

A suspension of 10 g of 4-bromopyridine hydrochloride in tetrahydrofuran (180 mL) is treated at −78° C. with 48.2 mL of methylmagnesium chloride (3 M in tetrahydrofuran). After 25 min at −78° C. the reaction mixture is treated by slow addition of a solution of 7.69 mL of phenyl chloroformate in tetrahydrofuran (20 mL) resulting in an increase of the reaction temperature to room temperature. The reaction mixture is stirred at room temperature for 10 min and then treated by addition of a saturated aqueous solution of ammonium chloride (84 mL) at 0° C. followed by diethyl ether. The organic phase is washed with water, 2 N aqueous HCl, water and a saturated sodium chloride solution, dried over magnesium sulfate and concentrated in vacuo to 17.1 g of carbamate as an orange oil. This material is taken up in toluene (200 mL) and treated with a solution of 15.64 g of o-chloranil in acetic acid (117 mL). After 26 h at room temperature the resulting solution is treated with 30% aqueous sodium hydroxide. The resulting emulsion is filtered through Celite. Phases are separated and extracted with toluene. The organics are washed with water and extracted with 2 N HCl. Acidic extracts are washed with diethyl ether, treated with 30% aqueous sodium hydroxide at 0° C. and extracted with methylene chloride. The organic extracts are dried (magnesium sulfate), concentrated and purified by silica gel chromatography (1:1 methylene chloride/diethyl ether) to give 4-bromo-2-methyl-pyridine as an oil. MS (m/z): 174 (M+1); Rf 0.31 (1:1 methylene chloride/diethyl ether).

Step 2:

A solution of 4.7 mL of n-butyllithium (1.6 M in hexane) in diethyl ether (20 mL) is cooled to −78° C. and treated with a solution of 1.07 g of 4-bromo-2-methyl-pyridine in diethyl ether (10 mL) previously dried over molecular sieves at 40° C. overnight. After 20 min at −78° C. the resulting orange suspension is treated with 1.87 mL of triisopropylborate and the temperature is allowed to increase to room temperature over a 2 h period. After an additional 2 h the reaction mixture is treated with water. The organic phase is extracted with 0.5 N sodium hydroxide. Extracts are washed with diethyl ether and acidified with 2 N HCl to pH 6. The resulting suspension is concentrated under vacuum to give a paste containing (2-methyl-4-pyridinyl)-boronic acid which is used without further purification for the Suzuki coupling. MS (m/z): 136 (M−1).

Likewise the following compounds are prepared from 5-[3-bromo-1-(tert-butyl-dimethyl-silyl)-1H-indole-6-carbonyl]-2-chloro-N-(tert-butyl-dimethyl-silyl)-benzenesulfonamide and the corresponding boronic acids 2-Chloro-5-[3-(2-ethyl-pyridin-4-yl)-1H-indole-6-carbonyl]-benzenesulfonamide MS (m/z): 438 (M−1); Rf 0.10 (95:5:0.5 methylene chloride/methanol/ammonium hydroxide).

Preparation of (2-ethyl-4-pyridinyl)-boronic acid (2-Ethyl-4-pyridinyl)-boronic acid is prepared from 5 g of 4-bromopyridine hydrochloride according to the procedure described in example 46, step 1 and step 2. MS (m/z): 150 (M−1).

2-Chloro-5-[3-(2-cyclopropyl-pyridin-4-yl)-1H-indole-6-carbonyl]-benzenesulfonamide MS (m/z): 450 (M−1); Rf 0.13 (95:5:0.5 methylene chloride/methanol/ammonium hydroxide).

(2-cyclopropyl-4-pyridinyl)-boronic acid:

(2-Cyclopropyl-4-pyridinyl)-boronic acid is prepared from 5 g of 4-bromopyridine hydrochloride according to the procedure described in example 46, step 1 and step 2. MS (m/z): 162 (M−1).

2-Chloro-5-{3-[2-(3-methoxy-propyl)-pyridin-4-yl]-1H-indole-6-carbonyl}-benzenesulfonamide MS (m/z): 482 (M−1); Rf 0.07 (95:5:0.5 methylene chloride/methanol/ammonium hydroxide).

[2-(3-methoxy-propyl)-4-pyridinyl]-boronic acid:

[2-(3-Methoxy-propyl)-4-pyridinyl]-boronic acid is prepared from 1.35 g of 4-bromopyridine hydrochloride according to the procedure described in example 46, step 1 and step 2. MS (m/z): 196 (M+1).

2-Chloro-5-{3-[2-(3-morpholin-4-yl-propyl)-pyridin-4-yl]-1H-indole-6-carbonyl}-benzenesulfonamide MS (m/z): 539 (M+1); Rf 0.15 (90:10:1 ethyl acetate/methanol/ammonium hydroxide).

[2-(3-morpholin-4-yl-propyl)-4-pyridinyl]-boronic acid:

[2-(3-morpholin-4-yl-propyl)-4-pyridinyl]-boronic acid is prepared from 5.36 g of 4-bromopyridine hydrochloride according to the procedure described in example 46, step 1 and step 2. MS (m/z): 251 (M+1).

2-Chloro-5-{3-[2-(2-dimethylamino-ethoxy)-pyridin-4-yl]-1H-indole-6-carbonyl}-benzenesulfonamide MS (m/z): 497 (M−1); Rf 0.2 (90:10:1 ethyl acetate/methanol/ammonium hydroxide).

Example 47

Preparation of [2-(2-dimethylamino-ethoxy)-4-pyridinyl]-boronic acid

Step 1:

A mixture of 5.55 g of sodium and 26.9 mL of 2-dimethylaminoethanol in tetrahydrofuran (180 mL) is heated to reflux for 20 hours. The reaction mixture is cooled to room temperature, treated with 4 g of 4-amino-2-chloropyridine and heated to 140° C. for 20 min (microwave irradiation). The reaction mixture is treated with concentrated HCl to pH 8 at 0° C., saturated with sodium chloride and extracted with diethyl ether. The organics are dried (magnesium sulfate) and concentrated to 11.9 g of crude product which is purified by silica gel chromatography (90:10:1 ethyl acetate/methanol/ammonium hydroxide) to give 2-(2-dimethylamino-ethoxy)-pyridin-4-ylamine as tan crystals. MS (m/z): 182 (M+1); Rf 0.1 (90:10:1 ethyl acetate/methanol/ammonium hydroxide).

Step 2:

A mixture of 1.2 g of 2-(2-dimethylamino-ethoxy)-pyridin-4-ylamine, 0.749 g of sodium bromide and 1.16 g of copper sulfate is cooled to 0° C. and treated with 12 mL of 9 M sulfuric acid with stirring. The resulting dark suspension is treated at 0° C. with a solution of 0.503 g of sodium nitrite in water (0.8 mL) and stirred at 0° C. for 1.5 h and at room temperature for 1.5 h. The reaction mixture is pored onto ice-water, brought to basic pH with 30% sodium hydroxide, and extracted with methylene chloride. The organics are dried (magnesium sulfate), concentrated and purified by silica gel chromatography (7:3 ethyl acetate/methanol) to give [2-(4-bromo-pyridin-2-yloxy)-ethyl]-dimethyl-amine as an oil. MS (m/z): 245 (M+1); Rf 0.25 (7:3 ethyl acetate/methanol).

Step 3:

[2-(2-Dimethylamino-ethoxy)-4-pyridinyl]-boronic acid is prepared from 0.713 g of [2-(4-bromo-pyridin-2-yloxy)-ethyl]-dimethyl-amine according to the procedure described in Example 6 step 2. MS (m/z): 211 (M+1).

The Following Compound can be Prepared with Similar Steps.

2-Chloro-5-{3-[2-(2-morpholin-4-yl-ethoxy)-pyridin-4-yl]-1H-indole-6-carbonyl}-benzenesulfonamide.

MS (m/z): 539 (M−1); Rf 0.38 (90:10:1 ethyl acetate/methanol/ammonium hydroxide).

Preparation of [2-(2-morpholin-4-yl-ethoxy)-4-pyridinyl]-boronic acid

[2-(2-Morpholin-4-yl-ethoxy)-4-pyridinyl]-boronic acid is prepared from N-(2-hydroxyethyl)-morpholine according to the procedure described for the preparation of [2-(2-dimethylamino-ethoxy)-4-pyridinyl]-boronic acid. MS (m/z): 253 (M+1).

Example 48

2-Methyl-5-[3-(2-methyl-pyridin-4-yl)-1H-indole-6-carbonyl]-benzenesulfonamide

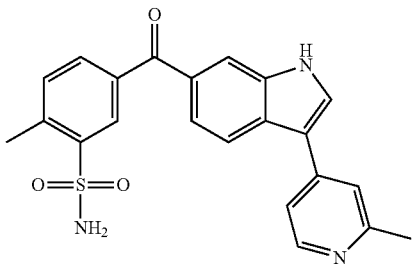

2-Methyl-5-[3-(2-methyl-pyridin-4-yl)-1H-indole-6-carbonyl]-benzenesulfonamide is prepared from 0.25 g of 5-[3-bromo-1-(tert-butyl-dimethyl-silyl)-1H-indole-6-carbonyl]-N-(tert-butyl-dimethyl-silyl)-2-methyl-benzenesulfonamide according to the procedure described in Example 6 (microwave irradiation at 150° C. for 5 min). MS (m/z): 404 (M−1); Rf 0.19 (90:10:1 methylene chloride/methanol/ammonium hydroxide).

Preparation of 5-[3-bromo-1-(tert-butyl-dimethyl-silyl)-1H-indole-6-carbonyl]-N-(tert-butyl-dimethyl-silyl)-2-methyl-benzenesulfonamide Step 1:

5-[1-(tent-Butyldimethylsilyl)-1H-indole-6-carbonyl]-N-(tert-butyldimethylsilyl)-2-methyl-benzenesulfonamide is prepared from 3.09 g of 5-(1H-indole-6-carbonyl)-2-methyl-benzenesulfonamide according to the procedure described in Example 5, step 1. MS (m/z): 543 (M+1); Rf 0.75 (2:1 hexanes/ethyl acetate).

Step 2:

5-[3-Bromo-1-(tert-butyldimethylsilyl)-1H-indole-6-carbonyl]-N-(tert-butyldimethylsilyl)-2-methyl-benzenesulfonamide is prepared from 3.21 g of 5-[1-(tert-butyldimethylsilyl)-1H-indole-6-carbonyl]-N-(tert-butyldimethylsilyl)-2-methyl-benzenesulfonamide according to the procedure described in Example 5, step 2. MS (m/z): 622 (M+1); Rf 0.77 (95:5 methylene chloride/methanol).

Example 49

3-[3-(2-Methyl-pyridin-4-yl)-1H-indole-6-carbonyl]-benzenesulfonamide

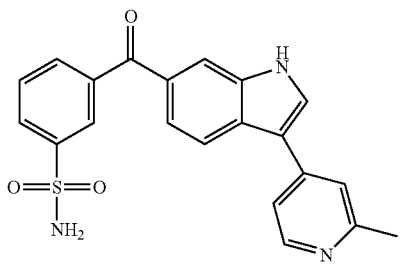 [SMILES: Cc1cc(-c2c[nH]c3cc(C(=O)c4cccc(S(N)(=O)=O)c4)ccc23)ccn1]

3-[3-(2-Methyl-pyridin-4-yl)-1H-indole-6-carbonyl]-benzenesulfonamide is prepared from 0.25 g of 5-[3-bromo-1-(tert-butyl-dimethyl-silyl)-1H-indole-6-carbonyl]-N-(tert-butyl-dimethyl-silyl)-benzenesulfonamide according to the procedure described in Example 6 (microwave irradiation at 150° C. for 5 min). MS (m/z): 390 (M−1); Rf 0.19 (90:10:1 methylene chloride/methanol/ammonium hydroxide)

Preparation of 5-[3-bromo-1-(tert-butyl-dimethyl-silyl)-1H-indole-6-carbonyl]-N-(tert-butyl-dimethyl-silyl)-benzenesulfonamide Step 1:
5-[1-(tert-Butyldimethylsilyl)-1H-indole-6-carbonyl]-N-(tert-butyldimethylsilyl)-benzenesulfonamide is prepared from 1.857 g of 3-(1H-indole-6-carbonyl)-benzenesulfonamide according to the procedure described in example 45, step 1. MS (m/z): 529 (M+1); Rf 0.66 (2:1 hexanes/ethyl acetate).
Step 2:
5-[3-Bromo-1-(tert-butyldimethylsilyl)-1H-indole-6-carbonyl]-N-(tert-butyldimethylsilyl)-benzenesulfonamide is prepared from 1.14 g of 5-[1-(tert-butyldimethylsilyl)-1H-indole-6-carbonyl]-N-(tert-butyldimethylsilyl)-benzenesulfonamide according to the procedure described in example 45, step 2. MS (m/z): 607 (M+1); Rf 0.78 (95:5 methylene chloride/methanol).
Likewise the following compounds are prepared from 5-[3-bromo-1-(tert-butyl-dimethyl-silyl)-1H-indole-6-carbonyl]-N-(tert-butyl-dimethyl-silyl)-benzenesulfonamide and the corresponding boronic acids.
3-{3-[2-(3-Methoxy-propyl)-pyridin-4-yl]-1H-indole-6-carbonyl}-benzenesulfonamide
MS (m/z): 450 (M+1); Rf 0.22 (90:10:1 methylene chloride/methanol/ammonium hydroxide).
3-{3-[2-(3-Methoxy-propyl)-pyridin-4-yl]-1H-indole-6-carbonyl}-benzenesulfonamide
MS (m/z): 505 (M+1); Rf 0.10 (90:10:1 methylene chloride/methanol/ammonium hydroxide).

Example 50

The following compounds were prepared following method A using aluminum trichloride or other suitable aluminum reagents and the appropriate substituted phenyl moiety as illustrated by the following procedure.

5-Benzoyl-2-chloro-benzenesulfonamide

To a well stirred solution of 4-chloro-3-sulfamoyl-benzoyl chloride (0.5 g, 1.97 mmol) in 5 mL methylene chloride is added aluminum chloride (0.485 g, 1.85 mmol). After 30 min, benzene (1 mL, 5.72 mmol) is added and the reaction is stirred for 2 h at room temperature. The reaction mixture is then poured over ice, acidified with 6 N HCl and extracted three times with diethyl ether. The organic layers were combined, dried with magnesium sulfate, filtered and concentrated in vacuo. The resulting residue is purified via silica gel chromatography to yield 40 mg (69%) of the title compound as a tan solid. MS (m/z): 294 (M−1). Analytics calculated for $C_{13}H_{10}ClNO_3S$: C, 52.8; H, 3.41; N, 4.74. Found: C, 52.62; H, 3.21; N, 4.72.

2-Chloro-5-(4'-ethyl-biphenyl-4-carbonyl)-benzenesulfonamide

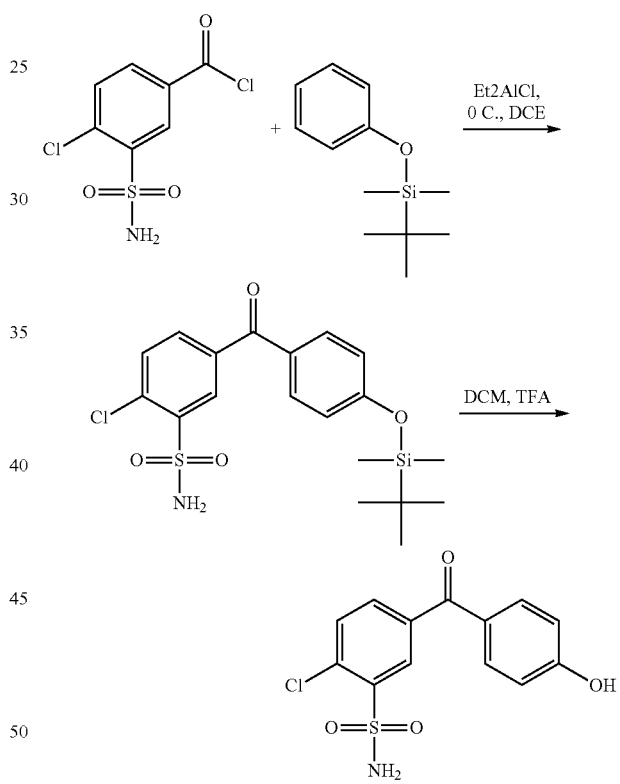

MS (m/z): 310 (M−1). Analytics calculated for $C_{13}H_{10}ClNO_4S$: C, 50.09; H, 3.23; N, 4.49. Found: C, 49.91; H, 3.18; N, 4.44.

2-Chloro-5-(4'-allyloxy-benzoyl)-benzenesulfonamide

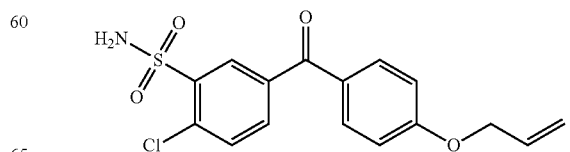

MS (M−1) 350.

85

5-(4-Bromo-benzoyl)-2-chloro-benzenesulfonamide

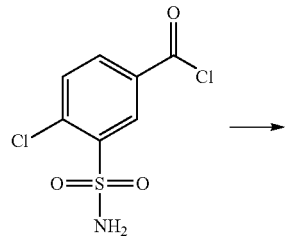

MS (m/z): 448 (M−1). Analytics calculated for $C_{13}H_9BrClNO_3S$: C, 41.68; H, 2.42; N, 3.74. Found: C, 41.69; H, 1.99; N, 3.56.

5-(4-tent-Butyl-benzoyl)-2-chloro-benzenesulfonamide

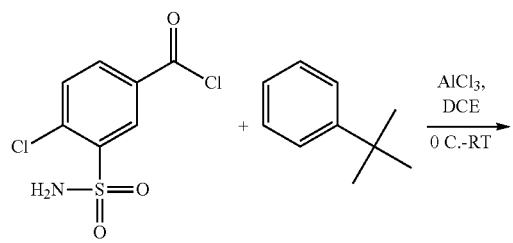

MS (m/z): 352 (M+1).

2-Chloro-5-(4-cyclopropyl-benzoyl)-benzenesulfonamide

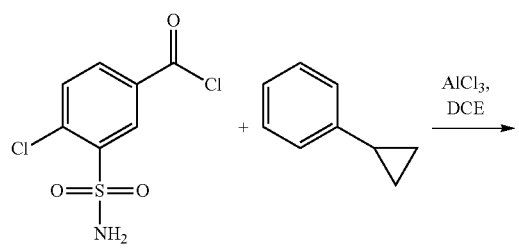

86

-continued

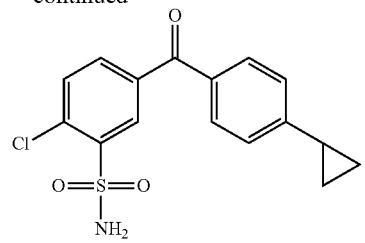

MS (m/z): 334 (M−1). Analytics calculated for $C_{16}H_{14}ClNO_3S$: C, 57.23; H, 4.2; N, 4.17. Found: C, 56.69; H, 4.13; N, 4.01.

2-Chloro-5-(4-cyclopentyl-benzoyl)-benzenesulfonamide

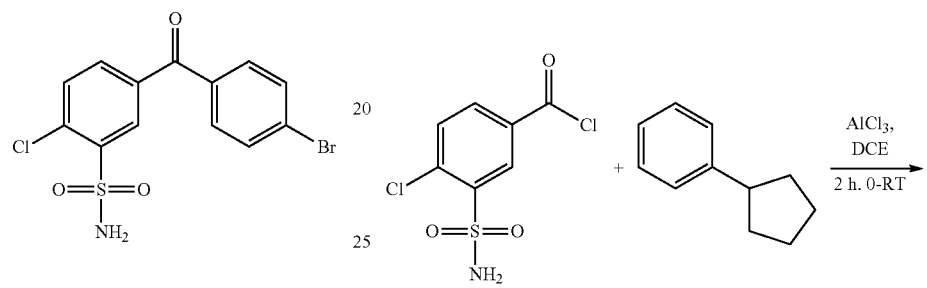

MS (m/z): 364 (M+1). Analytics calculated for $C_{18}H_{18}ClNO_3S$: C, 59.42; H, 4.99; N, 3.85. Found: C, 59.28; H, 4.76; N, 3.83.

2-Chloro-5-(4-cyclohexyl-benzoyl)-benzenesulfonamide

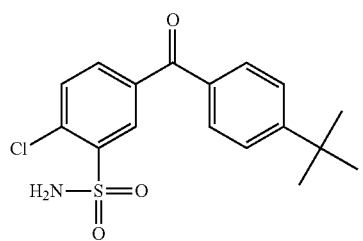

$^1$H NMR (400 MHz, DMSO): δ 1.3-1.8 (m, 1H), 2.6-2.7 (br, 1H), 7.4 (d, 2H, J=8 Hz), 7.70 (d, 2H, J=8 Hz), 7.80 (m, 3H), 7.88-7.92 (m, 1H), 8.28 (d, 1H, J=2 Hz). MS (m/z): 376 (M−1). Analytics calculated for $C_{19}H_{20}ClNO_3S$: C, 60.39; H, 5.33; N, 3.71. Found: C, 60.53; H, 5.08; N, 3.46.

87

2-Chloro-5-(4-cyano-benzoyl)-benzenesulfonamide

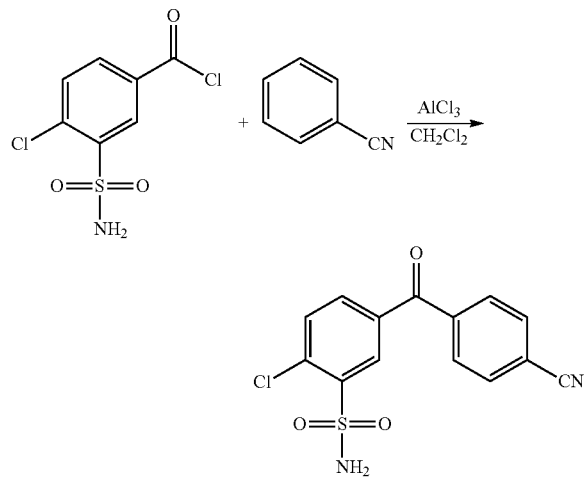

¹H NMR (400 MHz, CDCl₃): δ5.3 (br, 2H), 7.75 (d, 1H, J=8 Hz), 7.8-7.9 (m, 4H), 7.97 (m, 1H), 8.45 (d, 1H, J=2 Hz). MS (m/z): 319 (M−1).

5-(2-Bromo-4-methyl-benzoyl)-2-chloro-benzenesulfonamide

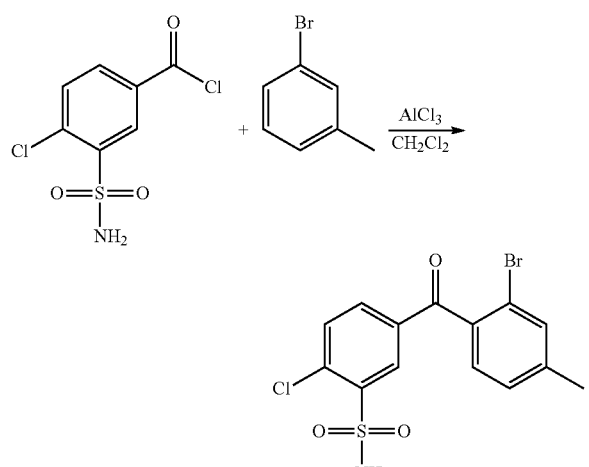

MS (m/z): 386 (M−1). Analytics calculated for $C_{14}H_{11}BrClNO_3S$: C, 43.26; H, 2.85; N, 3.6. Found: C, 43.19; H, 2.83; N, 3.60.

5-(4-Bromo-2-methyl-benzoyl)-2-chloro-benzenesulfonamide

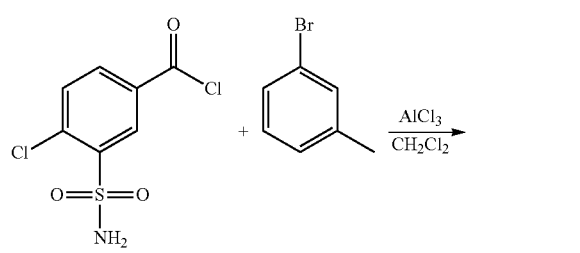

88

-continued

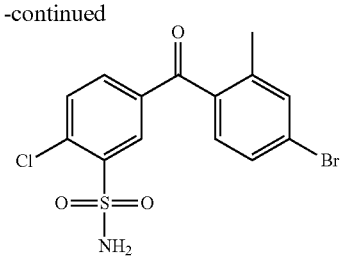

MS (m/z): 386 (M−1). Analytics calculated for $C_{14}H_{11}BrClNO_3S$: C, 43.26; H, 2.85; N, 3.6. Found: C, 43.07; H, 2.86; N, 3.60.

2-Chloro-5-(2-fluoro-4-methoxy-benzoyl)-benzenesulfonamide

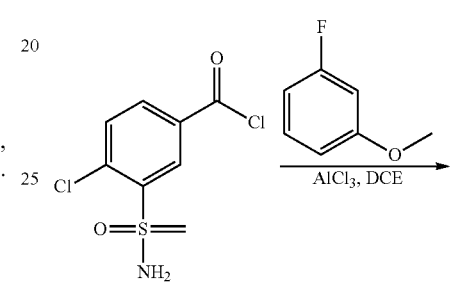

MS (m/z): 342 (M−1).

2-Chloro-5-(3-fluoro-4-hydroxy-benzoyl)-benzenesulfonamide

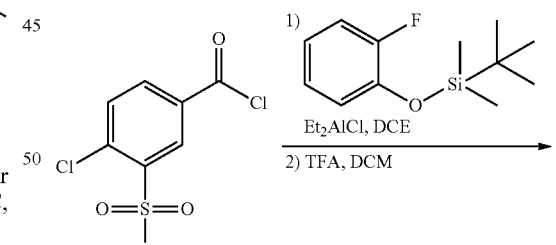

MS (m/z): 330 (M+1). Analytics calculated for $C_{13}H_9ClFNO_4S$: C, 47.35; H, 2.75; N, 4.25. Found: C, 47.47; H, 2.67; N, 4.07. M.P. 206-208° C.

89

2-Chloro-5-(2,4-dimethoxy-benzoyl)-benzenesulfonamide

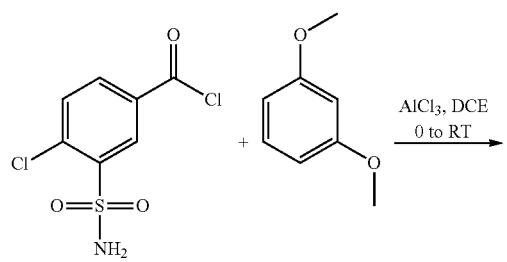

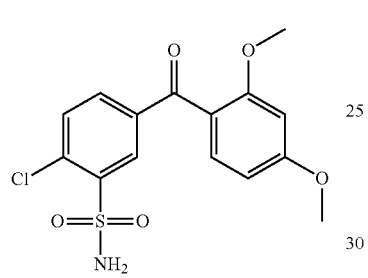

MS (m/z): 356 (M+1). Analytics calculated for $C_{15}H_{14}ClNO_5S$: C, 50.64; H, 3.97; N, 3.94. Found: C, 50.49; H, 3.72; N, 3.91.

2-Chloro-5-(2-fluoro-4-hydroxy-benzoyl)-benzenesulfonamide

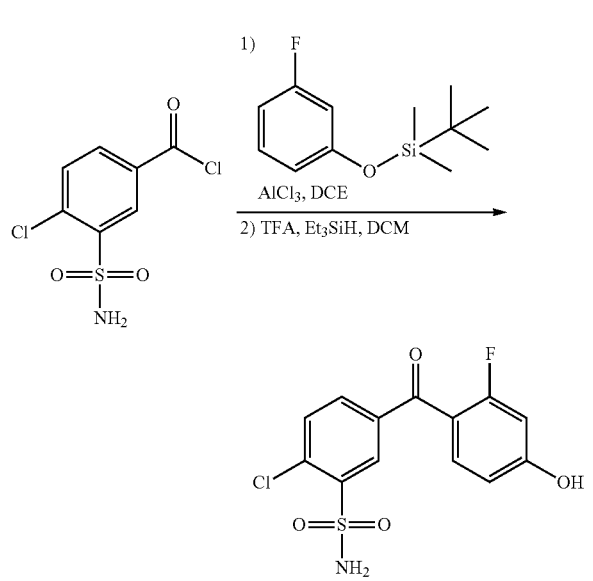

MS (m/z): 330 (M+1). Analytics calculated for $C_{13}H_9ClFNO_4S$: C, 47.35; H, 2.75; N, 4.25. Found: C, 47.36; H, 2.65; N, 3.99. M.P. 183-185° C.

90

5-(Biphenyl-4-carbonyl)-2-chloro-benzenesulfonamide

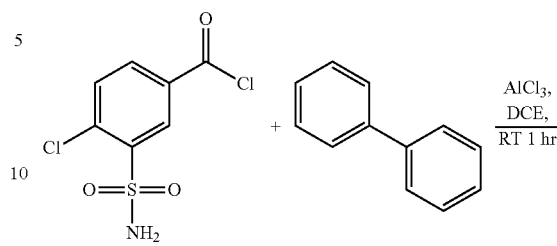

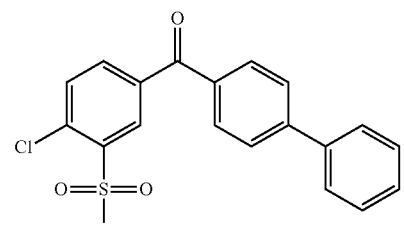

MS (m/z): 370 (M−1).

2-Chloro-5-(4'-methyl-biphenyl-4-carbonyl)-benzenesulfonamide

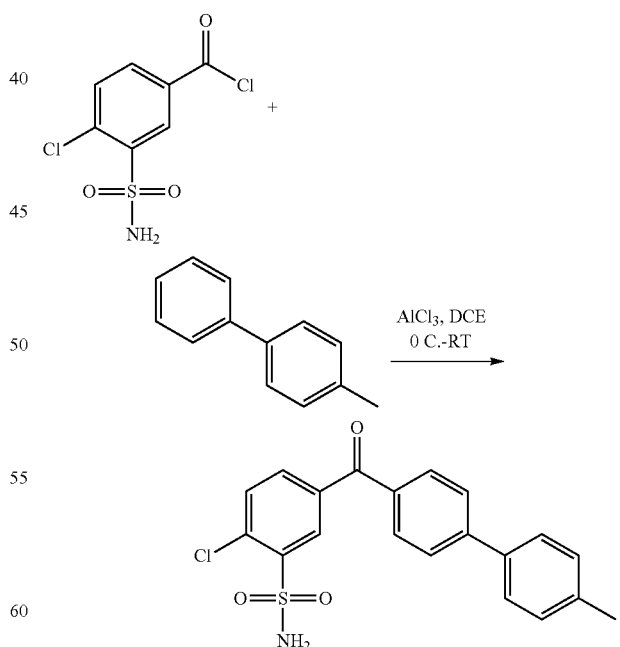

MS (m/z): 384 (M−1). Analytics calculated for $C_{20}H_{16}ClNO_3S$: C, 62.25; H, 4.18; N, 3.63. Found: C, 61.92; H, 3.91; N, 3.54.

91

2-Chloro-5-(2'-fluoro-biphenyl-4-carbonyl)-benzene-sulfonamide

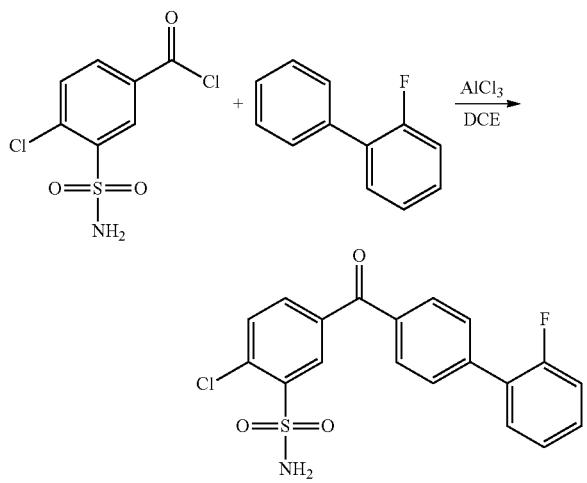

MS (m/z): 388 (M−1). Analytics calculated for $C_{19}H_{13}ClNO_3S$: C, 58.54; H, 3.36; N, 3.59. Found: C, 58.31; H, 3.50; N, 3.52.

2-Chloro-5-(4'-fluoro-biphenyl-4-carbonyl)-benzene-sulfonamide

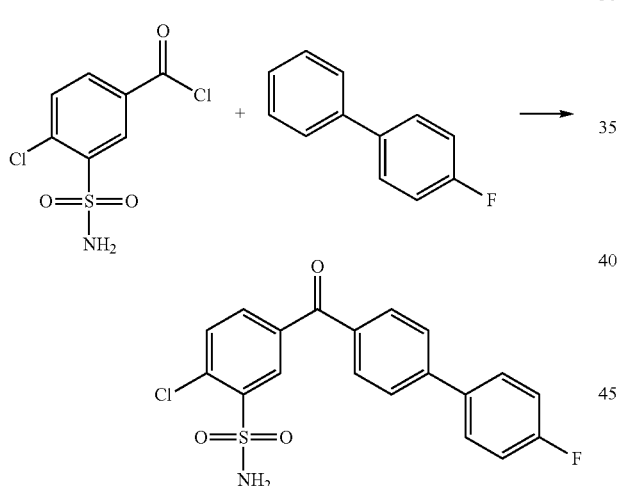

MS (m/z): 388 (M−1). Analytics calculated for $C_{19}H_{13}ClNO_3S$: C, 58.54; H, 3.36; N, 3.59. Found: C, 57.7; H, 3.23; N, 3.46.

2-Chloro-5-(4'-chloro-biphenyl-4-carbonyl)-benzene-sulfonamide

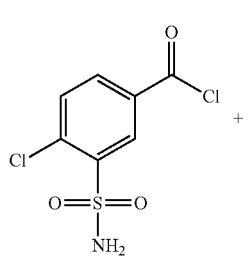

92

-continued

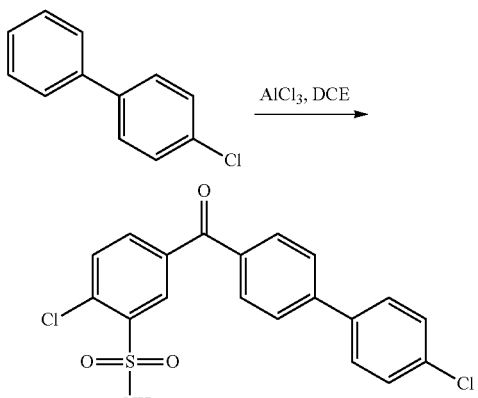

MS (m/z): 405 (M−1). Analytics calculated for $C_{19}H_{13}Cl_2NO_3S$: C, 56.17; H, 3.22; N, 3.45. Found: C, 55.99; H, 2.92; N, 3.41.

5-(3'-Bromo-biphenyl-4-carbonyl)-2-chloro-benzene-sulfonamide

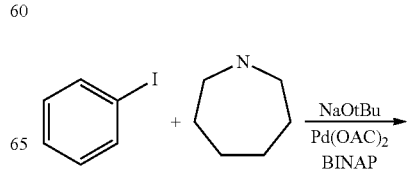

MS (m/z): 448 (M−1). Analytics calculated for $C_{19}H_{13}BrClNO_3S$: C, 50.63; H, 2.91; N, 3.11. Found: C, 50.58; H, 2.89; N, 2.86.

5-(4-Azepan-1-yl-benzoyl)-2-chloro-benzenesulfonamide

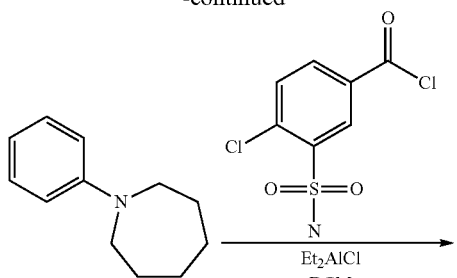

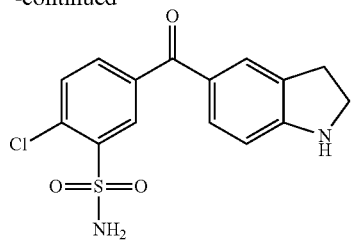

MS (m/z): 335 (M−1). Analytics calculated for $C_{15}H_{13}ClN2O_3S$: C, 53.49; H, 3.89; N, 8.32. Found: C, 53.50; H, 4.08; N, 7.34. M.P. 55-56

2-Chloro-5-(1H-indole-3-carbonyl)-benzenesulfonamide

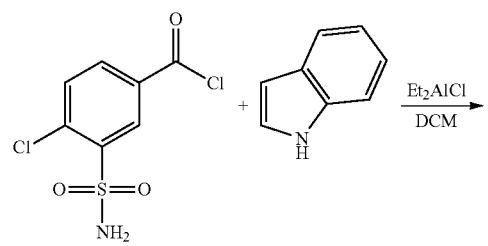

¹H NMR (400 MHz, CDCl₃): δ 1.57 (br, 4H), 1.80 (br, 4H), 3.55 (t, 4H, J=4 Hz), 5.18 (s, 2H), 6.90 (d, 2H, J=8 Hz), 7.66 (d, 1H, J=8 Hz), 7.70 (d, 2H, J=8 Hz), 7.88 (d, 1H, J=8 Hz), 8.43 (s, 1H). MS (m/z): 393 (M+1). Analytics calculated for $C_{19}H_{21}ClN2O_3S$: C, 58.08; H, 5.39; N, 7.13. Found: C, 58.10; H, 5.21; N, 6.89.

2-Chloro-5-(naphthalene-2-carbonyl)-benzenesulfonamide

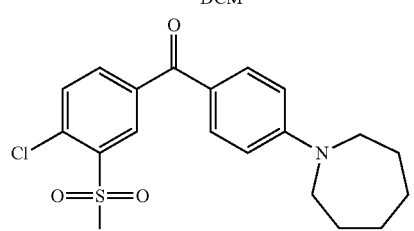

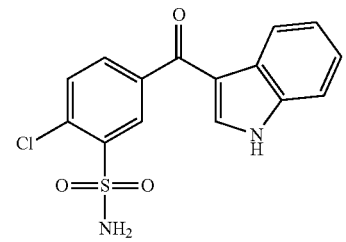

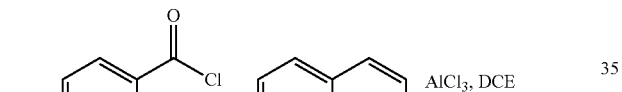

MS (m/z): (M−1) 344.

2-Chloro-5-(2,3-dihydro-1H-indole-5-carbonyl)-benzenesulfonamide

MS (m/z): 333 (M−1). Analytics calculated for $C_{15}H_{11}ClN2O_3S$: C, 53.82; H, 3.31; N, 8.37. Found: C, 53.84; H, 3.22; N, 8.31.

Example 51

The following analogs were prepared by method B unless otherwise noted.

2-Chloro-5-(3-methyl-benzoyl)-benzenesulfonamide

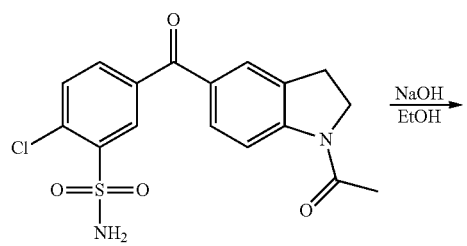

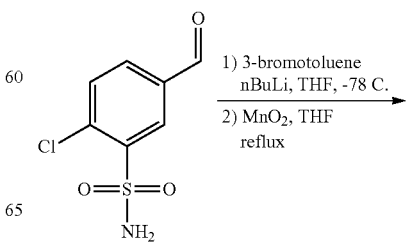

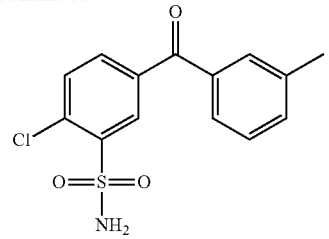

MS (m/z): 308 (M−1). Analytics calculated for C$_{14}$H$_{12}$ClNO$_3$S: C, 54.28; H, 3.9; N, 4.52. Found: C, 54.31; H, 3.67; N, 4.41.

2-Chloro-5-(4-trimethylsilanylethynyl-benzoyl)-benzenesulfonamide

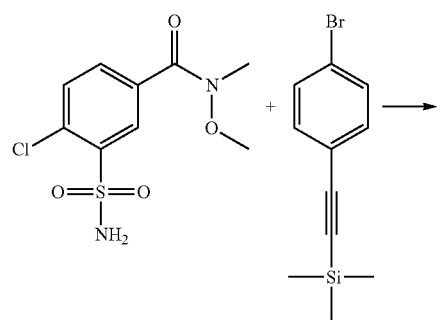

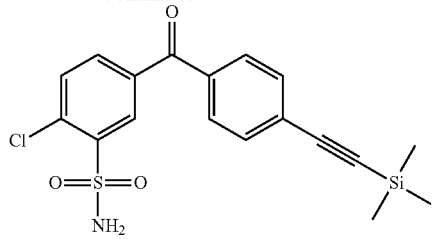

MS (m/z): 390 (M−1). Analytics calculated for C$_{18}$H$_{18}$ClNO$_3$SSi: C, 55.16; H, 4.63; N, 3.57. Found: C, 55.11; H, 4.43; N, 3.44. M.P. 206-208° C.

2-Chloro-5-(4-pyrrol-1-yl-benzoyl)-benzenesulfonamide

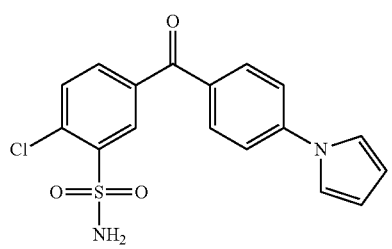 [SMILES: NS(=O)(=O)c1cc(C(=O)c2ccc(-n3cccc3)cc2)ccc1Cl]

$^1$H NMR (400 MHz, CDCl$_3$): δ 5.18 (s, 2H), 6.40 (t, 2H), 7.15 (t, 2H), 7.50 (d, 2H, J=8 Hz), 7.7 (d, 1H, J=8 Hz), 7.87 (d, 2H, J=8 Hz), 7.98 (dd, 1H), 8.50 (d, 1H, J=2 Hz). MS (m/z): 359 (M−1). Analytics calculated for C$_{77}$H$_{13}$ClN$_2$O$_3$S: C, 56.59; H, 3.63; N, 7.76. Found: C, 56.64; H, 3.85; N, 7.36.

2-Chloro-5-(1H-indole-5-carbonyl)-benzenesulfonamide

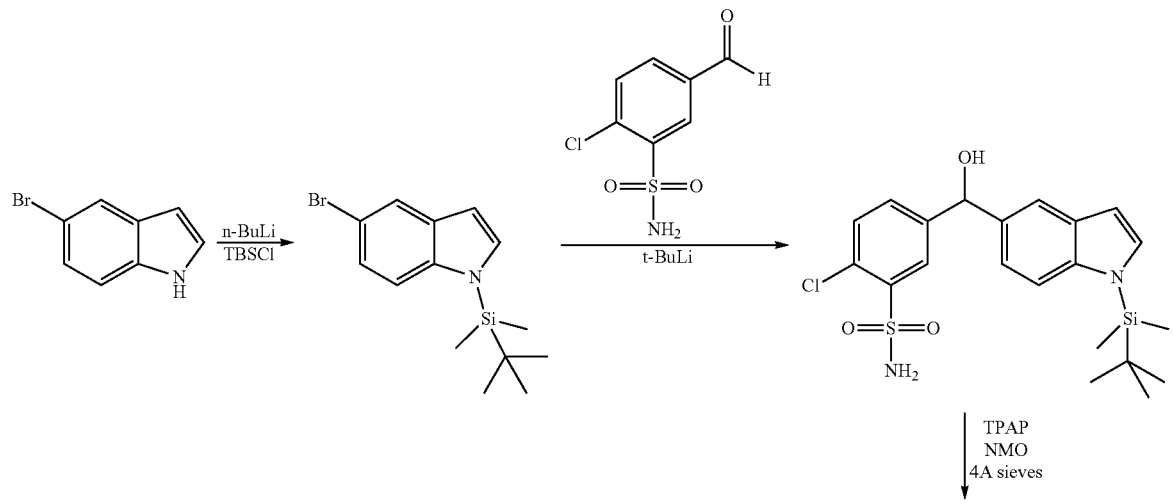

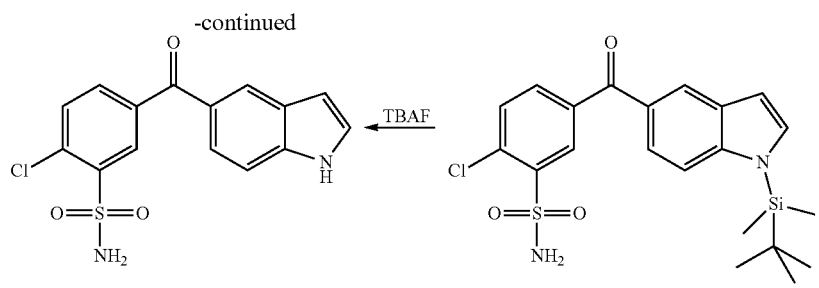

MS (m/z): 335 (M+1). Analytics calculated for $C_{15}H_{11}ClN_2O_3S$: C, 53.82; H, 3.31; N, 8.37. Found: C, 52.39; H, 3.04; N, 7.64. M.P. 65-66° C.

Example 52

The following analogs were prepared by Method C unless otherwise noted.

5-(4-Butyl-benzoyl)-2-chloro-benzenesulfonamide

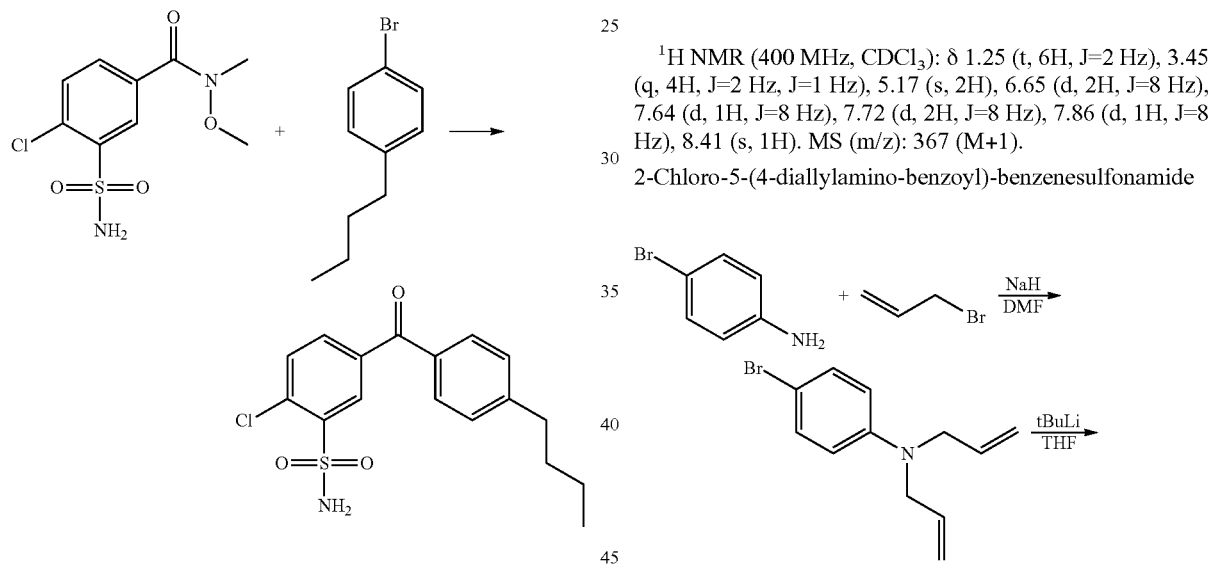

MS (m/z): 350 (M−1). Analytics calculated for $C_{17}H_{18}ClNO_3S$: C, 58.03; H, 5.16; N, 3.98. Found: C, 58.06; H, 4.86; N, 3.73.

2-Chloro-5-(4-diethylamino-benzoyl)-benzenesulfonamide

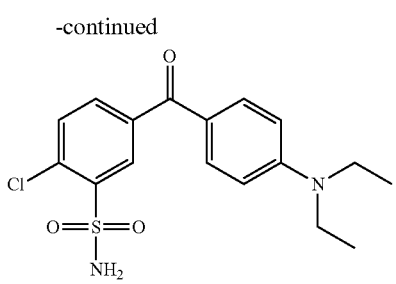

$^1$H NMR (400 MHz, CDCl$_3$): δ 1.25 (t, 6H, J=2 Hz), 3.45 (q, 4H, J=2 Hz, J=1 Hz), 5.17 (s, 2H), 6.65 (d, 2H, J=8 Hz), 7.64 (d, 1H, J=8 Hz), 7.72 (d, 2H, J=8 Hz), 7.86 (d, 1H, J=8 Hz), 8.41 (s, 1H). MS (m/z): 367 (M+1).

2-Chloro-5-(4-diallylamino-benzoyl)-benzenesulfonamide

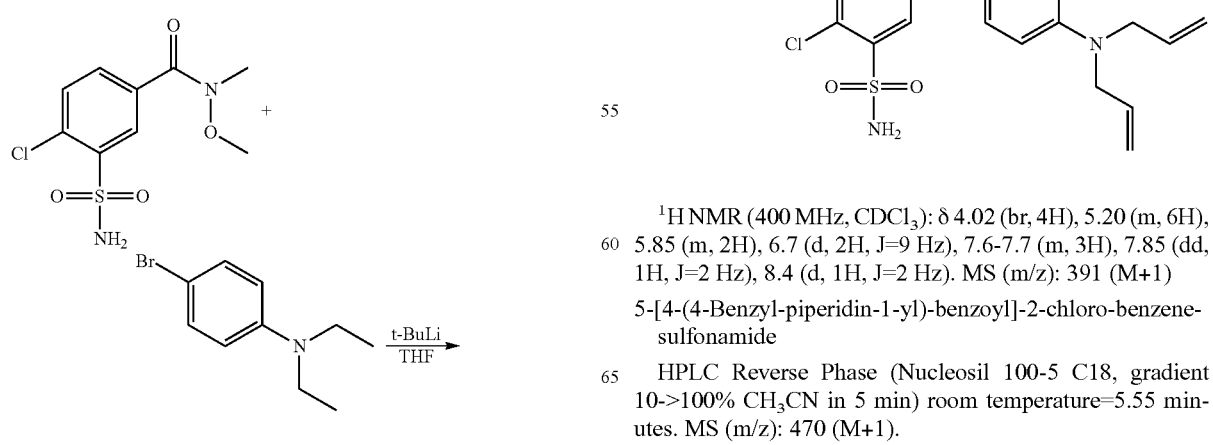

$^1$H NMR (400 MHz, CDCl$_3$): δ 4.02 (br, 4H), 5.20 (m, 6H), 5.85 (m, 2H), 6.7 (d, 2H, J=9 Hz), 7.6-7.7 (m, 3H), 7.85 (dd, 1H, J=2 Hz), 8.4 (d, 1H, J=2 Hz). MS (m/z): 391 (M+1)

5-[4-(4-Benzyl-piperidin-1-yl)-benzoyl]-2-chloro-benzenesulfonamide

HPLC Reverse Phase (Nucleosil 100-5 C18, gradient 10->100% CH$_3$CN in 5 min) room temperature=5.55 minutes. MS (m/z): 470 (M+1).

2-Chloro-5-(4-morpholin-4-yl-benzoyl)-benzenesulfonamide

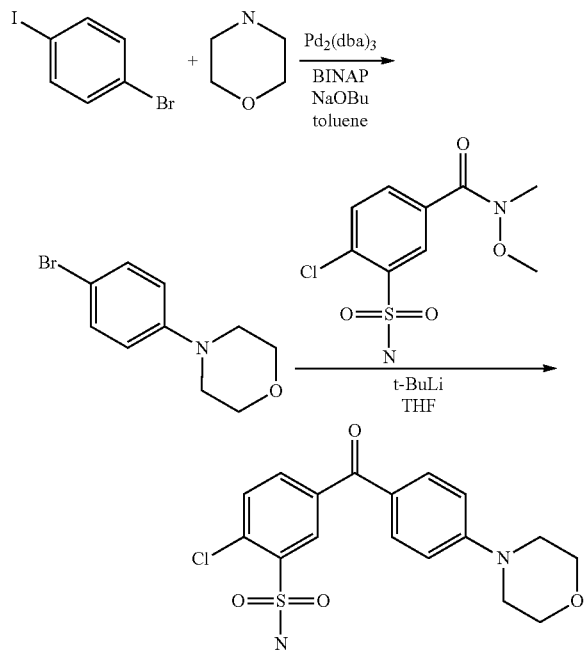

¹H NMR (400 MHz, CDCl₃): δ 3.36 (t, 4H, J=4 Hz), 3.87 (t, 4H, J=4 Hz), 5.18 (s, 2H), 6.90 (d, 2H, J=8 Hz), 7.66 (d, 1H, J=8 Hz), 7.75 (d, 2H, J=8 Hz), 7.90 (d, 1H, J=8 Hz), 8.43 (s, 1H). MS (m/z): 381 (M+1).

2-Chloro-5-[4-(2-oxo-azetidin-1-yl)-benzoyl]-benzenesulfonamide

HPLC Reverse Phase (Nucleosil 100-5 C18, gradient 10->100% CH₃CN in 5 min) room temperature=5.17 minutes. MS (m/z): 365 (M+1).

Preparation of
4-benzyl-1-(4-bromo-phenyl)-piperidine

A mixture of 1-bromo-4-iodo benzene (0.500 g), 4-benzylpiperidine (0.25 mL), sodium-tert-butylate (0.238 g), tris(dibenzylideneacetone)dipalladium (0.016 g) and 2,2'-bis/diphenylphosphino)-1,1'-binaphtyl racemate (0.018 g) is dissolved in tetrahydrofuran and stirred at room temperature overnight. The reaction mixture is concentrated and the resulting residue is loaded on Celite and purified by silica gel chromatography (4:1 hexanes/ethyl acetate) to give 4-benzyl-1-(4-bromo-phenyl)-piperidine as a light yellow syrup. MS (m/z): 331 (M+1).

5-(3H-Benzoimidazole-5-carbonyl)-2-chloro-benzenesulfonamide

The title compound is prepared by analogous methods starting from 6-bromo-1H-benzoimidazole. MS (m/z): (M-1) 334; Rf 0.17 (9:1 methylene chloride/methanol).

2-Chloro-5-(1-methyl-1H-indole-5-carbonyl)-benzenesulfonamide

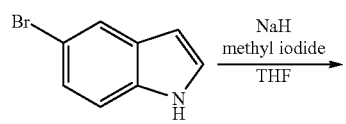

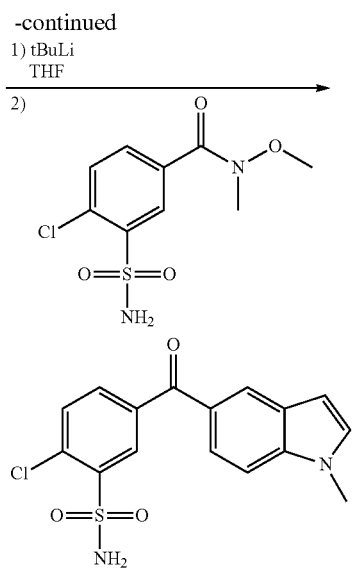

MS (m/z): 347 (M-1). Analytics calculated for C₁₆H₁₃ClN₂O₃S: C, 55.09; H, 3.76; N, 10.16. Found: C, 54.85; H, 3.58; N, 7.65.

2-Chloro-5-[1-(3-methyl-butyl)-1H-indole-5-carbonyl]-benzenesulfonamide

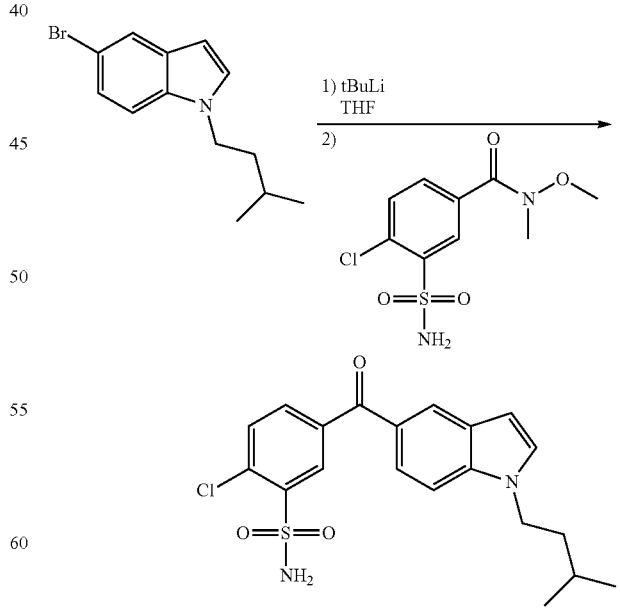

MS (m/z): 403 (M-1). Analytics calculated for C₂₀H₂₁ClN₂O₃S: C, 59.33; H, 5.23; N, 8.76. Found: C, 59.04; H, 5.10; N, 6.91.

Typical procedure for the formation of 4-(4-chloro-3-sul-famoyl-benzoyl)-N-alkyl-benzamides 4-(4-Chloro-3-sulfamoyl-benzoyl)-benzoic acid

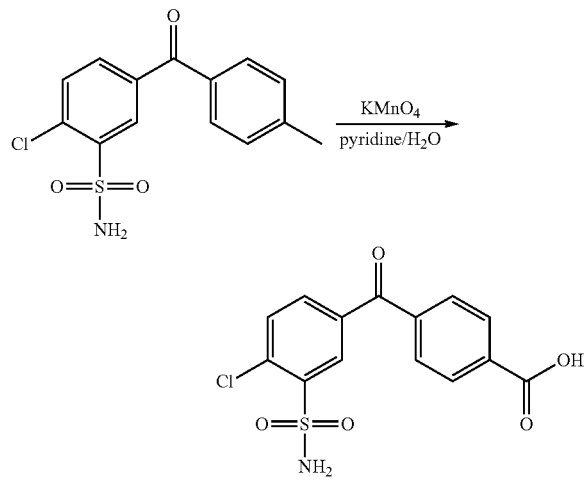

A mixture of 500 mg of 2-chloro-5-(4-methyl-benzoyl)-benzenesulfonamide (1.61 mmol, 1 equivalent) in pyridine/water (80/20 mL) is refluxed as 5 g of potassium permanganate is added in portions. After the additions are completed, the reaction is refluxed for 3 h. The reaction is cooled to room temperature, filtered and the filtrate is concentrated in vacuo. The residue is acidified with 1 N HCl, extracted with ethyl acetate and the combined organic extracts are washed with a saturated sodium chloride solution, dried over sodium sulfate, and concentrated in vacuo to give 450 mg of the title compound as white solid. MS (m/z): 338 (M−1).

Example 53

4-(4-Chloro-3-sulfamoyl-benzoyl)-N-propyl-benzamide

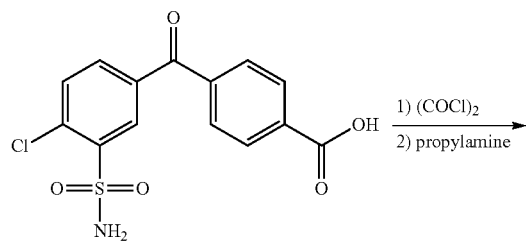

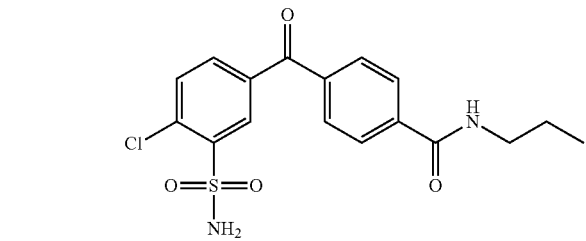

A suspension of 1.2 g of 4-(4-chloro-3-sulfamoyl-benzoyl)-benzoic acid (3.54 mmol, 1 equivalent) in 20 mL of dichloromethane is stirred at room temperature as 898 mg of oxalyl chloride (7.08 mmol, 2 equivalents) is added dropwise followed by the addition of 2 drops of N,N,-dimethylformamide. The reaction mixture is stirred at room temperature for 2 h and then concentrated in vacuo. The resulting acid chloride is used directly in the next step reaction without further purification.

To a stirred solution of 200 mg of acid chloride (0.56 mmol, 1 equivalent) in 10 mL of dichloromethane is added 132 mg of propylamine. The reaction is stirred at room temperature for 18 h. The reaction is acidified with 1 N HCl and extracted with dichloromethane. The combined organic extracts are dried over sodium sulfate and concentrated in vacuo. After purification by flash chromatography, 120 mg of product is obtained as white crystals (yield 56%). $^1$H NMR (400 MHz, CDCl$_3$): δ 1.0 (t, 3H, J=7 Hz), 1.7 (q, 2H, J=7 Hz), 3.4 (t, 2H, J=2 Hz), 7.75-8.43 (m, 7H). MS (m/z): 387 (M+1). Analytics calculated for C$_{17}$H$_{77}$ClN$_2$O$_4$S: C, 53.61; H, 4.50; N, 7.36. Found: C, 53.28; H, 4.42; N, 7.34.

The following compounds were prepared in an analogous manner.

4-(4-Chloro-3-sulfamoyl-benzoyl)-N-phenyl-benzamide

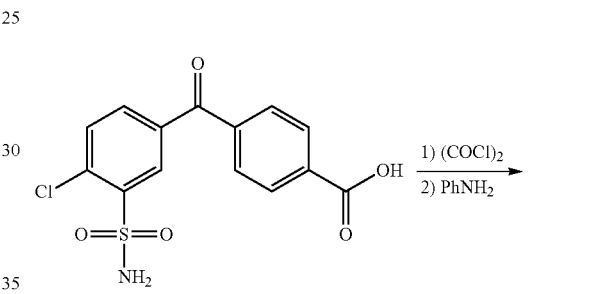

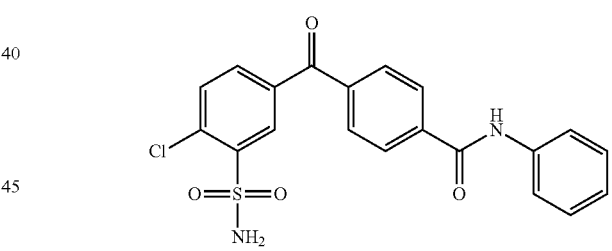

$^1$H NMR (400 MHz, DMSO): δ 7.10 (t, 1H, J=8 Hz), 7.35 (t, 2H, J=8 Hz), 7.75-7.98 (m, 6H), 8.08 (d, 2H, J=8 Hz), 8.31 (d, 1H, J=2 Hz). MS (m/z): 415 (M+1). Analytics calculated for C$_{21}$H$_{17}$ClN$_2$O$_4$S: C, 57.90; H, 3.64; N, 6.75. Found: C, 57.89; H, 3.42; N, 6.63.

N-Benzyl-4-(4-chloro-3-sulfamoyl-benzoyl)-benzamide

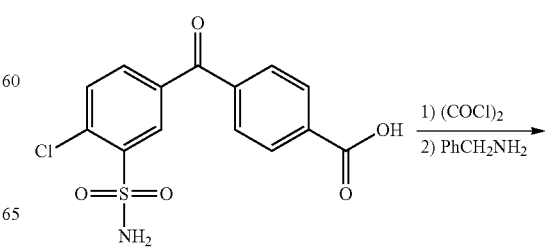

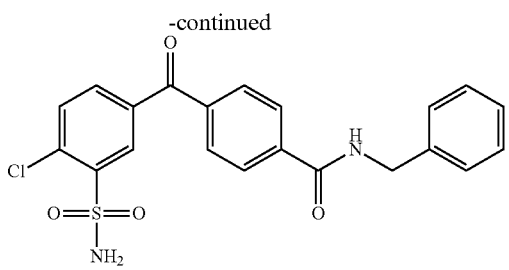

¹H NMR (400 MHz, CDCl₃): δ 4.61 (br, 2H), 7.2-7.4 (m, 5H), 7.75-8.05 (m, 4H), 8.42 (m, 1H). MS (m/z): 427 (M−1). Analytics calculated for $C_{21}H_{17}ClN_2O_4S$: C, 58.81; H, 4.00; N, 6.53. Found: C, 58.53; H, 4.02; N, 6.43.

4-(4-Chloro-3-sulfamoyl-benzoyl)-N-(4-phenyl-butyl)-benzamide

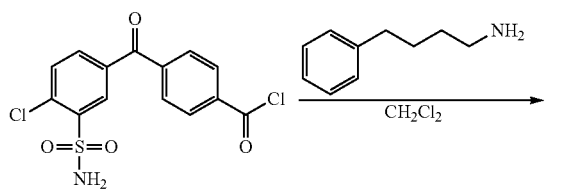

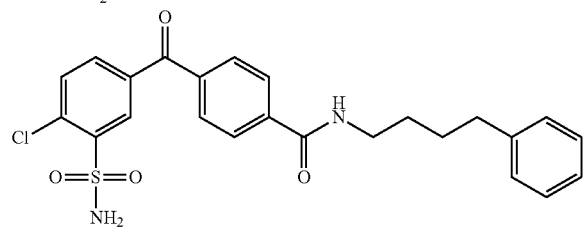

¹H NMR (400 MHz, CDCl₃): δ 1.70 (m, 4H), 2.75 (t, 2H, J=6.5 Hz), 3.55 (t, 2H), 5.27 (s, 2H), 6.22 (s, 1H), 7.15 (m 4H), 7.70-7.89 (m, 7H). MS (m/z): 471 (M+1). Analytics calculated for $C_{24}H_{23}ClN_2O_4S$: C, 61.21; H, 4.92; N, 5.95. Found: C, 61.53; H, 5.28; N, 5.91.

N-tert-Butyl-4-(4-chloro-3-sulfamoyl-benzoyl)-benzamide

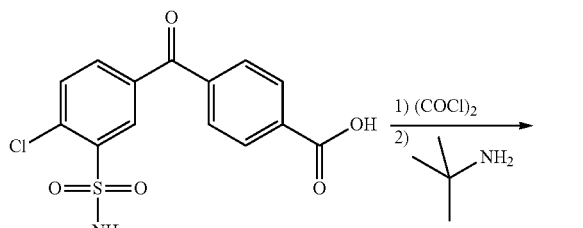

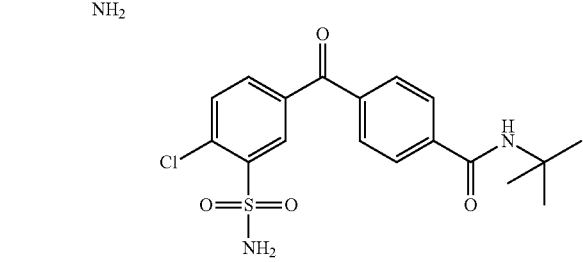

¹H NMR (400 MHz, MeOD): δ 1.48 (s, 9H), 7.75-7.98 (m, 6H), 8.42 (d, 1H, J=2 Hz). MS (m/z): 395 (M+1).

2-Chloro-5-[4-(pyrrolidine-1-carbonyl)-benzoyl]-benzenesulfonamide

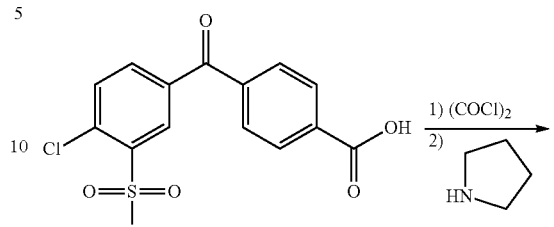

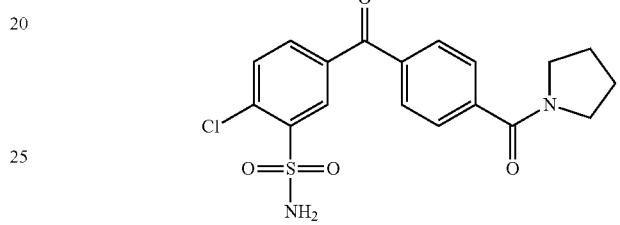

¹H NMR (400 MHz, CDCl₃): δ 1.88-2.05 (m, 4H), 3.40 (t, 2H, J=6.5 Hz), 3.55 (br, 1H), 3.65 (t, 2H, J=6.5 Hz), 5.31 (s, 2H), 7.58-7.99 (m, 6H), 8.48 (d, 1H, J=2 Hz). MS (m/z): 393 (M+1). Analytics calculated for $C_{18}H_{17}ClN_2O_4S$: C, 55.03; H, 4.36; N, 7.13. Found: C, 55.24; H, 4.29; N, 7.45.

4-(4-Chloro-3-sulfamoyl-benzoyl)-N-phenethyl-benzamide

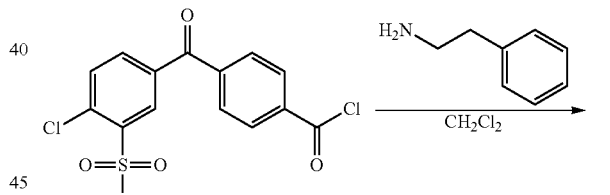

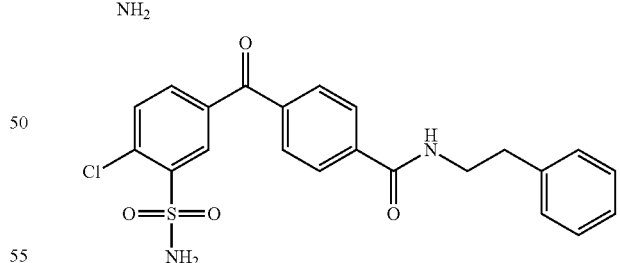

¹H NMR (400 MHz, CDCl₃): δ 3.00 (t, 2H), 3.83 (t, 2H), 5.22 (s, 2H), 6.27 (br, 1H), 7.2-7.35 (m, 5H), 7.72-8.0 (m, 6H), 8.45 (s, 1H). MS (m/z): 443 (M+1). Analytics calculated for $C_{22}H_{19}ClN_2O_4S$: C, 59.66; H, 4.32; N, 6.32. Found: C, 60.00; H, 4.71; N, 6.13.

Typical procedure for Suzuki couplings of 5-(4-bromo-benzoyl)-2-chloro-benzenesulfonamide 2-Chloro-5-(3'-nitro-biphenyl-4-carbonyl)-benzenesulfonamide

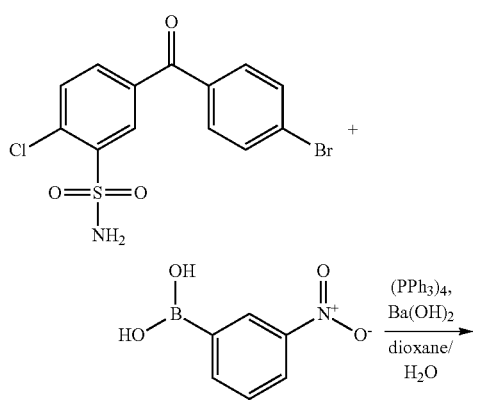

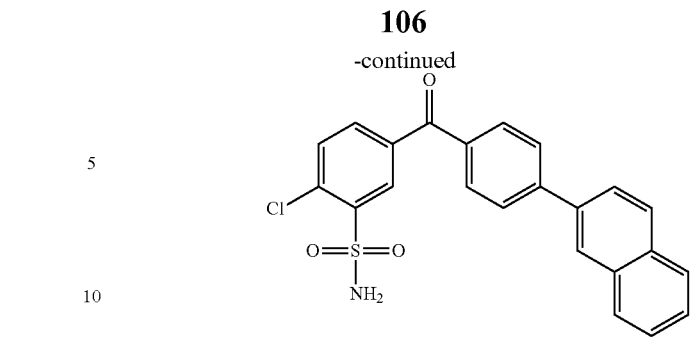

MS (m/z): 420 (M−1). Analytics calculated for $C_{23}H_{16}ClNO_3S$: C, 65.48; H, 3.82; N, 3.32. Found: C, 65.19; H, 3.97; N, 3.19. M.P. 193-195° C.

2-Chloro-5-(4-thiophen-2-yl-benzoyl)-benzenesulfonamide

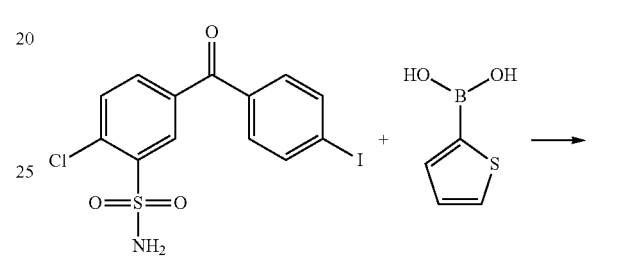

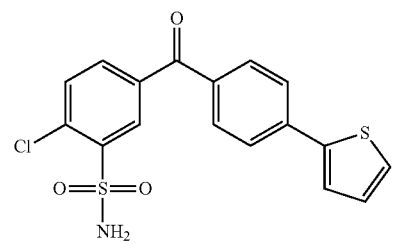

A mixture of 220 mg of 5-(4-bromo-benzoyl)-2-chloro-benzenesulfonamide (0.587 mmol, 1 equivalent), 196 mg of 3-nitrobenzene boronic acid (1.174 mmol, 2 equivalent), 556 mg of $Ba(OH)_2$ (1.761 mmol, 3 equivalent), and 14 mg of $Pd(PPh_3)_4$ in degassed dioxane/water (30 mL/10 mL) is refluxed for 18 h. The reaction is quenched with 1 N HCl and extracted with ethyl acetate. The combined organic extracts are dried over sodium sulfate, and concentrated in vacuo. After purification by flash chromatography, 50 mg of the title compound is obtained as white solid. $^1$H NMR (400 MHz, $CDCl_3$): δ 5.2 (br, 2H), 6.18 (br, 1H), 7.02 (d, 2H, J=8 Hz), 7.12-7.45 (m, 5H), 7.6-7.8 (m, 3H), 7.90 (dd, 1H), 8.41 (s, 1H). MS (m/z): 387 (M+1).

The following compounds were made by analogous procedures

2-Chloro-5-(4-naphthalen-2-yl-benzoyl)-benzenesulfonamide

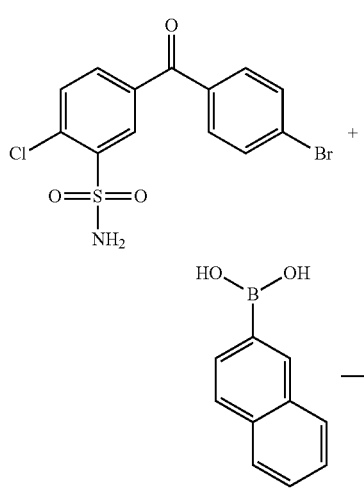

MS (m/z): 376 (M−1). M.P. 146-148° C.
2-Chloro-5-(4-thiophen-3-yl-benzoyl)-benzenesulfonamide

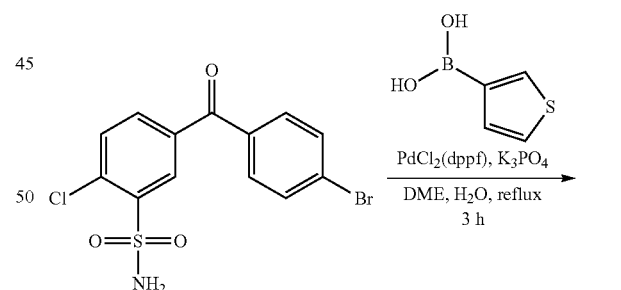

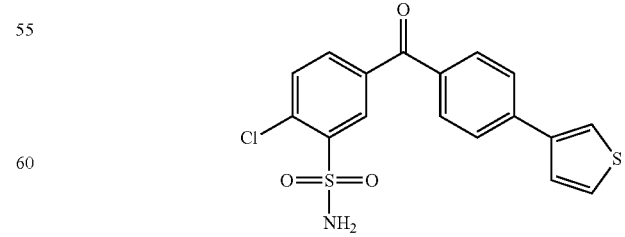

MS (m/z): 376 (M−1)⁻. Analytics calculated for $C_{17}H_{12}ClNO_3S_2$: C, 54.04; H, 3.2; N, 3.71. Found: C, 54.12; H, 3.09; N, 3.52.

2-Chloro-5-(4-pyridin-3-yl-benzoyl)-benzenesulfonamide

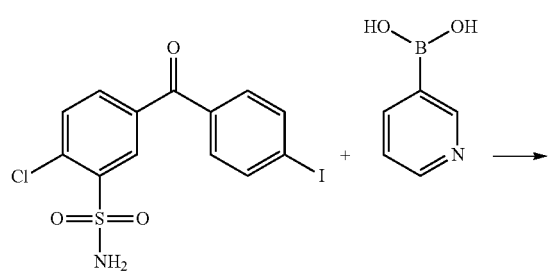

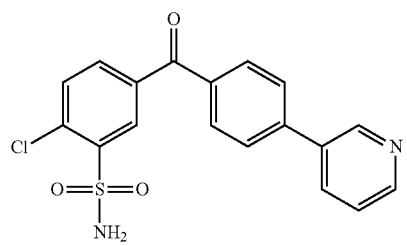

MS (m/z): 371 (M−1). Analytics calculated for $C_{18}H_{13}ClN_2O_3S$: C, 57.99; H, 3.51; N, 7.51. Found: C, 58.41; H, 3.49; N, 7.07. M.P. 190-192° C.

2-Chloro-5-(4-pyridin-4-yl-benzoyl)-benzenesulfonamide

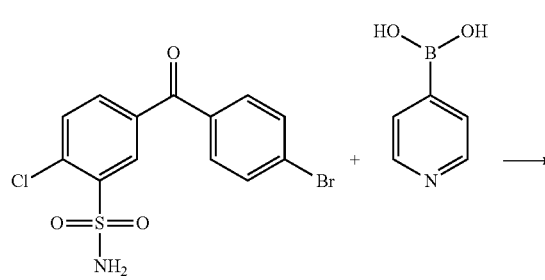

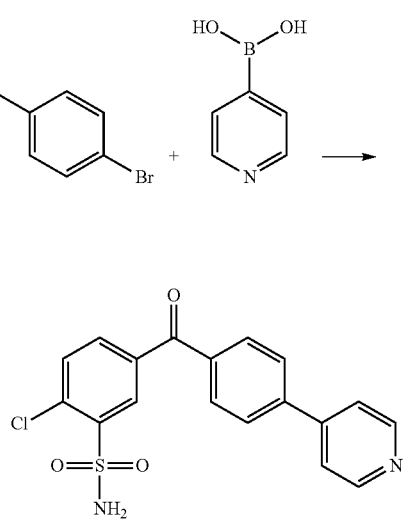

MS (m/z): 371 (M−1).

2-Chloro-5-[4-(2-chloro-pyridin-4-yl)-benzoyl]-benzenesulfonamide

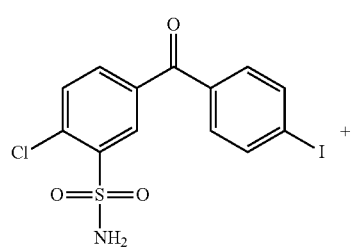

-continued

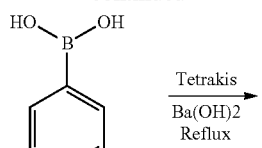

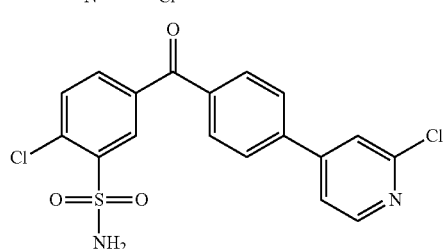

MS (m/z): 406 (M−1). Analytics calculated for $C_{18}H_{12}Cl_2N_2O_3S$: C, 53.08; H, 2.97; N, 6.88. Found: C, 52.72; H, 3.10; N, 6.97. M.P. 218-220° C.

2-Chloro-5-(3'-methyl-biphenyl-4-carbonyl)-benzenesulfonamide

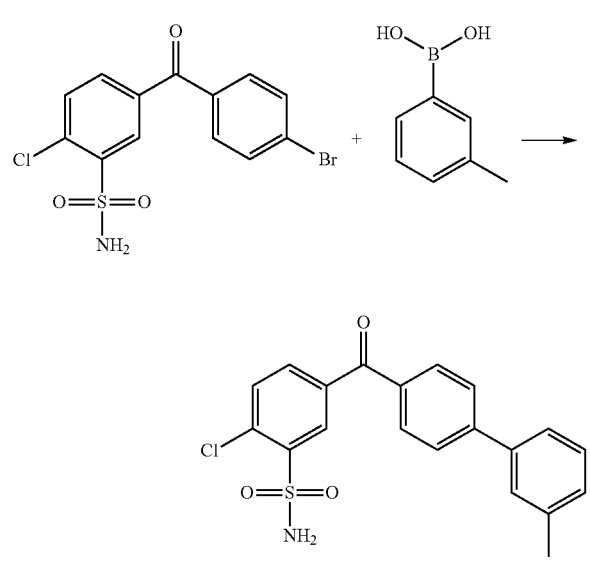

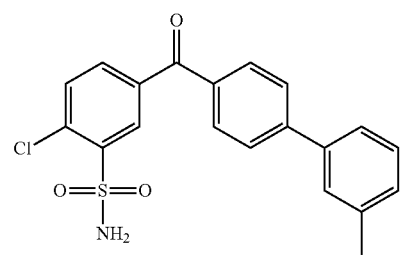

MS (m/z): 384 (M−1). Analytics calculated for $C_{20}H_{16}ClNO_3S$: C, 62.25; H, 4.18; N, 3.63. Found: C, 62.28; H, 3.98; N, 3.45. M.P. 176-178° C.

2-Chloro-5-(4'-trifluoromethyl-biphenyl-4-carbonyl)-benzenesulfonamide

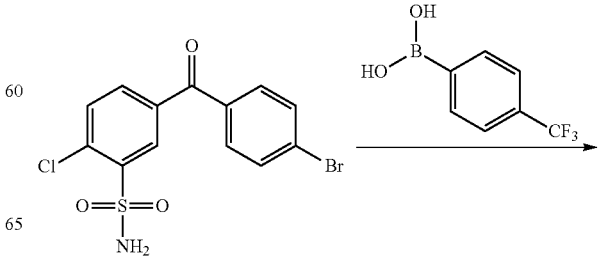

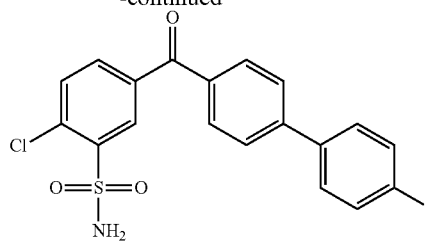

MS (m/z): 438 (M−1). Analytics calculated for $C_{20}H_{13}ClF_3NO_3S$: C, 54.62; H, 2.98; N, 3.18. Found: C, 54.63; H, 2.56; N, 3.00. M.P. 117-119° C.

2-Chloro-5-(4'-ethyl-biphenyl-4-carbonyl)-benzenesulfonamide

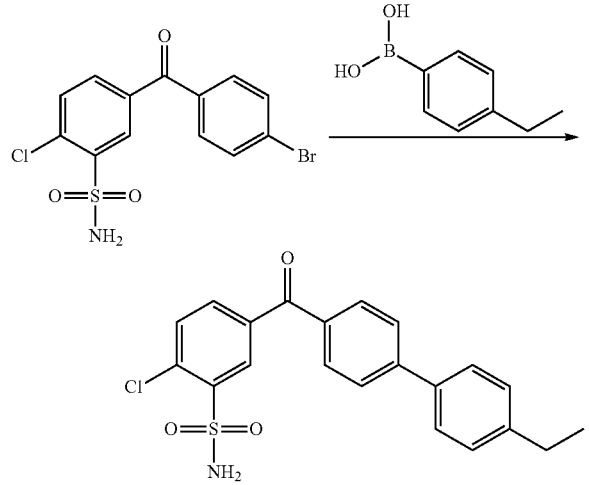

MS (m/z): 398 (M−1). Analytics calculated for $C_{21}H_{18}ClNO_3S$: C, 63.07; H, 4.54; N, 3.5. Found: C, 63.14; H, 4.35; N, 3.42.

5-(3'-Amino-biphenyl-4-carbonyl)-2-chloro-benzenesulfonamide

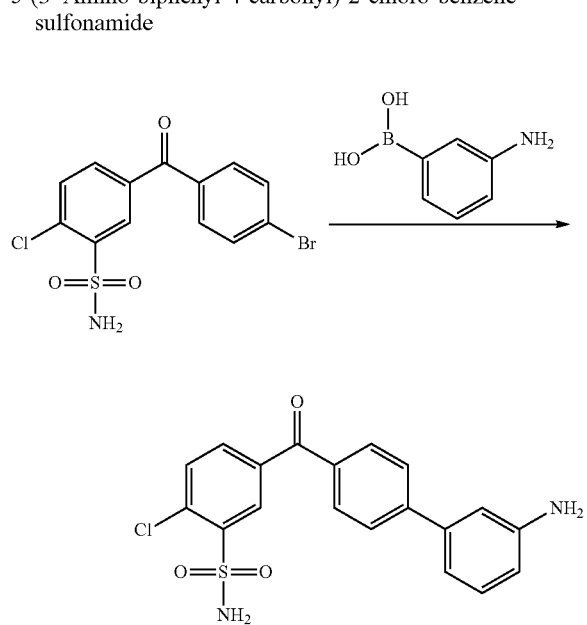

MS (m/z): 385 (M−1). Analytics calculated for $C_{19}H_{15}ClN2O_3S$: C, 58.99; H, 3.91; N, 7.24. Found: C, 59.30; H, 3.78; N, 7.33. M.P. 228-230° C.

N-[4'-(4-Chloro-3-sulfamoyl-benzoyl)-biphenyl-3-yl]-acetamide

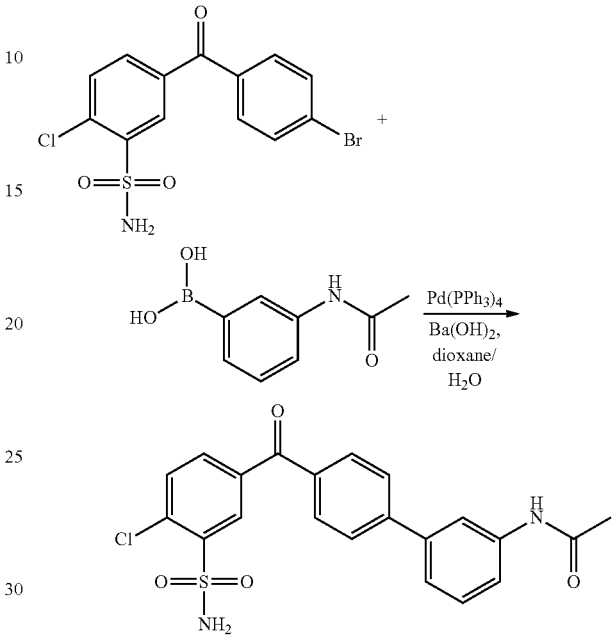

$^1$H NMR (400 MHz, CDCl$_3$): δ 2.23 (s, 3H), 5.2 (s, 2H), 7.38-8.0 (m, 10H), 8.5 (s, 1H). MS (m/z): 429 (M+1). Analytics calculated for $C_{21}H_{17}ClN_2O_4S$: C, 58.81; H, 4.00; N, 6.53. Found: C, 58.99; H, 3.90; N, 6.19.

2-Chloro-5-(3'-hydroxymethyl-biphenyl-4-carbonyl)-benzenesulfonic acid

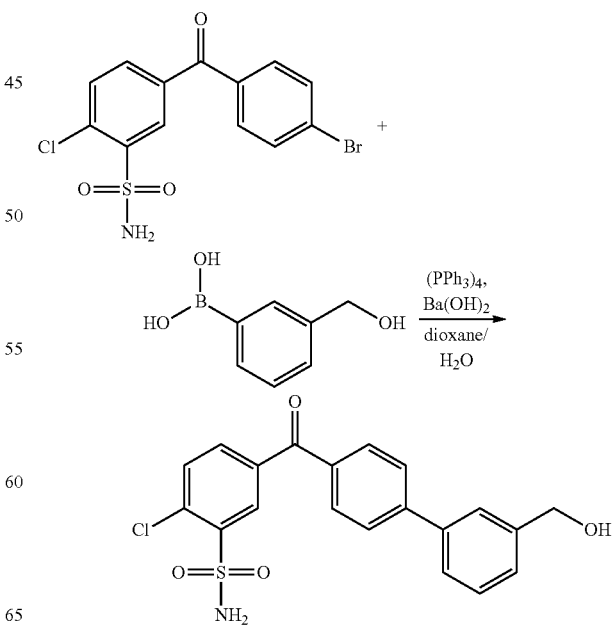

¹H NMR (400 MHz, CDCl₃): δ 4.81 (s, 2H), 5.17 (s, 2H), 7.40-7.90 (m, 9H), 8.01 (d, 1H, J=8 Hz), 8.53 (s, 1H). MS (m/z): 400 (M−1).

2-Chloro-5-(4'-formyl-biphenyl-4-carbonyl)-benzene-sulfonamide

MS (m/z): 414 (M−1). Analytics calculated for $C_{20}H_{14}ClNO_5S$: C, 57.76; H, 3.39; N, 3.37. Found: C, 57.45; H, 3.05; N, 3.25.

4'-(4-Chloro-3-sulfamoyl-benzoyl)-biphenyl-4-carboxylic acid methyl ester

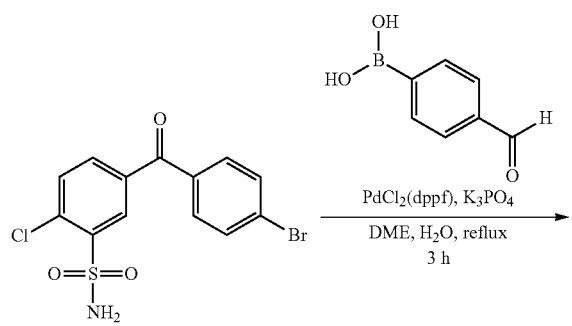

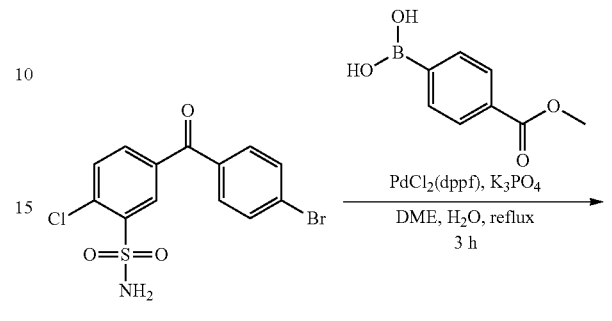

MS (m/z): 398 (M−1).

4'-(4-Chloro-3-sulfamoyl-benzoyl)-biphenyl-4-carboxylic acid

MS (m/z): 428 (M−1). Analytics calculated for $C_{21}H_{16}ClNO_5S_2$: C, 58.67; H, 3.75; N, 3.26. Found: C, 58.29; H, 3.72; N, 3.20.

5-(3'-Benzyloxy-biphenyl-4-carbonyl)-2-chloro-benzene-sulfonamide

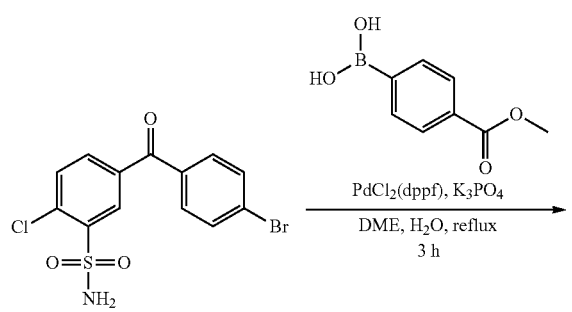

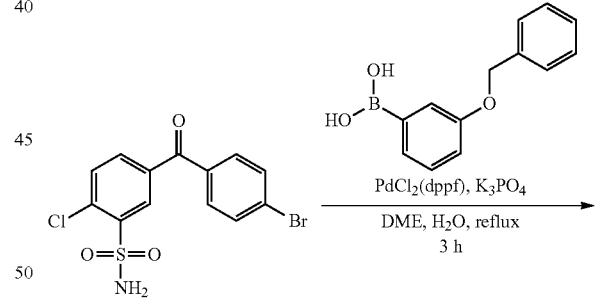

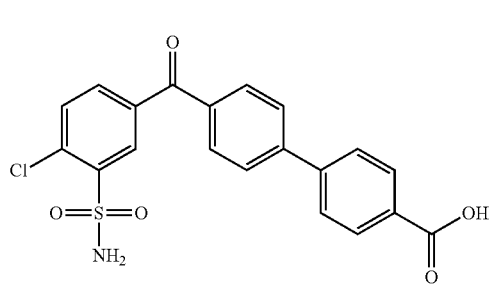

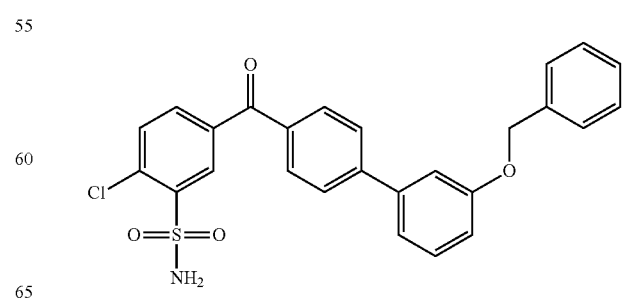

MS (m/z): 476 (M−1).

2-Chloro-5-(2'-methyl-biphenyl-4-carbonyl)-benzene-sulfonamide

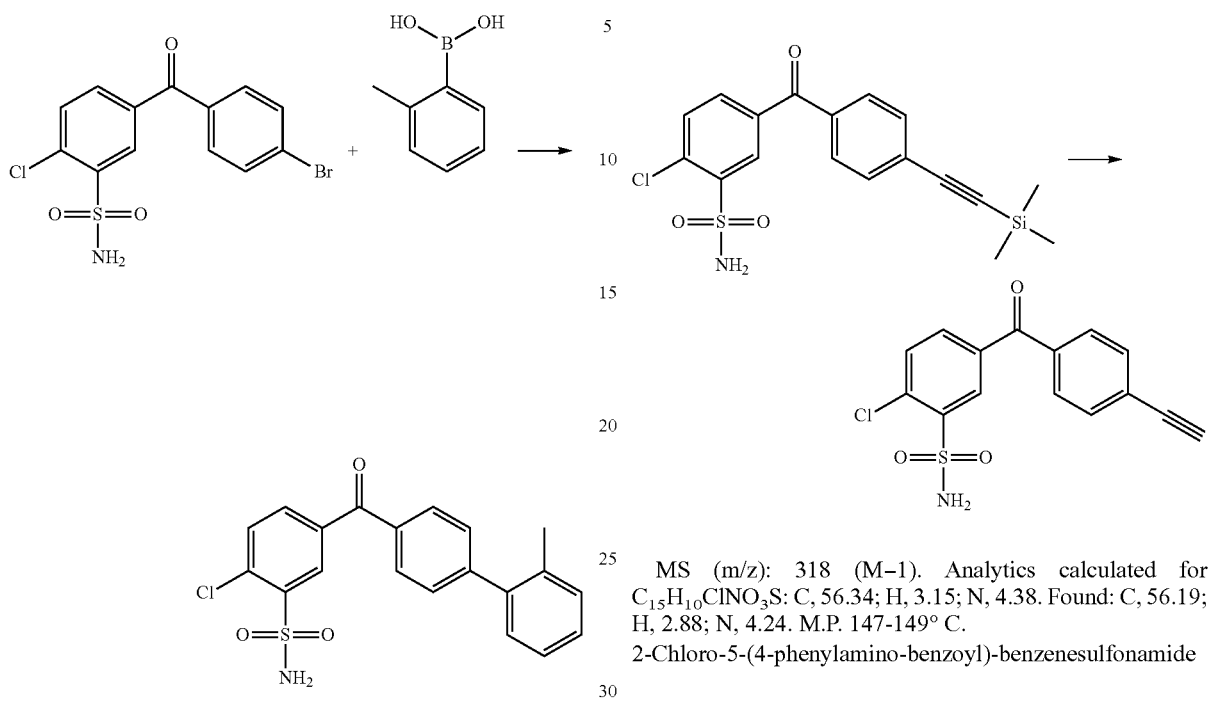

MS (m/z): 384 (M−1). Analytics calculated for $C_{20}H_{16}ClNO_3S$: C, 62.25; H, 4.18; N, 3.63. Found: C, 62.64; H, 4.18; N, 3.63. M.P. 98-100° C.

2-Chloro-5-(3-trifluoromethyl-biphenyl-4-carbonyl)-benzenesulfonamide

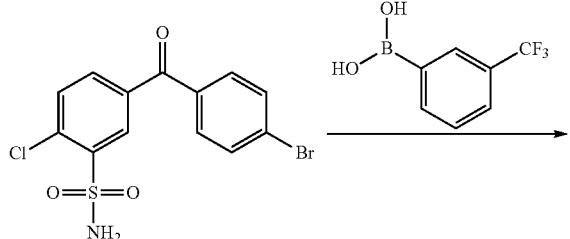

MS (m/z): 438 (M−1). Analytics calculated for $C_{20}H_{13}ClF_3NO_3S$: C, 54.62; H, 2.98; N, 3.18. Found: C, 55.27; H, 2.97; N, 2.84. M.P. 75-77° C.

The following two examples were also synthesized via palladium mediated cross coupling.

2-Chloro-5-(4-ethynyl-benzoyl)-benzenesulfonamide

MS (m/z): 318 (M−1). Analytics calculated for $C_{15}H_{10}ClNO_3S$: C, 56.34; H, 3.15; N, 4.38. Found: C, 56.19; H, 2.88; N, 4.24. M.P. 147-149° C.

2-Chloro-5-(4-phenylamino-benzoyl)-benzenesulfonamide $^1$H NMR (400 MHz, CDCl$_3$): δ 5.2 (br, 2H), 6.18 (br, 1H), 7.02 (d, 2H, J=8 Hz), 7.12-7.45 (m, 5H), 7.6-7.8 (m, 3H), 7.90 (dd, 1H), 8.41 (s, 1H). MS (m/z): 387 (M+1).

Example 54

General Synthesis of Indazole Analogs

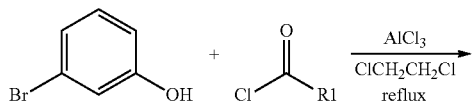

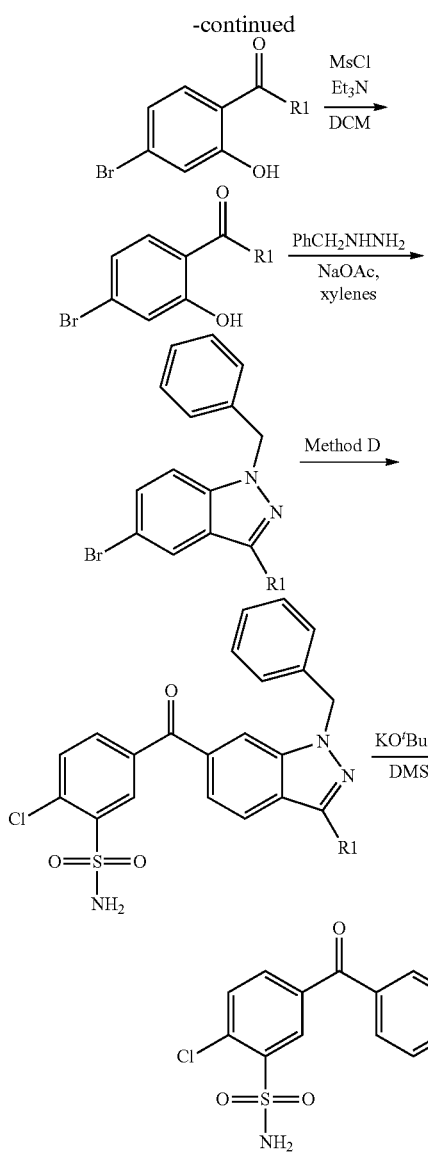

A Typical Procedure for Acylation-Fries Rearrangement

To a solution of 3-bromophenol (1.0 equivalent) in methylene chloride (5 vol) is added aluminum chloride (1.5 equivalent) followed by acid chloride (1.0 equivalent). The mixture is heated to reflux for 2-3 h, cooled to room temperature, and the mixture is poured slowly into a beaker containing ice and 2 N HCl and extracted with methylene chloride. The combined organic extracts are dried over sodium sulfate, filtered, and concentrated to a crude solid, which is purified by flash chromatography.

General Procedure for Mesylate Formation

To a solution of phenol (1.0 equivalent) in dichloromethane (5 vol) is added triethylamine (2.0 equivalent). The resulting solution is cooled to 0° C. and methylsulfonyl chloride (1.1 equivalent) is added drop-wise. The reaction is stirred at room temperature for (30 minutes to 18 h), poured into 1 N HCl and extracted with dichloromethane. The combined organic extracts are dried over sodium sulfate, filtered, and concentrated to give the crude product, which is purified by flash chromatography.

General Procedure for Indazole Formation

The mesylate (1.0 equivalent) is combined with the HCl salt of the benzyl hydrazine (1.5 equivalent) and sodium acetate (3.0 equivalent) in xylenes (6 vol). The mixture is heated to reflux in a Dean-Stark apparatus until completion. The reaction is cooled to room temperature, poured into 1 N HCl and extracted with toluene. The combined organic extracts are dried over sodium sulfate and concentrated to afford the crude indazole which is purified by flash chromatography.

General Procedure for N-Debenzylation

Benzyl-indazole is dissolved in dimethylsulfoxide and potassium tert-butoxide (1 M solution in tetrahydrofuran) is added at room temperature. Oxygen is then bubbled into the solution for 5 minutes. The reaction is allowed to stir at room temperature for 18 h. The reaction is quenched with aqueous saturated ammonium chloride then extracted three times with ethyl acetate. The combined organic extracts are dried over sodium sulfate, and concentrated. Purification by flash chromatography provides the deprotected indazole.

Example 55

2-Chloro-5-(3-ethyl-1H-indazole-6-carbonyl)-benzenesulfonamide

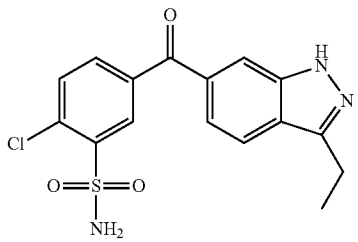

$^1$H NMR (400 MHz, CDCl$_3$): δ 1.45 (t, 3H, J=8 Hz), 3.06 (q, 2H, J=8 Hz), 5.24 (2H), 7.57 (d, 1H, J=0.16 Hz), 7.71 (d, 1H, J=0.16 Hz), 7.86-7.82 (m, 4H), 8.52 (s, 1H). MS (m/z): 364 (M+1).

Example 56

2-Chloro-5-(3-methyl-1H-indazole-6-carbonyl)-benzenesulfonamide

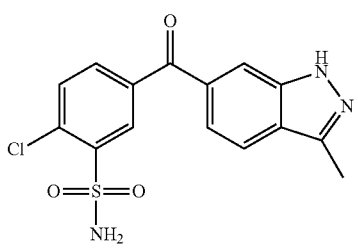 [SMILES: Cc1n[nH]c2cc(C(=O)c3ccc(Cl)c(S(N)(=O)=O)c3)ccc12]

¹H NMR (400 MHz, MeOD). δ 2.61 (s, 3H), 7.54 (m, 1H), 7.78 (1H), 7.88 (1H), 7.98 (1H), 8.48 (1s, 1H). MS (m/z): 350 (M+1).

Example 57

2-Chloro-5-(3-isopropyl-1H-indazole-6-carbonyl)-benzenesulfonamide

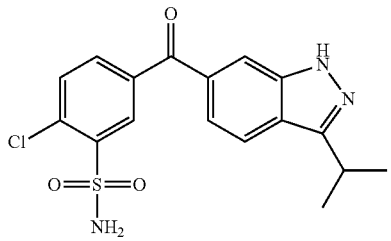 [SMILES: CC(C)c1n[nH]c2cc(C(=O)c3ccc(Cl)c(S(N)(=O)=O)c3)ccc12]

¹H NMR (400 MHz, CDCl₃): δ1.48 (d, 6H, J=8 Hz), 3.47 (m, 1H), 5.24 (m, 2H), 7.55 (d, 1H, J=4 Hz), 7.71 (d, 1H, J=4 Hz), 7.86-7.89 (m, 2H), 8.01 (d, 1H, J=4 Hz), 8.52 (s, 1H). MS (m/z): 378 (M+1).

Example 58

5-(1-Benzyl-3-ethyl-1H-indazole-6-carbonyl)-2-chloro-benzenesulfonamide

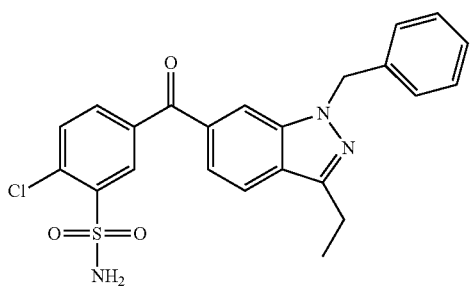 [SMILES: CCc1nn(Cc2ccccc2)c2cc(C(=O)c3ccc(Cl)c(S(N)(=O)=O)c3)ccc12]

¹H NMR (400 MHz, CDCl₃): δ 1.35 (t, 3H, J=7.7 Hz), 3.06 (q, 2H, J=7.7 Hz), 5.15 (m, 2H), 5.58 (2H), 7.19 (d, 2H, J=8 Hz), 7.28-7.86 (m, 8H), 8.48 (d, 1H, J=4 Hz). MS (m/z): 454.1 (M+1).

Example 59

2-Chloro-5-[3-(2-cyclopentyl-ethyl)-1H-indazole-6-carbonyl]-benzenesulfonamide

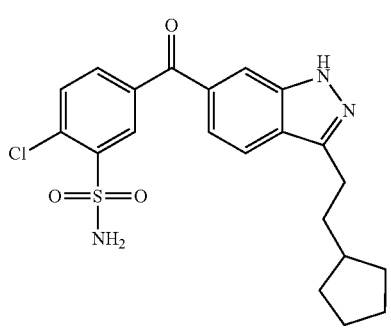 [SMILES: NS(=O)(=O)c1cc(C(=O)c2ccc3c(CCC4CCCC4)n[nH]c3c2)ccc1Cl]

¹H NMR (400 MHz, CDCl₃): δ 1.25 (m, 2H), 1.5-1.7 (m, 6H), 1.85 (m, 5H), 3.03 (t, 2H), 5.34 (s, 2H), 7.56 (d, 1H, J=4 Hz), 7.70 (d, 1H), 7.83 (m, 2H), 8.0 (1H), 8.5 (s, 1H). MS (m/z): 432 (M+1).

Table 1 below shows the inhibitory activity (IC₅₀ values) of representative compounds to MMP02 and MMP13.

TABLE 1

| Example # | IUPAC Name | MMP02 IC$_{50}$ (µM) | MMP13 IC$_{50}$ (µM) | MW (Calc'd) | MW (Found) |
|---|---|---|---|---|---|
| 1 | 3-(4-Methoxy-benzoyl)-benzenesulfonamide | 1.92 | 2.49 | 291.33 | 290 (M − 1) |
| 2 | 2-Fluoro-5-(4-methoxy-benzoyl)-benzenesulfonamide | 2.41 | 1.59 | 309.32 | 308 (M − 1) |
| 3 | 2-Chloro-5-(4-methoxy-benzoyl)-benzenesulfonamide | 5.18 | 2.02 | 325.77 | 326 (M + 1) |
| 4 | 2,3-Difluoro-5-(4-methoxy-benzoyl)-benzenesulfonamide | 4.68 | 5.73 | 327.31 | 326 (M − 1) |
| 5 | 5-(4-Methoxy-benzoyl)-2-nitro-benzenesulfonamide | 1.06 | 1.39 | 336.33 | 335 (M − 1) |
| 6 | 5-(4-Methoxy-benzoyl)-2-methyl-benzenesulfonamide | 2.78 | 4.51 | 305.36 | 306 (M + 1) |
| 7 | 5-(4-Methoxy-benzoyl)-2-methylsulfanyl-benzenesulfonamide | 2.36 | 3.72 | 337.42 | 336 (M − 1) |
| 8 | 2-Methanesulfinyl-5-(4-methoxy-benzoyl)-benzenesulfonamide | 4.48 | 10.74 | 353.42 | 352 (M − 1) |
| 9 | 2-Methanesulfonyl-5-(4-methoxy-benzoyl)-benzenesulfonamide | 2.93 | 11.35 | 369.42 | 368 (M − 1) |
| 10 | 3-[3-(2-Methyl-pyridin-4-yl)-1H-indole-6-carbonyl]-benzenesulfonamide | 3.4 | 0.03 | 391.45 | 390 (M − 1) |
| 11 | 3-{3-[2-(3-Methoxy-propyl)-pyridin-4-yl]-1H-indole-6-carbonyl}-benzenesulfonamide | 3.95 | 0.075 | 449.53 | 450 (M + 1) |
| 12 | 2-Chloro-5-(4-methoxy-benzoyl)-N-phenethyl-benzenesulfonamide | 9.13 | 3.04 | 429.93 | 430.0 (M + 1) |
| 13 | 2-Chloro-N-[2-(4-fluoro-phenyl)-ethyl]-5-(4-methoxy-benzoyl)-benzenesulfonamide | 8.8 | 6.9 | 447.92 | 448.0 (M + 1) |
| 14 | 3-{3-[2-(3-Morpholin-4-yl-propyl)-pyridin-4-yl]-1H-indole-6-carbonyl}-benzenesulfonamide | 0.8 | 0.01 | 504.61 | 505 (M + 1) |
| 15 | 2-Chloro-5-(4-hydroxy-benzoyl)-benzenesulfonamide | 5.16 | 10 | 311.75 | 310 (M − 1) |
| 16 | 2-Chloro-5-[4-(2-hydroxy-ethoxy)-benzoyl]-benzenesulfonamide | 5.94 | 4.9 | 341.77 | 342 (M + 1) |
| 17 | 2-Chloro-5-[4-(2-hydroxy-ethoxy)-benzoyl]-benzenesulfonamide | 2.30 | 3.71 | 355.8 | 354 (M − 1) |
| 19 | 2-Chloro-5-(4-isobutoxy-benzoyl)-benzenesulfonamide | 1.58 | 1.22 | 367.85 | 366 (M − 1) |
| 20 | 2-Chloro-5-(4'-allyloxy-benzoyl)-benzenesulfonamide | 11 | 13.6 | 351.81 | 350 (M − 1) |

TABLE 1-continued

| Example # | IUPAC Name | MMP02 IC$_{50}$ (μM) | MMP13 IC$_{50}$ (μM) | MW (Calc'd) | MW (Found) |
|---|---|---|---|---|---|
| 21 | 2-Chloro-5-[4-(3-methyl-butoxy)-benzoyl]-benzenesulfonamide | 4.73 | 0.86 | 381.88 | 380 (M − 1) |
| 22 | 2-Chloro-5-[4-(3-phenyl-propoxy)-benzoyl]-benzenesulfonamide | 14 | 2.05 | 429.93 | 430 (M + 1) |
| 23 | 2-Chloro-5-(4-pentyloxy-benzoyl)-benzenesulfonamide | 4.15 | 0.95 | 381.88 | 382 (M + 1) |
| 24 | 2-Chloro-5-(4-hexyloxy-benzoyl)-benzenesulfonamide | 9.16 | 2.1 | 395.91 | 396 (M + 1) |
| 26 | 2-Chloro-5-(3-methyl-benzoyl)-benzenesulfonamide | 17.2 | 10.53 | 309.77 | 308 (M − 1) |
| 27 | 2-Chloro-5-(4-trifluoromethoxy-benzoyl)-benzenesulfonamide | 7.46 | 9.64 | 379.74 | 378 (M − 1) |
| 30 | 2-Chloro-5-(4-cyclopropyl-benzoyl)-benzenesulfonamide | 1.23 | 1.69 | 335.81 | 334 (M − 1) |
| 31 | 2-Chloro-5-(4-cyclopentyl-benzoyl)-benzenesulfonamide | 10.44 | 12.41 | 363.87 | 370 (M − 1) |
| 32 | 2-Chloro-5-(4-cyclohexyl-benzoyl)-benzenesulfonamide | 8.3 | 10.02 | 377.89 | 376 (M − 1) |
| 33 | 2-Chloro-5-(4-trimethylsilanylethynyl-benzoyl)-benzenesulfonamide | >30 | 2.59 | 391.95 | 390 (M − 1) |
| 34 | 2-Chloro-5-(4-ethynyl-benzoyl)-benzenesulfonamide | 2.51 | 4.71 | 319.77 | 318 (M − 1) |
| 35 | 2-Chloro-5-(4-phenylethynyl-benzoyl)-benzenesulfonamide | 6.89 | 0.84 | 395.87 | 394 (M − 1) |
| 37 | 4-(4-Chloro-3-sulfamoyl-benzoyl)-N-phenyl-benzamide | 22.8 | 8.9 | 414.87 | 415 (M + 1) |
| 38 | N-Benzyl-4-(4-chloro-3-sulfamoyl-benzoyl)-benzamide | 14.54 | 8.58 | 428.9 | 427 (M − 1) |
| 40 | 4-(4-Chloro-3-sulfamoyl-benzoyl)-N-(4-phenyl-butyl)-benzamide | >30 | 7.06 | 470.98 | 471 (M + 1) |
| 41 | 2-Chloro-5-(4-naphthalen-2-yl-benzoyl)-benzenesulfonamide | >9 | 7.52 | 421.91 | 420 (M − 1) |
| 42 | 2-Chloro-5-(4-thiophen-2-yl-benzoyl)-benzenesulfonamide | 0.51 | 1.5 | 377.87 | 376 (M − 1) |
| 43 | 2-Chloro-5-(4-thiophen-3-yl-benzoyl)-benzenesulfonamide | 0.30 | 0.38 | 377.87 | 376 (M − 1) |
| 44 | 2-Chloro-5-(4-pyridin-3-yl-benzoyl)-benzenesulfonamide | 0.62 | 0.56 | 372.83 | 371 (M − 1) |
| 45 | 2-Chloro-5-(4-pyridin-4-yl-benzoyl)-benzenesulfonamide | 0.053 | 0.08 | 372.83 | 371 (M − 1) |
| 46 | 2-Chloro-5-[4-(2-chloro-pyridin-4-yl)-benzoyl]-benzenesulfonamide | 0.15 | 0.21 | 407.28 | 406 (M − 1) |
| 47 | 2-Chloro-5-(4-cyano-benzoyl)-benzenesulfonamide | 17.3 | 11.1 | 320.76 | 319 (M − 1) |
| 48 | 5-(2-Bromo-4-methyl-benzoyl)-2-chloro-benzenesulfonamide | >30 | 25.3 | 388.67 | 386 (M − 1) |
| 49 | 5-(4-Bromo-2-methyl-benzoyl)-2-chloro-benzenesulfonamide | >30 | 24.8 | 388.67 | 386 (M − 1) |
| 50 | 2-Chloro-5-(2-fluoro-4-methoxy-benzoyl)-benzenesulfonamide | 24.3 | 21.3 | 343.76 | 342 (M − 1) |
| 51 | 2-Chloro-5-(3-fluoro-4-hydroxy-benzoyl)-benzenesulfonamide | 14.6 | 18.7 | 329.74 | 330 (M + 1) |
| 52 | 2-Chloro-5-(2,4-dimethoxy-benzoyl)-benzenesulfonamide | 29.1 | 21.3 | 355.8 | 356 (M + 1) |
| 53 | 5-Benzoyl-2-chloro-benzenesulfonamide | >30 | >30 | 295.75 | 294 (M − 1) |
| 54 | 2-Chloro-5-(3-fluoro-4-hydroxy-benzoyl)-benzenesulfonamide | 23.4 | 27.1 | 329.74 | 330 (M + 1) |
| 55 | 2-Chloro-5-(4-hydroxy-benzoyl)-benzenesulfonamide | 25.5 | 27.5 | 313.74 | 312 (M − 1) |
| 56 | N-tert-Butyl-4-(4-chloro-3-sulfamoyl-benzoyl)-benzamide | >30 | 26.7 | 394.88 | 395 (M + 1) |
| 57 | 2-Chloro-5-[4-(pyrrolidine-1-carbonyl)-benzoyl]-benzenesulfonamide | >30 | 21.2 | 392.86 | 393 (M + 1) |
| 58 | 4-(4-Chloro-3-sulfamoyl-benzoyl)-N-phenethyl-benzamide | >30 | 24.2 | 442.92 | 443 (M + 1) |
| 59 | 5-(Biphenyl-4-carbonyl)-2-chloro-benzenesulfonamide | 1.16 | 2.63 | 371.85 | 370 (M − 1) |
| 60 | 2-Chloro-5-(3'-methyl-biphenyl-4-carbonyl)-benzenesulfonamide | 6.31 | 5.44 | 385.87 | 384 (M − 1) |
| 61 | 2-Chloro-5-(4'-methyl-biphenyl-4-carbonyl)-benzenesulfonamide | 1.1 | 1.02 | 385.87 | 384 (M − 1) |
| 62 | 2-Chloro-5-(4'-trifluoromethyl-biphenyl-4-carbonyl)-benzenesulfonamide | 2.21 | 0.83 | 439.84 | 438 (M − 1) |
| 63 | 2-Chloro-5-(4'-ethyl-biphenyl-4-carbonyl)-benzenesulfonamide | 2.05 | 0.38 | 399.9 | 398 (M − 1) |
| 64 | 2-Chloro-5-(2'-fluoro-biphenyl-4-carbonyl)-benzenesulfonamide | 4.05 | 7.55 | 389.84 | 388 (M − 1) |
| 65 | 2-Chloro-5-(4'-fluoro-biphenyl-4-carbonyl)-benzenesulfonamide | 1.18 | 1.61 | 389.84 | 388 (M − 1) |
| 66 | 2-Chloro-5-(4'-chloro-biphenyl-4-carbonyl)-benzenesulfonamide | 0.72 | 0.63 | 406.29 | 405 (M − 1) |
| 67 | 5-(3'-Bromo-biphenyl-4-carbonyl)-2-chloro-benzenesulfonamide | 10.2 | 5.29 | 450.74 | 488 (M − 1) |
| 68 | 2-Chloro-5-(3'-nitro-biphenyl-4-carbonyl)-benzenesulfonamide | 3.44 | 3.15 | 416.84 | 387 (M + 1) |
| 69 | 5-(3'-Amino-biphenyl-4-carbonyl)-2-chloro-benzenesulfonamide | 1.37 | 2.41 | 386.86 | 385 (M − 1) |
| 70 | N-[4'-(4-Chloro-3-sulfamoyl-benzoyl)-biphenyl-3-yl]-acetamide | 11.43 | 4.01 | 428.9 | 429 (M + 1) |
| 71 | 2-Chloro-5-(3'-hydroxymethyl-biphenyl-4-carbonyl)-benzenesulfonic acid | 1.09 | 1.4 | 402.86 | 400 (M − 1) |

TABLE 1-continued

| Example # | IUPAC Name | MMP02 IC$_{50}$ (μM) | MMP13 IC$_{50}$ (μM) | MW (Calc'd) | MW (Found) |
|---|---|---|---|---|---|
| 72 | 2-Chloro-5-(4'-formyl-biphenyl-4-carbonyl)-benzenesulfonamide | 0.18 | 0.13 | 399.86 | 398 (M − 1) |
| 73 | 4'-(4-Chloro-3-sulfamoyl-benzoyl)-biphenyl-4-carboxylic acid | 0.98 | 0.61 | 415.86 | 414 (M − 1) |
| 74 | 4'-(4-Chloro-3-sulfamoyl-benzoyl)-biphenyl-4-carboxylic acid methyl ester | 0.93 | 0.24 | 429.88 | 428 (M − 1) |
| 78 | 2-Chloro-5-(4-dimethylamino-benzoyl)-benzenesulfonamide | 0.27 | 0.35 | 338.82 | 339 (M + 1) |
| 79 | 2-Chloro-5-(4-diethylamino-benzoyl)-benzenesulfonamide | 5.72 | 10.42 | 366.87 | 367 (M + 1) |
| 80 | 2-Chloro-5-(4-pyrrolidin-1-yl-benzoyl)-benzenesulfonamide | 0.055 | 0.113 | 364.85 | 365 (M + 1) |
| 81 | 2-Chloro-5-[4-(2,5-dihydro-pyrrol-1-yl)-benzoyl]-benzenesulfonamide | 1.31 | 1.01 | 362.84 | 361 (M − 1) |
| 82 | 2-Chloro-5-(4-pyrrol-1-yl-benzoyl)-benzenesulfonamide | 1.15 | 0.86 | 360.82 | 359 (M − 1) |
| 83 | 2-Chloro-5-(4-piperidin-1-yl-benzoyl)-benzenesulfonamide | 0.87 | 1.77 | 378.88 | 379 (M + 1) |
| 84 | 2-Chloro-5-[4-(3-methyl-piperidin-1-yl)-benzoyl]-benzenesulfonamide | 1.35 | 7.54 | 392.91 | 393 (M + 1) |
| 85 | 2-Chloro-5-[4-(4-phenyl-piperidin-1-yl)-benzoyl]-benzenesulfonamide | 2.05 | 0.57 | 454.98 | 453 (M − 1) |
| 86 | 5-[4-(4-Benzyl-piperidin-1-yl)-benzoyl]-2-chloro-benzenesulfonamide | >30 | 7.67 | 469.01 | 470 (M + 1) |
| 87 | 2-Chloro-5-[4-(4-methyl-piperazin-1-yl)-benzoyl]-benzenesulfonamide | 1.74 | 1.19 | 393.9 | 394 (M + 1) |
| 88 | 2-Chloro-5-(4-morpholin-4-yl-benzoyl)-benzenesulfonamide | 0.96 | 1.84 | 380.85 | 381 (M + 1) |
| 89 | 2-Chloro-5-[4-(2-oxo-azetidin-1-yl)-benzoyl]-benzenesulfonamide | 2.06 | 3.34 | 364.81 | 365 (M + 1) |
| 90 | 5-(4-Azepan-1-yl-benzoyl)-2-chloro-benzenesulfonamide | 13.8 | 10.8 | 392.91 | 393 (M + 1) |
| 91 | 2-Chloro-5-(4-methoxy-benzoyl)-N-[2-(4-nitro-phenyl)-ethyl]-benzenesulfonamide | >30 | 22.5 | 474.92 | 391 (M + 1) |
| 92 | 2-Chloro-5-(4-phenylamino-benzoyl)-benzenesulfonamide | 22.2 | 20.7 | 386.86 | 387 (M + 1) |
| 93 | 2-Chloro-5-(naphthalene-2-carbonyl)-benzenesulfonamide | 26.5 | 13.71 | 345.81 | 344 (M − 1) |
| 94 | 2-Chloro-5-(indane-5-carbonyl)-benzenesulfonamide | 23.5 | 22.6 | 335.81 | 336 (M + 1) |
| 95 | 2-Chloro-5-(1H-pyrrole-3-carbonyl)-benzenesulfonamide | 3.97 | 6.21 | 284.72 | 285 (M + 1) |
| 96 | 2-Chloro-5-(thiophene-2-carbonyl)-benzenesulfonamide | 10 | 14.7 | 301.77 | 300.0 (M − 1) |
| 97 | 5-(3H-Benzoimidazole-5-carbonyl)-2-chloro-benzenesulfonamide | 1.21 | 0.63 | 335.77 | 334 (M − 1) |
| 98 | 2-Chloro-5-(2-methyl-3H-benzoimidazole-5-carbonyl)-benzenesulfonamide | 2.25 | 8.31 | 349.8 | 348 (M − 1) |
| 99 | 2-Chloro-5-(3-ethyl-1H-indazole-6-carbonyl)-benzenesulfonamide | 0.27 | 0.25 | 363.83 | 364 (M + 1) |
| 100 | 2-Chloro-5-(3-methyl-1H-indazole-6-carbonyl)-benzenesulfonamide | 0.26 | 0.25 | 349.8 | 350 (M + 1) |
| 101 | 2-Chloro-5-(3-isopropyl-1H-indazole-6-carbonyl)-benzenesulfonamide | 6.35 | 3.65 | 377.85 | 378 (M + 1) |
| 102 | 5-(9H-Carbazole-2-carbonyl)-2-chloro-benzenesulfonamide | 1.01 | 2.71 | 384.84 | 385 (M + 1) |
| 103 | 7-(4-Chloro-3-sulfamoyl-benzoyl)-1,3,4,5-tetrahydro-pyrido[4,3-b]indole-2-carboxylic acid ethyl ester | 0.85 | 0.36 | 461.93 | 462 (M + 1) |
| 104 | 8-(4-Chloro-3-sulfamoyl-benzoyl)-1,3,4,5-tetrahydro-pyrido[4,3-b]indole-2-carboxylic acid ethyl ester | 21.45 | 1.9 | 461.93 | 462 (M + 1) |
| 105 | 2-Chloro-5-(1-oxo-2,3,4,9-tetrahydro-1H-beta-carboline-7-carbonyl)-benzenesulfonamide | 8 | 9 | 403.85 | 402.0 (M − 1) |
| 106 | 2-Chloro-5-[2-(2,2-dimethyl-propionyl)-2,3,4,9-tetrahydro-1H-beta-carboline-6-carbonyl]-benzenesulfonamide | >2.7 | 0.95 | 473.98 | 472.1 (M − 1) |
| 109 | 2-Chloro-5-[4-(2,5-dimethyl-pyrrol-1-yl)-3-fluoro-benzoyl]-benzenesulfonamide | 21.8 | 19.9 | 406.87 | 407 (M + 1) |
| 110 | 2-Chloro-5-(2,3-dihydro-1H-indole-5-carbonyl)-benzenesulfonamide | 12.0 | 16.1 | 336.8 | 335 (M − 1) |
| 111 | 5-(1-Benzyl-3-ethyl-1H-indazole-6-carbonyl)-2-chloro-benzenesulfonamide | >30 | 25.3 | 453.95 | 454 (M + 1) |
| 112 | 2-Chloro-5-[3-(2-cyclopentyl-ethyl)-1H-indazole-6-carbonyl]-benzenesulfonamide | 2.95 | 0.129 | 431.94 | 432 (M + 1) |
| 113 | 2-Chloro-5-(1H-indole-3-carbonyl)-benzenesulfonamide | 8.94 | 3.08 | 334.78 | 333 (M − 1) |
| 114 | 2-Chloro-5-(1-methyl-1H-indole-5-carbonyl)-benzenesulfonamide | 3.31 | 3.13 | 348.81 | 347 (M − 1) |
| 116 | 2-Chloro-5-(1H-indole-5-carbonyl)-benzenesulfonamide | 15.4 | 15.3 | 334.78 | 335 (M + 1) |

TABLE 1-continued

| Example # | IUPAC Name | MMP02 IC$_{50}$ (μM) | MMP13 IC$_{50}$ (μM) | MW (Calc'd) | MW (Found) |
|---|---|---|---|---|---|
| 117 | 2-Chloro-5-[1-(3-methyl-butyl)-1H-indole-5-carbonyl]-benzenesulfonamide | 26.7 | 23.0 | 404.92 | 403 (M − 1) |
| 118 | 2-Chloro-5-(3-phenyl-1H-indole-6-carbonyl)-benzenesulfonamide | 2.00 | 1.03 | 410.88 | 409 (M − 1) |
| 119 | 2-Chloro-5-[3-(4-methoxy-phenyl)-1H-indole-6-carbonyl]-benzenesulfonamide | 24 | 6.04 | 440.91 | 439 (M − 1) |
| 120 | 2-Chloro-5-[3-(4-fluoro-phenyl)-1H-indole-6-carbonyl]-benzenesulfonamide | 1.9 | 0.95 | 428.87 | 427 (M − 1) |
| 121 | 5-[3-(3-Acetyl-phenyl)-1H-indole-6-carbonyl]-2-chloro-benzenesulfonamide | 3.9 | 0.59 | 452.92 | 452 (M − 1) |
| 122 | 5-[3-(4-Acetyl-phenyl)-1H-indole-6-carbonyl]-2-chloro-benzenesulfonamide | 12.5 | 1.45 | 452.92 | 451 (M − 1) |
| 123 | 2-Chloro-5-[3-(3-methanesulfonyl-phenyl)-1H-indole-6-carbonyl]-benzenesulfonamide | 5.02 | 0.39 | 488.97 | 487 (M − 1) |
| 124 | 2-Chloro-5-[3-(4-methanesulfonyl-phenyl)-1H-indole-6-carbonyl]-benzenesulfonamide | 19.7 | 0.54 | 488.97 | 487 (M − 1) |
| 125 | 2-Chloro-5-[3-(4-ethanesulfonyl-phenyl)-1H-indole-6-carbonyl]-benzenesulfonamide | >30 | 1.01 | 503 | 501 (M − 1) |
| 126 | 5-(3-Biphenyl-4-yl-1H-indole-6-carbonyl)-2-chloro-benzenesulfonamide | 22.8 | 10 | 486.98 | 485 (M − 1) |
| 127 | 2-Chloro-5-(3-thiophen-3-yl-1H-indole-6-carbonyl)-benzenesulfonamide | 4.6 | 1.6 | 416.91 | 415 (M − 1) |
| 128 | 5-[3-(5-Acetyl-thiophen-2-yl)-1H-indole-6-carbonyl]-2-chloro-benzenesulfonamide | 6.9 | 0.16 | 458.95 | 451 (M − 1) |
| 129 | 5-(1H,1'H-[3,5']Biindolyl-6-carbonyl)-2-chloro-benzenesulfonamide | 2.95 | 1.65 | 449.92 | 447 (M − 1) |
| 130 | 2-Chloro-5-(3-pyridin-3-yl-1H-indole-6-carbonyl)-benzenesulfonamide | 2.62 | 0.24 | 411.87 | 410 (M − 1) |
| 131 | 2-Chloro-5-(3-pyrimidin-5-yl-1H-indole-6-carbonyl)-benzenesulfonamide | 4 | 0.195 | 412.86 | 411 (M − 1) |
| 132 | 2-Chloro-5-{3-[4-(morpholine-4-carbonyl)-phenyl]-1H-indole-6-carbonyl}-benzenesulfonamide | 16 | 0.73 | 524 | 522 (M − 1) |
| 133 | 2-Chloro-5-[3-(3,5-dimethyl-isoxazol-4-yl)-1H-indole-6-carbonyl]-benzenesulfonamide | 23 | 0.30 | 429.89 | 428 (M − 1) |
| 134 | 2-Chloro-5-[3-(5-chloro-2-methoxy-pyridin-4-yl)-1H-indole-6-carbonyl]-benzenesulfonamide | 23 | 0.10 | 476.34 | 474 (M − 1) |
| 135 | 2-Chloro-5-(3-pyridin-4-yl-1H-indole-6-carbonyl)-benzenesulfonamide | 1.05 | 0.09 | 411.87 | 410 (M − 1) |
| 136 | 2-Chloro-5-[3-(2-chloro-pyridin-4-yl)-1H-indole-6-carbonyl]-benzenesulfonamide | 18 | 0.25 | 446.31 | 444 (M − 1) |
| 137 | 2-Chloro-5-[3-(2-methyl-pyridin-4-yl)-1H-indole-6-carbonyl]-benzenesulfonamide | 3.45 | 0.041 | 425.9 | 424 (M − 1) |
| 138 | 2-Chloro-5-[3-(2-ethyl-pyridin-4-yl)-1H-indole-6-carbonyl]-benzenesulfonamide | 3.55 | 0.06 | 439.92 | 438 (M − 1) |
| 139 | 2-Chloro-5-[3-(2-cyclopropyl-pyridin-4-yl)-1H-indole-6-carbonyl]-benzenesulfonamide | 4.15 | 0.068 | 451.94 | 450 (M − 1) |
| 141 | 2-Chloro-5-{3-[2-(3-morpholin-4-yl-propyl)-pyridin-4-yl]-1H-indole-6-carbonyl}-benzenesulfonamide | 1.1 | 0.02 | 539.06 | 539 (M + 1) |
| 142 | 2-Chloro-5-{3-[2-(2-dimethylamino-ethoxy)-pyridin-4-yl]-1H-indole-6-carbonyl}-benzenesulfonamide | 0.2 | 0.017 | 498.99 | 497 (M − 1) |
| 143 | 2-Chloro-5-{3-[2-(2-morpholin-4-yl-ethoxy)-pyridin-4-yl]-1H-indole-6-carbonyl}-benzenesulfonamide | 2.85 | 0.15 | 541.03 | 539 (M − 1) |
| 144 | 2-Fluoro-5-(1H-indole-6-carbonyl)-benzenesulfonamide | 0.39 | 0.3 | 318.33 | 317 (M − 1) |
| 145 | 5-(1H-Indole-6-carbonyl)-2-methyl-benzenesulfonamide | 0.20 | 0.1 | 314.37 | 313 (M − 1) |
| 146 | 3-(1H-Indole-6-carbonyl)-benzenesulfonamide | 0.24 | 0.2 | 300.34 | 299 (M − 1) |
| 147 | 2-Methyl-5-[3-(2-methyl-pyridin-4-yl)-1H-indole-6-carbonyl]-benzenesulfonamide | 2.4 | 0.02 | 405.48 | 404 (M − 1) |

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

We claim:

1. A method of treating a disorder or a disease in a subject mediated by MMP-2, and/or MMP-8, and/or MMP-9, and/or MMP-12 and/or MMP-13, comprising:

administering to the subject a therapeutically effective amount of a compound of formula (III)

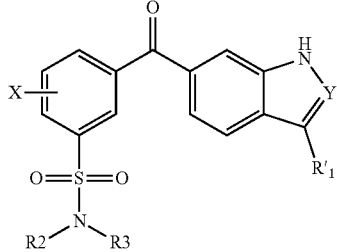

(III)

wherein $R'_1$ is selected from hydrogen, alkyl, cycloakyl, $R_5C(O)-$, $R_6SO_2-$, $(R_7)NH-C(O)-$, and $(R_8)(R_9)N-$, aryl, heteroaryl, heterocycloalkyl, said aryl, heteroaryl, and heterocycloalkyl are optionally substituted by one or two substituents selected from alkyl-$SO_2-$, alkyl-C(O)—, heterocycloalkyl-alkyl-, alkyl-alkoxy-, alkoxy-, alkyl, aryl, cycloalkyl, halo, alkoxy-alkyl-, alkyl-O—C(O)—, cycloalkyl-alkyl-, dialkylamino-alkoxy-, and dialkylamino-alkyl-;

wherein $R_5$, $R_6$, $R_7$, $R_8$ and $R_9$ are independently alkyl or aryl, each of which is optionally substituted by one to five substituents selected from the group consisting of $(C_1-C_7)$ alkyl, halo, hydroxy, $(C_1-C_7)$ alkoxy, and aryl;

$R_2$ and $R_3$ are hydrogen;

X is selected from hydrogen, cyano, halogen, nitro, alkyl-S—, alkyl-SO—, alkyl-$SO_2$—, $H_2N$—$SO_2$—, $R_5$—C(O)—, alkyl, and $R_4$—O, wherein $R_4$ and $R_5$ are independently alkyl or aryl each of which is optionally substituted by substituents selected from the group consisting of $(C_1-C_7)$ alkyl, halo, hydroxy, $(C_1-C_7)$ alkoxy, and aryl;

Y is C or N; or a pharmaceutically acceptable salt thereof, or an optical isomer thereof; or a mixture of optical isomers; wherein the disorder or disease is selected from Alport syndrome, asthma, rhinitis, chronic obstructive pulmonary diseases (COPD), arthritis, atherosclerosis, cancer metastasis, loosening of hip joint replacements, periodontal disease, and fibrotic disease of the lung.

2. The method of claim 1, wherein $R'_1$ is selected from hydrogen, $(C_1-C_4)$ alkyl, $(C_6-C_{12})$ aryl, (5-9) membered heteroaryl, $(C_3-C_7)$ cycloalkyl-$(C_1-C_4)$ alkyl-, each of which is optionally substituted by one or two substituents selected from the group consisting of $(C_1-C_4)$ alkyl-$SO_2$—, $(C_1-C_4)$ alkyl-C(O)—, (5-9) membered-heterocycloalkyl-$(C_1-C_4)$ alkyl-, $(C_1-C_4)$ alkyl-$(C_1-C_4)$ alkoxy-, $(C_1-C_4)$ alkoxy-, $(C_1-C_4)$ alkyl, $(C_3-C_7)$ cycloalkyl, halogen, $(C_1-C_4)$ alkoxy-$(C_1-C_4)$ alkyl-, $(C_1-C_4)$ $(C_1-C_4)$ dialkylamino-$(C_1-C_4)$ alkoxy-, and $(C_1-C_4)$ dialkylamino-$(C_1-C_4)$ alkyl-;

$R_2$ and $R_3$ are hydrogen;

X is hydrogen, halogen, or $(C_1-C_7)$ alkyl; or a pharmaceutically acceptable salt thereof, or an optical isomer thereof; or a mixture of optical isomers.

3. The method of claim 1, wherein $R'_1$ is hydrogen, $(C_1-C_4)$ alkyl, phenyl, pyridine, said pyridine is optionally substituted by one or two substituents selected from $(C_3-C_7)$ cycloalkyl, $(C_1-C_4)$ alkyl, halo, $(C_1-C_4)$ alkoxy-$(C_1-C_4)$ alkyl-, (5-9) membered-heterocycloalkyl-$(C_1-C_4)$ alkyl-, (5-9) membered-heterocycloalkyl-$(C_1-C_4)$ alkoxy-, and $(C_1-C_4)$ dialkylamino-$(C_1-C_4)$ alkyl-; $R_2$ and $R_3$ are hydrogen; X is halogen; Y is C or N; or a pharmaceutically acceptable salt thereof, or an optical isomer thereof; or a mixture of optical isomers.

4. The method of claim 1, wherein the disorder or the disease is Alport syndrome.

5. The method of claim 1 wherein the compound is 2-Chloro-5-(3-ethyl-1H-indazole-6-carbonyl)-benzenesulfonamide, 2-Chloro-5-(3-methyl-1H-indazole-6-carbonyl)-benzenesulfonamide or 2-Chloro-5-(3-isopropyl-1H-indazole-6-carbonyl)-benzenesulfonamide; or a pharmaceutically acceptable salt thereof.

6. The method of claim 4 wherein the compound is 2-Chloro-5-(3-ethyl-1H-indazole-6-carbonyl)-benzenesulfonamide, 2-Chloro-5-(3-methyl-1H-indazole-6-carbonyl)-benzenesulfonamide or 2-Chloro-5-(3-isopropyl-1H-indazole-6-carbonyl)-benzenesulfonamide; or a pharmaceutically acceptable salt thereof.

* * * * *